United States Patent
Pagratis et al.

(10) Patent No.: US 6,346,611 B1
(45) Date of Patent: *Feb. 12, 2002

(54) HIGH AFFINITY TGFβ NUCLEIC ACID LIGANDS AND INHIBITORS

(75) Inventors: Nikos Pagratis, Boulder; Michael Lochrie, Louisville; Larry Gold, Boulder, all of CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/363,939

(22) Filed: Jul. 29, 1999

Related U.S. Application Data

(63) Continuation-in-part of application No. 09/046,247, filed on Mar. 23, 1998, now Pat. No. 6,124,449, which is a continuation-in-part of application No. 08/458,424, filed on Jun. 2, 1995, now Pat. No. 5,731,424, which is a continuation-in-part of application No. 07/714,131, filed on Jun. 10, 1991, now Pat. No. 5,475,096, application No. 09/363,939, which is a continuation-in-part of application No. 08/117,991, filed on Sep. 8, 1993, now abandoned, and a continuation-in-part of application No. 07/964,624, filed on Oct. 21, 1992, now Pat. No. 5,496,938, and a continuation-in-part of application No. 07/931,473, filed on Aug. 17, 1992, now Pat. No. 5,270,163, said application No. 07/714,131, is a continuation-in-part of application No.07/536,428, filed on Jun. 11, 1990, now abandoned, application No. 09/363,939, which is a continuation-in-part of application No. 08/434,465, filed on May 4, 1995, now Pat. No. 6,011,020.

(51) Int. Cl.[7] .......................... C07H 21/04; C07H 21/02
(52) U.S. Cl. ........................................ 536/23.1; 514/44
(58) Field of Search ................................ 536/254, 23.1; 514/44

(56) References Cited

U.S. PATENT DOCUMENTS

| | | | |
|---|---|---|---|
| 5,723,323 A | 3/1998 | Kauffman et al. | ............. 435/6 |
| 5,731,424 A * | 3/1998 | Toothman et al. | ......... 536/23.1 |
| 5,859,228 A | 1/1999 | Janjic et al. | .................... 435/6 |
| 6,011,020 A * | 1/2000 | Gold et al. | .................... 514/44 |

FOREIGN PATENT DOCUMENTS

| | | |
|---|---|---|
| GB | 2 183 661 A | 6/1987 |
| WO | WO89/06694 | 7/1989 |
| WO | WO 91/19813 | 12/1991 |
| WO | WO92/14843 | 9/1992 |

OTHER PUBLICATIONS

Joyce (1989) Gene 82:83.
Joyce & Inoue (1989) Nucleic Acids Research 17:711.
Ellington & Szostak (1990) Abstracts of papers presented at the 1990 meeting on RNA Processing, Cold Spring Harbor Laboratory, Cold Spring Harbor, NY, p. 84.
Kinzler & Vogelstein (1989) Nucleic Acids Research 17:3645.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Thiesen & Bach (1990) Nucleic Acids Research 18:3203.
Szostak, "Structure and Activity of Ribozymes," in *Redesigning the Molecules of Life*, (S.A. Benner ed.) Springer–Verlag Berline Heidelberg, pp. 87–113 (1988).

* cited by examiner

*Primary Examiner*—Stephanie W. Zitomer
(74) *Attorney, Agent, or Firm*—Swanson & Bratschun, LLC

(57) ABSTRACT

Methods are described for the identification and preparation of high-affinity nucleic acid ligands to TGFβ2. Included in the invention are specific RNA ligands to TGFβ2 identified by the SELEX method. Also included are RNA ligands that inhibit the interaction of TGFβ2 with its receptor.

5 Claims, 11 Drawing Sheets

Fig. 8

TGFβ2 LIGAND=
rGrGrArGrGfUfUrAfUfUrAfCrArGrArGfUfCfUrGfUfUrArGfCfUrGfUrAfCfUfCfC-3'-3'-dT
(SEQ ID NO:115)

SEQ ID NO:216

HIGH AFFINITY TGFβ NUCLEIC ACID LIGANDS AND INHIBITORS

RELATED APPLICATIONS

This application is a Continuation-in-Part of U.S. patent application Ser. No. 09/046,247, filed Mar. 23, 1998, U.S. Pat. No. 6,124,449 entitled "High Affinity TGFβ Nucleic Acid Ligands and Inhibitors," which is a Continuation-in-Part of U.S. patent application Ser. No. 08/458,424, filed Jun. 2, 1995, entitled "High Affinity TGFβ Nucleic Acid Ligands and Inhibitors", now issued as U.S. Pat. No. 5,731,424, which is a Continuation-in-Part of U.S. patent application Ser. No. 07/714,131, filed Jun. 10, 1991, entitled "Nucleic Acid Ligands", now issued as U.S. Pat. No. 5,475,096, U.S. patent application Ser. No. 07/931,473, filed Aug. 17, 1992, entitled "Methods for Identifying Nucleic Acid Ligands", now issued as U.S. Pat. No. 5,270,163, U.S. patent application Ser. No. 07/964,624, filed Oct. 21, 1992, entitled "Nucleic Acid Ligands to HIV-RT and HIV-1 Rev", now issued as U.S. Pat. No. 5,496,938, and U.S. patent application Ser. No. 08/117,991, filed Sep. 8, 1993, entitled "High Affinity Nucleic Acid Ligands Containing Modified Nucleotides", now abandoned. U.S. patent application Ser. No. 07/714,131 is a Continuation-in-Part of U.S. patent application Ser. No. 07/536,428, filed Jun. 11, 1990, entitled Systematic Evolution of Ligands by EXponential Enrichment, now abandoned. This application is also a Continuation-in Part of U.S. patent application Ser. No. 08/434,465, filed May 4, 1995, now U.S. Pat. No. 6,011,020, entitled "Nucleic Acid Ligand Complexes," issued Jan. 4, 2000.

FIELD OF THE INVENTION

Described herein are methods for identifying and preparing high affinity nucleic acid ligands that bind human transforming growth factor β2 (TGFβ2). The method utilized herein for identifying such nucleic acid ligands is called SELEX, an acronym for Systematic Evolution of Ligands by EXponential Enrichment. This invention includes high affinity nucleic acids of human TGFβ2. Further disclosed are RNA ligands to TGFβ2. Also included are oligonucleotides containing nucleotide derivatives modified at the 2' position of the pyrimidines. Additionally disclosed are ligands to TGFβ2 containing 2'-OCH$_3$ purine modifications that may have higher stability in serum and in animals. This invention also includes high affinity nucleic acid inhibitors of TGFβ2. The oligonucleotide ligands of the present invention are useful in any process in which binding to TGFβ2 is required. This includes, but is not limited to, their use as pharmaceuticals, diagnostics, imaging agents, and immunohistochemical reagents.

BACKGROUND OF THE INVENTION

Transforming growth factors betas (TGFβs) are part of a superfamily of proteins that includes inhibins, activins, bone morphogenetic and osteogenic proteins, growth/differentiation factors, Mullerian-inhibiting substance, decapentaplegic and 60A (Drosophila), daf-7 and unc-129 (*C. elegans*), and vg1 (Xenopus) (Schlunegger and Grutter (1992) Nature 358:430–434). Three TGFβ isotypes exist in mammals that are called TGFβ1, TGFβ2, and TGFβ3. There is about 80% sequence identity between any pair of mammalian TGFβs. TGFβs bind to at least 5 receptors, but only 2 or 3 of them (types I, II, and possibly V) are signaling receptors. The intracellular signaling pathways activated by TGFβs involve SMAD proteins and are being intensively studied (Padgett, et al. (1998) Pharmacol Ther 78:47–52). The signaling receptors are found on a variety of cells. In turn, a variety of cells express TGFβs.

TGFβs are synthesized as precursors composed of latency-associated protein (LAP) at the amino terminus and mature TGFβ at the carboxyl terminus. The precursor is cleaved and assembles as a homodimer. TGFβs are secreted from cells bound to LAP and latent TGFβ binding proteins (LTBPs). Latent TGFβs are released from LAP and LTBP and become active by a relatively uncharacterized mechanism that may involve proteolysis by plasmin or regulation by thrombospondin (Crawford, et al. (1998) Cell 93:1159–70). The mature, released TGFβ homodimer has a combined molecular weight of ~25000 daltons (112 amino acids per monomer). TGFβ1 and TGFβ2 bind heparin and there are indications that basic amino acids at position 26 are required for heparin binding (Lyon et al. (1997) Jour. Biol. Chem. 272:18000–18006).

The structure of TGFβ2 has been determined using x-ray crystallography (Daopin, et al. (1992) Science 257:369–373; Schlunegger and Grutter (1992) Nature 358:430–434) and is very similar to the structure of TGFβ1. TGFβs belong to a structural family of proteins called the "cysteine knot" proteins that includes vascular endothelial growth factor, nerve growth factor, human chorionic gonadotropin, and platelet-derived growth factor. These proteins are structurally homologous, but have only 10–25% primary sequence homology.

The biological activities of the TGFβs vary (Moses (1990) Growth Factors from Genes to Clinical Application 141–155, Wahl (1994) J. Exp. Med. 180:1587–1590). In some cases they inhibit cell proliferation (Robinson et al. (1991) Cancer Res. 113:6269–6274) and in other cases they stimulate it (Fynan and Reiss (1993) Crit. Rev. Oncogenesis 4:493–540). They regulate extracellular matrix formation and remodeling (Koli and Arteaga (1996) Jour. Mammary Gland Biol. and Neoplasia 1:373–380). They are also are very potent immunosuppressants (Letterio and Roberts (1998) Ann. Rev. Immunol. 16:137–161). TGFβs are thought to play a significant role in fibrotic diseases, preventing the immune system from rejecting tumors (Fakhrai et al. (1996) Proc. Natl. Acad. USA 93:2090–2914), cancer cell growth (Koli and Arteaga (1996) J. Mammary Gland Bio. and Neoplasia 1:373–380, Reiss and Barcellos-Hoff (1997) Breast Cancer Res. and Treatment 45:81–85; Jennings and Pietenpol (1998) J. Neurooncol. 36:123–140), and tumor metastasis. They may have ancillary roles in autoimmune and infectious diseases. Inhibition of TGFβ2 by an expressed antisense RNA (Fakhrai et al. (1996) Proc. Natl. Acad. USA 93:2090–2914) and by exogenous antisense oligonucleotides (Marzo et al. (1997) Cancer Research 57:3200–3207) has been reported to prevent glioma formation in rats.

The gene for mouse TGFβ2 has been deleted (Sanford et al. (1997) Development 124:2659–2670). Mice lacking TGFβ2 function die near birth and have aberrant epithelial-mesencymal interactions that lead to developmental defects in the heart, eye, ear, lung, limb, craniofacial area, spinal cord, and urogenital tracts. These defects, for the most part, do not overlap abnormalities that have been observed in TGFβ1 and TGFβ3 knockout mice. TGFβs have also been overexpressed in cell lines or transgeneic mice (Koli and Arteaga (1996) J. Mammary Gland Bio. and Neoplasia 1:373–380, Bottinger et al. 1997 Kidney Int. 51:1355–1360; Bottinger and Kopp (1998) Miner Electrolyte Metab 24:154–160) with a variety of effects.

A method for the in vitro evolution of nucleic acid molecules with high affinity binding to target molecules has been developed. This method, Systematic Evolution of Ligands by EXponential enrichment, termed SELEX, is described in U.S. patent application Ser. No. 07/536,428, filed Jun. 11, 1990, entitled "Systematic Evolution of Ligands by Exponential Enrichment", now abandoned, U.S. patent application Ser. No. 07/714,131, filed Jun. 10, 1991, entitled "Nucleic Acid Ligands", now U.S. Pat. No. 5,475,096, and U.S. patent application Ser. No. 07/931,473, filed Aug. 17, 1992, entitled "Methods for Identifying Nucleic Acid Ligands", now U.S. Pat. No. 5,270,163 (see also WO91/19813), each of which is herein specifically incorporated by reference. Each of these applications, collectively referred to herein as the SELEX Patent Applications, describe a fundamentally novel method for making a nucleic acid ligand to any desired target molecule.

The SELEX method involves selection from a mixture of candidate oligonucleotides and step-wise iterations of binding, partitioning and amplification, using the same general selection theme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The basic SELEX method may be modified to achieve specific objectives. For example, U.S. patent application Ser. No. 07/960,093, filed Oct. 14, 1992, entitled "Method for Selecting Nucleic Acids on the Basis of Structure", now abandoned, describes the use of SELEX in conjunction with gel electrophoresis to select nucleic acid molecules with specific structural characteristics, such as bent DNA (See U.S. Pat. No. 5,707,796). U.S. patent application Ser. No. 08/123,935, filed Sep. 17, 1993, entitled "Photoselection of Nucleic Acid Ligands", now abandoned, describes a SELEX based method for selecting nucleic acid ligands containing photoreactive groups capable of binding and/or photo-crosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine", now abandoned, describes a method for identifying highly specific nucleic acid ligands able to discriminate between closely related molecules, termed "Counter-SELEX" (See U.S. Pat. No. 5,580,737). U.S. patent application Ser. No. 08/143,564, filed Oct. 25, 1993, entitled "Systematic Evolution of Ligands by EXponential Enrichment: Solution SELEX", now abandoned, (See also U.S. Pat. No. 5,567,588) and U.S. patent application Ser. No. 08/792,075, filed Jan. 31, 1997, entitled "Flow Cell SELEX", now U.S. Pat. No. 5,861,254, describe SELEX-based methods which achieve highly efficient partitioning between oligonucleotides having high and low affinity for a Target molecule. U.S. patent application Ser. No. 07/964,624, filed Oct. 21, 1992, entitled "Nucleic Acid Ligands to HIV-RT and HIV-1 Rev", now U.S. Pat. No. 5,496,938, describes methods for obtaining improved Nucleic Acid Ligands after the SELEX process has been performed. U.S. patent application Ser. No. 08/400,440, filed Mar. 8, 1995, entitled "Systematic Evolution of Ligands by EXponential Enrichment: Chemi-SELEX", now U.S. Pat. No. 5,705,337, describes methods for covalently linking a ligand to its target.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", now abandoned, that describes oligonucleotides containing nucleotide derivatives chemically modified at the 5- and 2'-positions of pyrimidines, as well as specific RNA ligands to thrombin containing 2'-amino modifications (See U.S. Pat. No. 5,660,985). U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement", now abandoned describes oligonucleotides containing various 2'-modified pyrimidines. PCT/US98/00589, WO 98/18480 filed Jan. 7, 1998, entitled "Bioconjugation of Oligonucleotides" describes a method for identifying bioconjugates to a target comprising nucleic acid ligands derivatized with a molecular entity exclusively at the 5'-position of the nucleic acid ligands.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX", now U.S. Pat. No. 5,637,459 and U.S. patent application Ser. No. 08/234,997, filed Apr. 28, 1994, entitled "Systematic Evolution of Ligands by Exponential Enrichment: Blended SELEX", now U.S. Pat. No. 5,683,867 respectively. These applications allow the combination of the broad array of shapes and other properties, and the efficient amplification and replication properties, of oligonucleotides with the desirable properties of other molecules. The full text of the above described patent applications, including but not limited to, all definitions and descriptions of the SELEX process, are specifically incorporated herein by reference in their entirety.

BRIEF SUMMARY OF THE INVENTION

The present invention includes methods of identifying and producing nucleic acid ligands to transforming growth factor beta (TGFβ2) and the nucleic acid ligands so identified and produced. By substantially homologous it is meant a degree of amino acid sequence identity of 70% or more. In particular, RNA sequences are provided that are capable of binding specifically to TGFβ2. Also included are oligonucleotides containing nucleotide derivatives modified at the 2' position of the pyrimidines. Specifically included in the invention are the RNA ligand sequences shown in Tables 5, 7, 8, 11, 13, 14, 16–19, and FIG. 9 (SEQ ID NOS: 21–108 and 128–193). Also included in this invention are RNA ligands of TGFβ2 that inhibit the function of TGFβ2. Also described herein are 2'OMe-modified nucleic acid ligands of TGFβ1.

Further included in this invention is a method of identifying nucleic acid ligands and nucleic acid ligand sequences to TGFβ2, comprising the steps of (a) preparing a candidate mixture of nucleic acids, (b) contacting the candidate mixture of nucleic acids with TGFβ2, (c) partitioning between members of said candidate mixture on the basis of affinity to TGFβ2, and (d) amplifying the selected molecules to yield a mixture of nucleic acids enriched for nucleic acid sequences with a relatively higher affinity for binding to TGFβ2.

More specifically, the present invention includes the RNA ligands to TGFβ2, identified according to the above-described method, including those ligands shown in Tables 5, 7, 8, 11, 13, 14, 16–19, and FIG. 9 (SEQ ID NOS: 21–108 and 128–193). Also included are nucleic acid ligands to TGFβ2 that are substantially homologous to any of the given ligands and that have substantially the same ability to bind TGFβ2 and inhibit the function of TGFβ2. Further included in this invention are nucleic acid ligands to TGFβ2 that have substantially the same structural form as the ligands presented herein and that have substantially the same ability to bind TGFβ2 and inhibit the function of TGFβ2.

The present invention also includes other modified nucleotide sequences based on the nucleic acid ligands identified herein and mixtures of the same.

BRIEF DESCRIPTION OF THE FIGURES

FIG. 8 shows the putative structures of TGFβ2 aptamers. The minimal required sequences were fit into similar structures. Ligand 14i-1t5-41 and 21a-4(ML-110) were transcribed in vitro and contained extra bases at their 5' ends (shown in lower case) to allow efficient in vitro transcription. Bold-faced letters indicate positions that are identical to invariant positions of the biased SELEX with the 21-21 sequence.

DETAILED DESCRIPTION OF THE INVENTION

Figure 1:
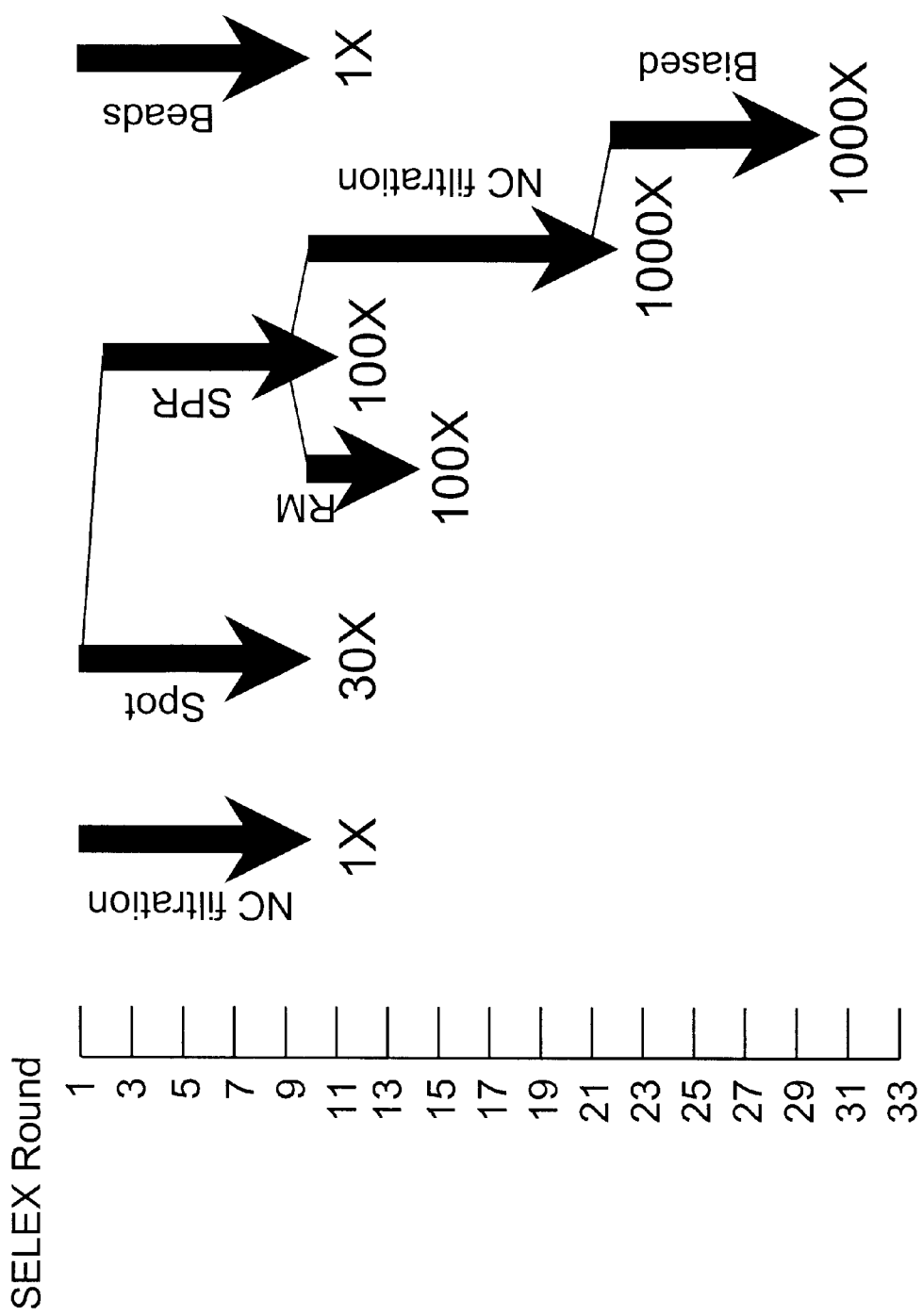
FIG. 1 shows a flow chart summarizing the various SELEX experiments done with TGFβ2. The length of the arrowheads corresponds to the round number shown to the left. Connected arrowheads indicate branches in the SELEX experiments where a pool was used to start a new branch. Under each arrowhead the fold improvement in affinity is also shown.

This application describes high-affinity nucleic acid ligands to TGFβ2 identified through the method known as SELEX. SELEX is described in U.S. patent application Ser. No. 07/536,428, entitled "Systematic Evolution of Ligands by EXponential Enrichment", now abandoned, U.S. patent application Ser. No. 07/714,131, filed Jun. 10, 1991, entitled "Nucleic Acid Ligands", now U.S. Pat. No. 5,475,096, U.S. patent application Ser. No. 07/931,473, filed Aug. 17, 1992, entitled Methods for Identifying "Nucleic Acid Ligands", now U.S. Pat. No. 5,270,163, (see also WO91/19813). These applications, each specifically incorporated herein by reference, are collectively called the SELEX Patent Applications. Nucleic Acid Ligands to TGFβ have been identified through the SELEX method. These TGFβ Nucleic Acid Ligands are described in U.S. patent application Ser. No. 08/458,423, filed Jun. 2, 1995, entitled, "High Affinity TGFβ Nucleic Acid Ligands and Inhibitors," now U.S. Pat. No. 5,731,144, and U.S. patent application Ser. No. 09/046,247, filed Mar. 23, 1998, entitled "High Affinity TGFβ Nucleic Acid Ligancls and Inhibitors," and U.S. patent application Ser. No. 09/275,850, filed Mar. 24, 1999, entitled "The Truncation SELEX Method." These applications are specifically incorporated herein in their entirety.

Certain terms used to described the invention herein are defined as follows:

"Nucleic Acid Ligand" as used herein is a non-naturally occurring nucleic acid having a desirable action on a target. Nucleic Acid Ligands are also referred to herein as "aptamers." A desirable action includes, but is not limited to, binding of the target, catalytically changing the target, reacting with the target in a way which modifies/alters the target or the functional activity of the target, covalently attaching to the target as in a suicide inhibitor, and facilitating the reaction between the target and another molecule. In the preferred embodiment, the desirable action is specific binding to a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

"Candidate Mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to TGFβ2. The SELEX methodology is described in the SELEX Patent Applications.

"Target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the target is TGFβ2.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The SELEX method further encompasses combining selected nucleic acid ligands with lipophilic or non-immunogenic, high molecular weight compounds in a diagnostic or therapeutic complex as described in U.S. patent application Ser. No. 08/434,465, filed May 4, 1995, entitled "Nucleic Acid Ligand Complexes", now U.S. Pat. No. 6,011,020. VEGF nucleic acid ligands that are associated with a Lipophilic Compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes" now U.S. Pat. No. 5,859,228. VEGF nucleic acid ligands that are associated with a Lipophilic Compound, such as a glycerol lipid, or a non-immunogenic, high molecular weight Compound, such as polyalkylene glycol, are further described in U.S. patent application Ser. No. 08/897,351, filed Jul. 21, 1997, entitled "Vascular Endothelial Growth Factor (VEGF) Nucleic Acid Ligand Complexes", now U.S. Pat. No. 6,051,698. VEGF nucleic acid ligands that are associated with a non-immunogenic, high molecular weight compound or lipophilic compound are also further described in PCT/US 97/18944 (WO 98/18480), filed Oct. 17, 1997, entitled "Vascular Endothelial Growth Factor (VEGF) Nucleic Acid Ligand Complexes". Each of the above described patent applications which describe modifications of the basic SELEX procedure are specifically incorporated by reference herein in their entirety.

In certain embodiments of the present invention it is desirable to provide a complex comprising one or more nucleic acid ligands to TGFβ2 covalently linked with a non-immunogenic, high molecular weight compound or lipophilic compound. A complex as used herein describes the molecular entity formed by the covalent linking of the nucleic acid ligand of TGFβ2 to a non-immunogenic, high molecular weight compound. A non-immunogenic, high molecular weight compound is a compound between approximately 100 Da to 1,000,000 Da, more preferably approximately 1000 Da to 500,000 Da, and most preferably approximately 1000 Da to 200,000 Da, that typically does not generate an immunogenic response. For the purposes of this invention, an immunogenic response is one that causes the organism to make antibody proteins. In one preferred embodiment of the invention, the non-immunogenic, high molecular weight compound is a polyalkylene glycol. In the most preferred embodiment, the polyalkylene glycol is polyethylene glycol (PEG). More preferably, the PEG has a molecular weight of about 10–80K. Most preferably, the PEG has a molecular weight of about 20–45K. In certain embodiments of the invention, the non-immunogenic, high molecular weight compound can also be a nucleic acid ligand.

In another embodiment of the invention it is desirable to have a complex comprised of a nucleic acid ligand to TGFβ2 and a lipophilic compound. Lipophilic compounds are compounds that have the propensity to associate with or partition into lipid and/or other materials or phases with low dielectric constants, including structures that are comprised substantially of lipophilic components. Lipophilic compounds include lipids as well as non-lipid containing compounds that have the propensity to associate with lipid (and/or other materials or phases with low dielectric constants). Cholesterol, phospholipid, and glycerol lipids, such as dialkylglycerol, diacylglycerol, and glycerol amide lipids are further examples of lipophilic compounds. In a preferred embodiment, the lipophilic compound is a glycerol lipid.

The non-immunogenic, high molecular weight compound or lipophilic compound may be covalently bound to a variety of positions on the nucleic acid ligand to TGFβ2, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the nucleic acid ligand to TGFβ2. In embodiments where the lipophilic compound is a glycerol lipid, or the non-immunogenic, high molecular weight compound is polyalkylene glycol or polyethylene glycol, preferably the non-immunogenic, high molecular weight compound is bonded to the 5' or 3' hydroxyl of the phosphate group thereof. In the most preferred embodiment, the lipophilic compound or non-immunogenic, high molecular weight compound is bonded to the 5' hydroxyl of the phosphate group of the nucleic acid ligand. Attachment of the non-immunogenic, high molecular weight compound or lipophilic compound to the nucleic acid ligand of TGFβ can be done directly or with the utilization of linkers or spacers.

A linker is a molecular entity that connects two or more molecular entities through covalent bonds or non-covalent interactions, and can allow spatial separation of the molecular entities in a manner that preserves the functional properties of one or more of the molecular entities. A linker can also be known as a spacer.

The complex comprising a nucleic acid ligand to TGFβ2 and a non-immunogenic, high molecular weight compound or lipophilic compound can be further associated with a lipid construct. Lipid constructs are structures containing lipids, phospholipids, or derivatives thereof comprising a variety of different structural arrangements which lipids are known to adopt in aqueous suspension. These structures include, but are not limited to, lipid bilayer vesicles, micelles, liposomes, emulsions, lipid ribbons or sheets, and may be complexed with a variety of drugs and components which are known to be pharmaceutically acceptable. In the preferred embodiment, the lipid construct is a liposome. The preferred liposome is unilamellar and has a relative size less than 200 nm. Common additional components in lipid constructs include cholesterol and alpha-tocopherol, among others. The lipid constructs may be used alone or in any combination which one skilled in the art would appreciate to provide the characteristics desired for a particular application. In addition, the technical aspects of lipid constructs and liposome formation are well known in the art and any of the methods commonly practiced in the field may be used for the present invention.

The SELEX method further comprises identifying bioconjugates to a target. Copending PCT Patent Application No. US98/00589 (WO 98/30720), filed Jan. 7, 1998, entitled "Bioconjugation of Oligonucleotides" describes a method for enzymatically synthesizing bioconjugates comprising RNA derivatized exclusively at the 5'-position with a molecular entity, and a method for identifying bioconjugates to a target comprising nucleic acid ligands derivatized with a molecular entity exclusively at the 5'-position of the nucleic acid ligands. A bioconjugate as used herein refers to any oligonucleotide which has been derivatized with another molecular entity. In the preferred embodiment, the molecular entity is a macromolecule. As used herein, a macromolecule refers to a large organic molecule. Examples of macromolecules include, but are not limited to nucleic acids, oligonucleotides, proteins, peptides, carbohydrates, polysaccharides, glycoproteins, lipophilic compounds, such as cholesterol, phospholipids, diacyl glycerols and dialkyl glycerols, hormones, drugs, non-immunogenic high molecular weight compounds, fluorescent, chemiluminescent and bioluminescent marker compounds, antibodies and biotin, etc. without limitation. In certain embodiments, the molecular entity may provide certain desirable characteristics to the nucleic acid ligand, such as increasing RNA hydrophobicity and enhancing binding, membrane partitioning and/or permeability. Additionally, reporter molecules, such as biotin, fluorescein or peptidyl metal chelates for incorporation of diagnostic radionuclides may be added, thus providing a bioconjugate which may be used as a diagnostic agent.

The methods described herein and the nucleic acid ligands identified by such methods are useful for both therapeutic and diagnostic purposes. Therapeutic uses include the treatment or prevention of diseases or medical conditions in human patients. Therapeutic uses may also include veterinary applications.

Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art or by the methods described in PCT/US98/00589 (WO 98/30720). Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to TGFβ2 described herein may specifically be used for identification of the TGFβ2 protein.

SELEX provides high affinity ligands of a target molecule. This represents a singular achievement that is unprecedented in the field of nucleic acids research. The present invention applies the SELEX procedure to the specific target of TGFβ1. In the Example section below, the experimental parameters used to isolate and identify the nucleic acid ligands to TGFβ2 are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624), methods are described for obtaining improved nucleic acid ligands after SELEX has been performed. The '624 application, entitled "Nucleic Acid Ligands to HIV-RT and HIV-1 Rev", now issued as U.S. Pat. No. 5,496,938, is specifically incorporated herein by reference.

In the present invention, SELEX experiments were performed in order to identify RNA ligands with specific high affinity for TGFβ2 from degenerate libraries containing 33, 34 or 40 random positions (33N, 34N or 40N) (Table 1). This invention includes the specific RNA ligands to TGFβ2 shown in Tables 5, 7, 8, 11, 13, 14, 16–19, and FIG. 9 (SEQ ID NOS: (21–108 and 128–193)), identified by the methods described in Example 1. This invention further includes RNA ligands to TGFβ2 which inhibit TGFβ2 function, presumably by inhibiting the interaction of TGFβ2 with its receptor. The scope of the ligands covered by this invention extends to all nucleic acid ligands of TGFβ2, modified and unmodified, identified according to the SELEX procedure. More specifically, this invention includes nucleic acid sequences that are substantially homologous to the ligands shown in Tables 5, 7, 8, 11, 13, 14, 16–19, and FIG. 9 (SEQ ID NOS: (21–108 and 128–193)). By substantially homologous it is meant a degree of primary sequence homology in excess of 70%, most preferably in excess of 80%, and even more preferably in excess of 90%, 95% or 99%. The percentage of homology as described herein is calculated as the percentage of nucleotides found in the smaller of the two sequences which align with identical nucleotide residues in the sequence being compared when 1 gap in a length of 10 nucleotides may be introduced to assist in that alignment. A review of the sequence homologies of the ligands of TGFβ2, shown in Tables 5, 7, 8, 11, 13, 14, 16–19, and FIG. 9 (SEQ ID NOS: (21–108 and 128–193)) shows that some sequences with little or no primary homology may have substantially the same ability to bind TGFβ2. For these reasons, this invention also includes nucleic acid ligands that have substantially the same structure and ability to bind TGFβ2 as the nucleic acid ligands shown in Tables 5, 7, 8, 11, 13, 14, 16–19, and FIG. 9 (SEQ ID NOS: (21–108 and 128–193)). Substantially the same ability to bind TGFβ2 means that the affinity is within one or two orders of magnitude of the affinity of the ligands described herein. It is well within the skill of those of ordinary skill in the art to determine whether a given sequence—substantially homologous to those specifically described herein—has substantially the same ability to bind TGFβ.

This invention also includes nucleic acid ligands that have substantially the same postulated structure or structural motifs. Substantially the same structure or structural motifs can be postulated by sequence alignment using the Zuker-fold program (see Zuker (1989) Science 244:48–52). As would be known in the art, other computer programs can be used for predicting secondary structure and structural motifs. Substantially the same structure or structural motif of nucleic acid ligands in solution or as a bound structure can also be postulated using NMR or other techniques as would be known in the art.

One potential problem encountered in the therapeutic, prophylactic, and in vivo diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep.

8, 1993, entitled "High Affinity Nucleic Acid Ligands Containing Modified Nucleotides", now abandoned and U.S. patent application Ser. No. 08/434,465, filed May 4, 1995, entitled "Nucleic Acid Ligand Complexes", which are specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the nucleic acid ligands are derived by the SELEX method, the modifications can be pre- or post-SELEX modifications. Pre-SELEX modifications yield nucleic acid ligands with both specificity for their SELEX Target and improved in vivo stability. Post-SELEX modifications made to 2'-OH nucleic acid ligands can result in improved in vivo stability without adversely affecting the binding capacity of the nucleic acid ligand. The preferred modifications of the nucleic acid ligands of the subject invention are 5' and 3' phosphorothioate capping and/or 3'-3' inverted phosphodiester linkage at the 3' end. In one preferred embodiment, the preferred modification of the nucleic acid ligand is a 3'-3' inverted phosphodiester linkage at the 3' end. Additional 2'-fluoro (2'-F) and/or 2'-amino (2'-$NH_2$) and/or 2'-O methyl (2'-OMe) and/or 2'-$OCH_3$ modification of some or all of the nucleotides is preferred. Described herein are nucleic acid ligands that were 2'-F modified and incorporated into the SELEX process. Also described herein are nucleic acid ligands that were 2'-$OCH_3$ modified after the SELEX process was performed.

Other modifications are known to one of ordinary skill in the art. Such modifications may be made post-SELEX (modification of previously identified unmodified ligands) or by incorporation into the SELEX process.

As described above, because of their ability to selectively bind TGFβ2, the nucleic acid ligands to TGFβ2 described herein are useful as pharmaceuticals. This invention, therefore, also includes a method for treating TGFβ2-mediated pathological conditions by administration of a nucleic acid ligand capable of binding to TGFβ2.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

The following Examples are provided to explain and illustrate the present invention and are not intended to be limiting of the invention. Example 1 describes the various materials and experimental procedures used in Examples 2–5. Example 2 describes the isolation and characteristics of Nucleic Acid Ligands that bind human TGFβ2. Example 3 describes the Nucleic Acid Ligands isolated by the SELEX method using a biased round O library, the sequences of TGFβ2 Nucleic Acid Ligands isolated from the biased SELEX process, and the binding of Nucleic Acid Ligands isolated from the biased SELEX process. Example 4 describes substitutions of 2'-OH purines with 2'$OCH_3$ purines in NX22284 and NX222385. Example 5 describes the pharmacokinetic properties of NX22323. Example 6 describes 2'Omethyl modification of lead TGFβ1 truncate ligand CD70.

EXAMPLES

Example 1

Experimental Procedures

Materials

Monoclonal and polyclonal antibodies that recognize human TGFβ1, TGFβ2, or TGFβ3 were purchased from R&D Systems, Inc. (Minneapolis, Minn.). DNA oligonucleotides were purchased from Operon, Inc. (Alameda, Calif.) or Oligos, Etc. (Redding Center, Conn.). The BIAcore 2000 and IAsys plus instruments are products of Biacore, Inc. (Paramus, N.J.) and Affinity Sensors, Inc. (Cambridge, U. K.), respectively. Nitrocellulose filters and filtering manifolds were obtained from Millipore (Bedford, Mass.). Mink lung epithelial cells (#CCL64) were purchased from the American Type Culture Collection (Rockville, Md.). The cloning vectors pCR-Script and pUC9 were obtained in-house or from Stratagene, Inc. (La Jolla, Calif.) or Life Technologies, Inc. (Gaithersburg, Md.), respectively. E. coli strains were obtained from Stratagene. The QIAprep spin miniprep kit was from QIAgen, Inc. (Chatsworth, Calif.). The Big Dye sequencing kit and model 377 sequencer can be purchased from Applied Biosystems (Foster City, Calif.). T7 RNA polymerase and Thermus aquaticus DNA polymerase were purchased from Enzyco, Inc. (Denver, Colo.) and Perkin Elmer (Norwalk, Conn.), respectively. All restriction enzymes were purchased from New England Biolabs. E. coli RNase H was obtained from Boehringer Mannheim. All synthetic nucleic acids with a name that begins with "NX" were synthesized at NeXstar Pharmaceuticals, Inc. (Boulder, Colo.) using an ABI model 394 DNA/RNA synthesizer (Applied Biosystems). Yeast tRNA (type X-SA) and porcine intestinal mucosca-derived heparin (molecular weight 5000), were purchased from Sigma (St. Louis, Mo.) and Calbiochem (La Jolla, Calif.), respectively.

Preparation of Round 0 Nucleic Acid Library

The initial (round 0) library of ribonucleic acid molecules that was used to isolate TGFβ2 nucleic acid ligands was generated as follows. Two DNA oligonucleotides (40 N7 round 0 DNA template and 5'N7 primer) were annealed and filled in with Klenow to produce a 40 N7 round 0 DNA transcription template (Table 1). This template was transcribed using T7 RNA polymerase, 3 mM 2'-fluoro uridine and cytosine, 1 mM 2'-hydroxyl guanosine and adenine, and $\alpha^{32}$P-ATP as described in (Fitzwater and Polisky (1996) Meth. Enz. 267:275–301). This resulted in a round 0 40N7 nucleic acid pool with the following sequence which has 5' and 3' "fixed" regions and a 40 base long random sequence region:

5'-GGGAGGACGAUGCGG-40N-CAGACGACUCGCCCGA-3' (SEQ ID NO: 6) round 0 40N7 nucleic acid 5' fixed region random region 3' fixed region A=2'-OH A; C=2'-F C; G=2'-OH G; U=2'-F U   (Table 1)

Spot SELEX

Spot SELEX was performed as described in U.S. patent application Ser. No. 08/477,527, filed Jun. 7, 1995, entitled "High Affinity Nucleic Acid Ligands of Cytokines," now allowed, which is hereby incorporated by reference in its entirety, using nucleic acid that was internally labeled using $\alpha$-$^{32}$P ATP. The conditions and progress of this SELEX experiment are summarized in Table 3. Briefly, human TGFβ2 (or no protein) was applied to a 13 mm diameter nitrocellulose filter and allowed to absorb but not completely dry. The filter was incubated with RNA in Dulbecco's phosphate-buffered saline, 1 mM MgCl$_2$ and then washed as summarized in Table 3. Filter-bound and protein-bound nucleic acid was visualized and quantitated on an Instant Imager (Packard Instrument Co., Downers Grove, Ill.) and the protein-bound nucleic acid was eluted in 50% phenol, 4 M urea for 45 minutes at 65° C. Eluted nucleic acid was ethanol precipitated and then reverse transcribed using avian myeloblastosis virus reverse transcriptase and subjected to the polymerase chain reaction using 5'N7 and 3'N7 primers for 15 cycles. This resulting transcription template was transcribed with T7 RNA polymerase in the presence of 2'-fluoro pyrimidine nucleotides, 2'-OH purine ribonucleotides, and $\alpha^{32}$P-ATP, and carried to the next spot round. The pool from the first spot round was also transcribed as above in the absence of $\alpha$-$^{32}$P-ATP for use in round 2 of the surface plasmon resonance biosensor SELEX.

Surface Plasmon Resonance Biosensor SELEX

Rounds 2-spr through 9-spr were done using surface plasmon resonance biosensor technology on a BIAcore model 2000 instrument. For this experiment 1XDPBS, 1 mM MgCl$_2$, 0.005% P20 surfactant (cat#BR-1000-54, Biacore, hic., Piscataway, N.J.) was used as the running buffer. TGFβ2 was amine coupled onto a CM5 BIACORE chip (Biacore, Inc., Piscataway, N.J.) using the Biacore amine coupling kit (cat#BR-1000-50, Biacore, Inc., Piscataway, N.J.) per manufacturer's instructions. Briefly, TGFβ2 aliquots (3 µl, in 4 mM HCl at 100 µg/ml) were diluted in 30 µl of 10 mM CH$_3$COONa, pH 5.0 and injected on an EDC-NHS activated chip at 25° C., 5 µl/min, in different volumes to achieve different loading levels, as measured in response units (RU). Following coupling, the chip was washed with 3M NaCl for about 1.5 min at 10 µl/min. Under these experimental conditions, TGFβ2 loading of 15RU/µl could be achieved. TGFβ2 was loaded in flow cells 1, 2, and 3, while flow cell 4 was kept blank for control and background subtractions. Before use, the chip was tested for activity by testing binding of LAP and or soluble receptor III(R&D Systems, Minneapolis, Minn.) at 37° C. At the end of each test injections the chip was regenerated using 1 min wash with 10 mM NaOH. For SELEX rounds, RNA pools, generated by in vitro transcription without any labeled nucleotides, were in running buffer and were injected over the TGFβ2 loaded CM5 chips at 5 µl/min at 37° C. The concentration and volume of the RNA pools used at each round are as shown in Table 4. At each round the RNA pools were applied in 40 µl injections and each injection cycle was followed by a dissociation phase where the chip was washed with DPBS, 1 mM MgCl$_2$ at 20 µl/min while three 100 µl fractions (5 min each) were collected. Following the last injection-dissociation cycle, the chip was treated with 0.25% SDS and the eluted RNA was collected as the final fraction. The third fractions of each injection cycle and the SDS elution were pooled and amplified by RT/PCR to generate the template pool for the next SELEX round.

Resonant Mirror Optical Biosensor SELEX

Rounds 10-rm through 13-rm were done using an IASYS plus resonant mirror optical biosensor instrument. Round 9-spr from the surface plasmon resonance SELEX was used as the starting material. For this experiment, 1XDPBS, 1 mM MgCl$_2$, 0.005% P20 surfactant (cat#BR-1000-54, Biacore, Inc., Piscataway, N.J.) were used as the running buffer. TGFβ2 was amine coupled onto a CMD IASYS cuvette (Affinity Sensors, Cambridge, UK) according to the manufacturer's protocol. Briefly, the CMD cuvette was activated with 0.2 M EDC, 0.05 M NHS for 10 minutes, and TGFβ2 was coupled by injection 35 µl of 0.4 µM TGFβ2, 10 mM CH$_3$COONa, pH 5.5 in 35 µl of 10 mM CH$_3$COONa, pH 5.5. The coupling reaction was at 25° C. for about 10 min and resulted in about 2,000 Arcsec of signal. Unreacted sites were capped by exposing the cuvette in 1M ethanolamine for 1–2 min. Following coupling and capping the cuvette was exposed to 3M NaCl for 1–2 min and was ready for use. The cuvettes were routinely tested for activity by measuring binding of LAP and or soluble receptor III (R&D Systems, Minneapolis, Minn.) at 37° C. At the end of each test injection the chip was regenerated using 1 min wash with 50 mM NaCO$_3$. For SELEX rounds, RNA pools, generated by in vitro transcription without any labeled nucleotides, were in running buffer. They were injected in the TGFβ2 loaded CMD cuvette and incubated for 27–60 min (Table 6) under 100% steering at 37° C. Following binding, the RNA was replaced with buffer and bound RNA was observed to dissociate from the cuvette surface. Dissociation was allowed for 30–150 min (Table 6) at 37° C. while the buffer was exchanged several times to avoid evaporation. Following dissociation, the remaining RNA was eluded with H$_2$O or 0.25% SDS and the RNA was amplified as above and carried to the next SELEX round.

SELEX Using Filter Partitioning and Polyanion Competition

For rounds 9b through 22a, SELEX using filter partitioning was performed essentially as described in (Fitzwater and Polisky (1996) Meth. Enz. 267:275–301) except that 1) heparin or yeast tRNA was included to compete off ligands that bound nonspecifically, 2) the binding buffer was HBSMCK (50 mM HEPES, pH 7.4, 140 mM NaCl, 1 mM MgCl$_2$, 1 mM CaCl$_2$, 3 mM KCl), 3) extensive efforts were undertaken to reduce filter binding sequences (preadsorbtion of nucleic acid onto filters after elution and transcription, blocking of filters with tRNA and bovine serum albumin prior to partitioning, addition of 0.5 M urea to the wash buffer) and 4) the transcripts were initiated with a 5:1 molar mixture of guanosine: 2'-fluoro-nucleotides. Initiation with guanosine allows nucleic acids to be used in SELEX or bioactivity assays without radiolabeling and alleviates a phosphatase step if the nucleic acid is to be 5'-end radiolabeled for binding studies.

Round 8-spr from the surface plasmon resonance SELEX was used as the starting material. From rounds 9b to 14i, the SELEX process was performed using protein-excess conditions. The concentrations of nucleic acid and protein were equimolar in round 15c. Nucleic acid-excess conditions were used from rounds 16a to 22a (Table 2). Competitors (yeast tRNA and heparin) were used from rounds 9b to 14i. Filters were washed with 10–15 ml HBSMCK buffer from rounds 9b to 12d and increasing amounts (5–50 ml) of HBSMCK, 0.5 M urea from rounds 13i to 22a.

Sequencing of Nucleic Acid Ligand Pools

Nucleic acid pools were sequenced as described in (Fitzwater and Polisky (1996) Meth. Enz. 267:275–301).

Screening Nucleic Acid Ligand Pools Using Ligand-specific Reverse Transcription-polymerase Chain Reactions Nucleic acids from the various pools was reverse transcribed with clone-"specific" primers (ML-85 for ligand 14i-1 and ML-81 for ligand 21a-21) for 12, 15 or 18 cycles. Mixtures of pure nucleic acid ligands and round 0 40N7 nucleic acid that contained 10%, 3%, 1%, 0.3%, or 0.1% ligand were processed in the same manner and served to quantitate signals from RT-PCR of the nucleic acid pools.

Cloning, Screening, and Sequencing of Nucleic Acid Ligands

Nucleic acid ligands were cloned using two methods. In one method the ligands were directly cloned into pCR-Script according to the manufacturer's instructions and transformed into *E. coli* strain XL-1 Blue MRF' Kan. In the other method the double-stranded DNA transcription template was amplified by PCR using primers ML-34 and ML-78, digested with BamHI and EcoRI restriction enzymes, and cloned into BamHI and EcoRI-digested pUC9. The ligation was transformed into *E. coli* strain DH5α. Colonies were selected on ampicillin plates and screened for inserts by PCR using vector-specific primers (RSP and FSP2). Typically 90%–100% of the clones had inserts. Some colonies or nucleic acid pools were also screened using 14i-1, 21a-4, or 21a-21 ligand-specific primers (ML-79, ML-81, and ML-85, respectively) in an attempt to identify clones that were different from those already isolated.

Plasmid minipreps from the transformants were prepared using the QIAprep spin miniprep kit (QIAGEN, Inc., Valencia, Calif.) or PERFECT prep plasmid DNA kit (5'3', Inc., Boulder, Colo.). Sequencing reactions were performed with the Big Dye kit and a sequencing primer (RSP2). The sequencing products were analyzed on an ABI model 377 sequencer.

Nucleic Acid Ligand Boundaries

The boundaries (5' and 3' end) of the smallest ligand that can bind TGFβ2 was determined essentially as described in (Fitzwater and Polisky (1996) Meth. Enz. 267:275–301). The protein concentrations used were 0, 1 nM, and 10 nM and the nucleic acid/protein ratio was 1. The binding buffer used in this experiment was HBSMC, 0.01% HSA. Binding reactions were incubated at 37° C. for 30 min, filtered through 0.45 μm, nitrocellulose filters (15 mm), and then washed with 15 ml HBSMC. The RNA was recovered by phenol-urea extraction, eluted RNA was ethanol precipitated in the presence of glycogen, resuspended in H$_2$O, supplemented with equal volume 2×formamide dye, and analyzed on 8% acrylamide, 8M urea sequencing gels. Truncated RNAs that were bound to TGFβ2 were visualized and developed on a FUJIX BAS1000 phosporimager (FUJI Medical Systems, USA).

Nucleic Acid Ligand Truncation

Truncated versions of full length nucleic acid ligands were generated in three ways. In one method, *E. coli* RNase H and hybrid 2'-OCH$_3$RNA/DNA oligonucleotides (5'N7 cleave, 3'N7 cleave; Table 1) were used to cleave nucleic acids at a specific site. Truncation SELEX is described in U.S. patent application Ser. No. 09/275,850, filed Mar. 24, 1999, entitled "The Truncation SELEX Method," which is hereby incorporated by reference in its entirety. In a second method, overlapping DNA oligonucleotides encoding the desired ligand sequence were annealed, extended by Klenow DNA polymerase, and then transcribed. In a third method, ligands were chemically synthesized with the desired sequence.

Binding of Nucleic Acid Ligands to Human TGFβ's

The binding activity of individual ligands was determined by measuring the equilibrium dissociation constants using nitrocellulose partitioning of labeled RNA as a function of protein concentration. RNA was body-labeled or guanylated and then 5'-end labeled with γ-$^{32}$P ATP and T4 polynucleotide kinase. Binding reactions were set at various protein concentrations (typically varied in either 3-fold or 10-fold increments) while maintaining the labeled RNA concentration constant at less than 0.1 nM, and incubated at 37° C. for 10 min. Protein-RNA complexes were partitioned away from uncomplexed RNA, by filtering the binding reactions through a nitrocellulose/cellulose acetated mixed matrix (0.45 μm pore size filter disks, type HA; Millipore, Co., Bedford, Mass.). For filtration, the filters were placed onto a vacuum manifold (12-well, Millipore, or 96-well BRL) and wetted by aspirating 1–5 ml of binding buffer. The binding reactions were aspirated through the filters, washed with 1–5 ml of binding buffer and counted in a scintillation counter (Beckmann).

To obtain the monophasic equilibrium dissociation constants of RNA ligands to hTGFβ2 the binding reaction:

K$_D$

R:P→R+P

R=RNA

P=Protein

K$_D$=dissociation constant is converted into an equation for the fraction of RNA bound at equilibrium:

q=(f/2R$_T$)(P$_T$+R$_T$+K$_D$−((P$_T$+R$_T$+K$_D$)$^2$−4P$_T$R$_T$)$^{1/2}$)

q=fraction of RNA bound

P$_T$=total protein concentration

R$_T$=total RNA concentration f=retention efficiency of RNA-protein complexes

The average retention efficiency for RNA-TGFb2 complexes on nitrocellulose filters is 0.3–0.8. Kd values were obtained by least square fitting of the data points using the software Kaleidagraph (Synergy Software, Reading, Pa.).

Competition Between Ligands $^{32}$P-labeled test ligands at a concentration of 1 nM were mixed with increasing concentrations of unlabeled NX22283 (SEQ ID NO: 114). Then, an amount of TGFβ2 estimated to be near the Kd of the test ligands was added (1 nM for NX22283, 1 nM for 21a-21, 3 nM for 21a-4, and 10 nM for 14i-1). The reactions were incubated, filtered, washed, and counted as for a binding reaction.

Off-rate of NX22283

1 nM $^{32}$P-labeled NX22283 was mixed with 10 nM TGFβ2, incubated for 5 minutes to allow the protein to bind to the nucleic acid, and then a 1000-fold excess (1 μM) of unlabeled NX22283 was added. At various time points the reactions were filtered and washed to measure the amount of $^{32}$P-labeled NX22283 that remained bound.

Biased SELEX

A library of sequences was constructed based on the sequence of the 34-mer truncate (NX22284) of nucleic acid ligand 21a-21. The sequence of the DNA template (34N7.21a-21 (SEQ ID NO: 7)) is shown in Table 1. The randomized region is 34 bases long. At each position the randomized region consists of 62.5% of the NX22284 sequence and 12.5% of the other 3 nucleotides. Thus the randomized region is mutagenized at each position (37.5%) but at the same time is biased toward the sequence of NX22284. The fixed regions (5'N7, 3'N7) were the same as used for the primary SELEXs.

To generate 34N7.21a-21 round 0 nucleic acid, the DNA template was amplified by PCR using the 5'N7 (SEQ ID NO: 2) and 3'N7 (SEQ ID NO: 3) primers (Table 1). This PCR product was transcribed as described above in the filter partitioning SELEX section. This resulted in a 34N7.21a-21 round 0 nucleic acid pool with the sequence shown in Table 1 (SEQ ID NO: 10).

Filter partitioning as described above and in Fitzwater and Polisky (1996) (Meth. Enz. 267:275–301) with no competitors was used to enrich nucleic acids ligands that bound to human TGFβ2 the best. The protein concentration was reduced from ~150–300 nM to 50 pM. The nucleic acid concentration was reduced from 1 μM to 1 nM. The nucleic acicd/protein ratio ranged from 0.25 to 125. The round 5a pool of ligands was cloned into pUC9 and sequenced as described above.

Bioactivity of TGFβ2 Nucleic Acid Ligands

The bioactivity of TGFβ2 nucleic acid ligands was measured with mink lung epithelial cells. Proliferation of these cells is inhibited by TGFβ2. Human TGFβ2 was titrated on the cells and $^3$H-thymidine incorporation was measured. The point at which $^3$H-thymidine incorporation by the cells was inhibited by 90–100% was determined (typically 1–4 pM). This inhibitory amount of TGFβ2 along with varying amounts of nucleic acid ligand (typically 0.3 or 1 nM to 1 or 3 μM, in 3 fold increments) was used. Typically, cells were plated at 10E5/ml in 96-well plates in 100 μl MEM, 10 mM HEPES pH 7.4, 0.2% FBS. Following a 4 hr incubation at 37° C., when cells were well attached to the well surface, TGFβ2 was added at 1–4 pM with or without nucleic acid ligands as follows: the ligands were diluted across the 96 well plate in 3-fold dilution steps and then TGFβ2 was added at 1–4 pM to all wells except controls. The cells were incubated for 16–18 hours prior to addition of $^3$H-thymidine, and then incubation was continued for 20 additional hours following $^3$H-thymidine addition at 0.25 μCi per well. After incubation, the cells were lysed with 1% Triton X-100 and harvested onto GF/B filter plates in a Packard 96 well plate harvester, and $^3$H-thymidine incorporation in cellular DNA was quantitated by scintillation counting in MicroScint (Packard, Mariden, Conn.) in a Packard Top-Count. Data were plotted as % of maximum $^3$H-thymidine incorporation vs RNA concentration, and were fitted by the software Kaleidagraph (Synergy Software, Reading, Pa.) to the equation m3*(m0+m1+(m2)-((m0+m1+(m2))*(m0+m1+(m2))-4*(m0)*((m2)))^ 0.5)/(2*(m2)); where m0 is the concentration of competitor RNA; m1 is the IC50, m2 is the concentration of TGFβ2, and m3 is the plateau value of the fraction of maximum $^3$H-thymidine incorporation. $K_i$ values were determined from $IC_{50}$ values according to the equation $K_i = IC_{50}/(1+([T]/K_{dT})$, where [T] is the molar concentration of TGFβ2 present in the assay and $K_{dT}$ is the concentration of TGFβ2 causing 50% inhibition of MLEC proliferation as determined by TGFβ2 titration experiments. This assay was also used to determine the isotype specificity of RNA ligands where the three TGFβ isotypes were independently used as inhibitors of MLEC replication.

Pharmacokinetic Properties of NX22323

The pharmacokinetic properties of TGFβ2 ligand NX22323 were determined in Sprague-Dawley rats. NX22323 was suspended in sterile PBS and stored at ≦−20° C. Prior to animal dosing NX22323 was diluted with sterile PBS, to a final concentration of 0.925 mg/ml (18 μM, based on the oligonucleotide molecular weight and the ultraviolet absorption at 260 nm with an extinction coefficient of 0.037 mg of oligo/ml). Sprague-Dawley rats (n=2) were administered a single dose of NX22323 by intravenous bolus injection through the tail vein. Blood samples (approximately 400 μL) were obtained by venipuncture under isofluorane anesthesia and placed in EDTA-containing tubes. The EDTA-treated blood samples were immediately processed by centrifugation to obtain plasma and stored frozen ≦−20° C. Time points for blood sample collection ranged from 5 to 2880 minutes.

Standards and quality control samples prepared in blank rat plasma and plasma samples were analyzed by a double hybridization assay. To prepare plasma samples for hybridization analysis, 25 μL of plasma sample (or a dilution in plasma of the sample) was added to 100 μL of 4×SSC, 0.5% sarkosyl. A 25 μL aliquot was then mixed with 25 μL of 4×SSC, 0.5% sarkosyl containing 24 μM capture oligonucleotide conjugated to magnetic beads and 28 μM detect oligonucleotide conjugated to biotin in a covered 96-well microtiter plates. The mixture was allowed to incubate at 45° C. for 1 hour. Unbound oligonucleotide was removed and 0.1 ng streptavidin alkaline phosphatase/μL NTT Buffer (0.8 M NaCl, 20 mM Tris pH 7.5, 0.5% Tween 20) added to each well followed by a 30 minute incubation at room temperature. The streptavidin alkaline phosphatase was removed and the plate was washed twice with 200 μl NTT Buffer. The NTT Buffer was removed and replaced with 50 μL DEA buffer (0.02% sodium azide, 1 mM $MgCl_2$, 1% diethanolamine (Tropix, Inc., Bedford, Mass.), pH 10). Then 34 μL/ml 25 mM chemiluminescent substrate for alkaline phosphatase (Tropix, Inc., Bedford, Mass.), and 20% Sapphire chemiluminescence amplifier (Tropix, Inc., Bedford, Mass.) in DEA buffer (50 μL/well) was added. The plate was incubated for 20 minutes at room temperature and read on a luminometer. A standard curve of NX22323 was fit using a variable slope sigmoidal dose response non linear regression equation (PRISM, version 2.00, GraphPad, San Diego, Calif.). Sample and quality control concentrations were extrapolated from the standard curve and corrected for dilution.

The average plasma concentration at each time point was calculated and utilized in the pharmacokinetic analysis. Both noncompartmental and compartmental pharmacokinetic analysis were carried out using WinNonlin version 1.5 (Scientific Consulting, Inc.). In the noncompartmental analysis, the following parameters were calculated; the maximum concentration extrapolated at zero time (Cmax), the area under the curve from zero to the last time point (AUClast), the area under the curve from zero to infinite time (AUCINF), the terminal phase half life (Beta t½), the clearance rate (Cl), the mean residence time calculated from zero to infinite time (MRTINF), the volume of distribution at steady state (Vss), and the volume of distribution during elimination (Vz). In the case of compartmental analysis, the following parameters were calculated based on the minimum number of monoexpronetial equations to adequately fit the data: the maximum concentration extrapolated at zero time (Cmax), the area under the curve from zero to infinite time (AUCINF), the distribution phase half life (Alpha t½), terminal phase half life (Beta t½), the exponential constant for the distribution phase (A), the exponential constant for the terminal phase (B), the clearance rate (Cl), the mean residence time calculated from zero to infinite time (MRTINF), and the volume of distribution at steady state (Vss).

Example 2

Isolation of Nucleic Acid Ligands That Bind Human TGFβ2

Several SELEX experiments on TGFβ2 have been attempted as summarized in FIG. 1. Several partitioning methods were applied at various stages of the SELEX progress including standard filtration through nitrocellulose, spot, surface plasmon resonance biosensor (BIAcore), resonant mirror biosensor (Iasys), polystyrene beads, and polyacrylamide gel shift. The combination of spot SELEX, surface plasmon resonance biosensor SELEX, and filter partitioning SELEX (with competitors) described here had the best overall improvement in affinity (~>1000 fold) and thus is described in detail. In addition, a branch of this SELEX that utilized resonant mirror biosensor technology is also described.

Spot SELEX Conditions

Spot SELEX was chosen to initiate the SELEX process on human TGFβ2 because it would allow a large amount of protein and nucleic acid to interact. The conditions used are shown in Table 3. The results of round 1 were acceptable. The background was very low and the signal to noise ratio was 5. At this point the population from the first round was used for the surface plasmon SELEX in addition to continuing with the spot partition method. We completed 10 rounds of spot SELEX as summarized in Table 3 and observed a modest improvement in the affinity of the pool of about 30 fold. These pools were not analyzed further.

Surface Plasmon Resonance Biosensor (spr) SELEX

Surface plasmon resonance biosensors were chosen as a partitioning medium because they provide very low background nucleic acid binding to the sensor, so that higher degrees of enrichment can be obtained. In addition binding and elution of nucleic acid can be monitored and quantitated in real time.

Figure 2A:
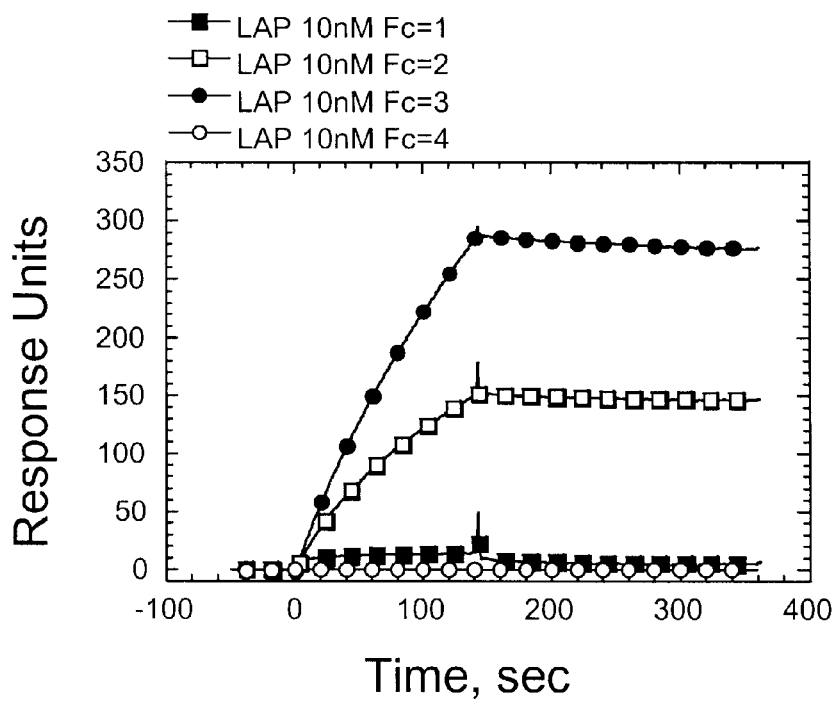
FIG. 2 shows activity of TGFβ2 following amine coupling on a BIAcore carboxymethylcellulose (CM5) chip. A CM5 chip was loaded with TGFβ2 using NHS-EDC coupling as described in the Materials and methods at about 18, 718, and 1692 response units for flow cell (FC) 1, 2, and 3, respectively. FC-4 was left blank as a control and was used to normalize the signals from the other FCs. The chip was then exposed to 10 nM of either (FIG. 2A) latency associated peptide (LAP) or (FIG. 2B) TGFβ soluble receptor III (sRIII at 20 μl/min in binding buffer. Data were collected for an association and a dissociation phase as shown. The signal from FC-4 was subtracted from the other FCs.
Figure 2B:
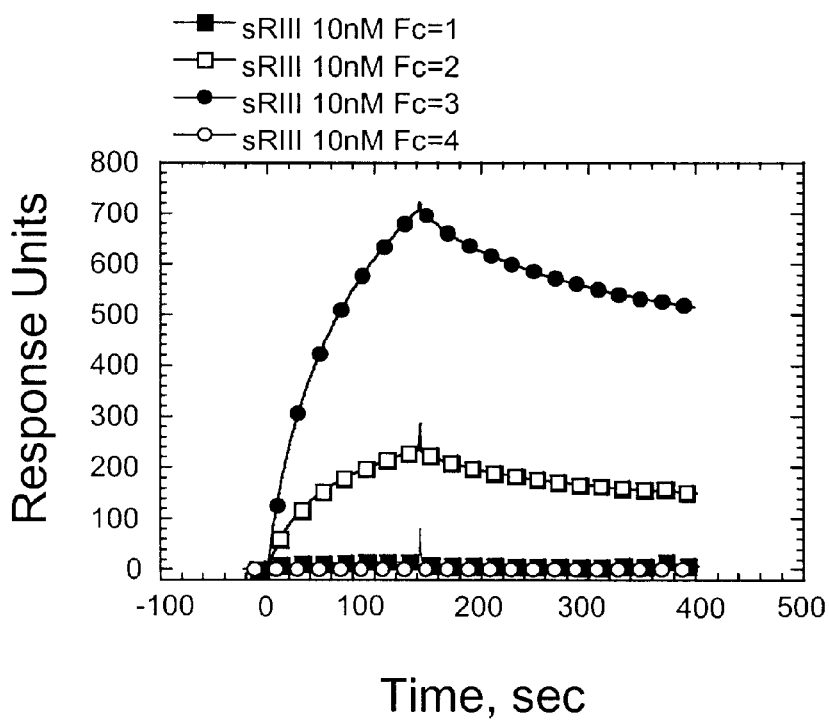
Figure 3:
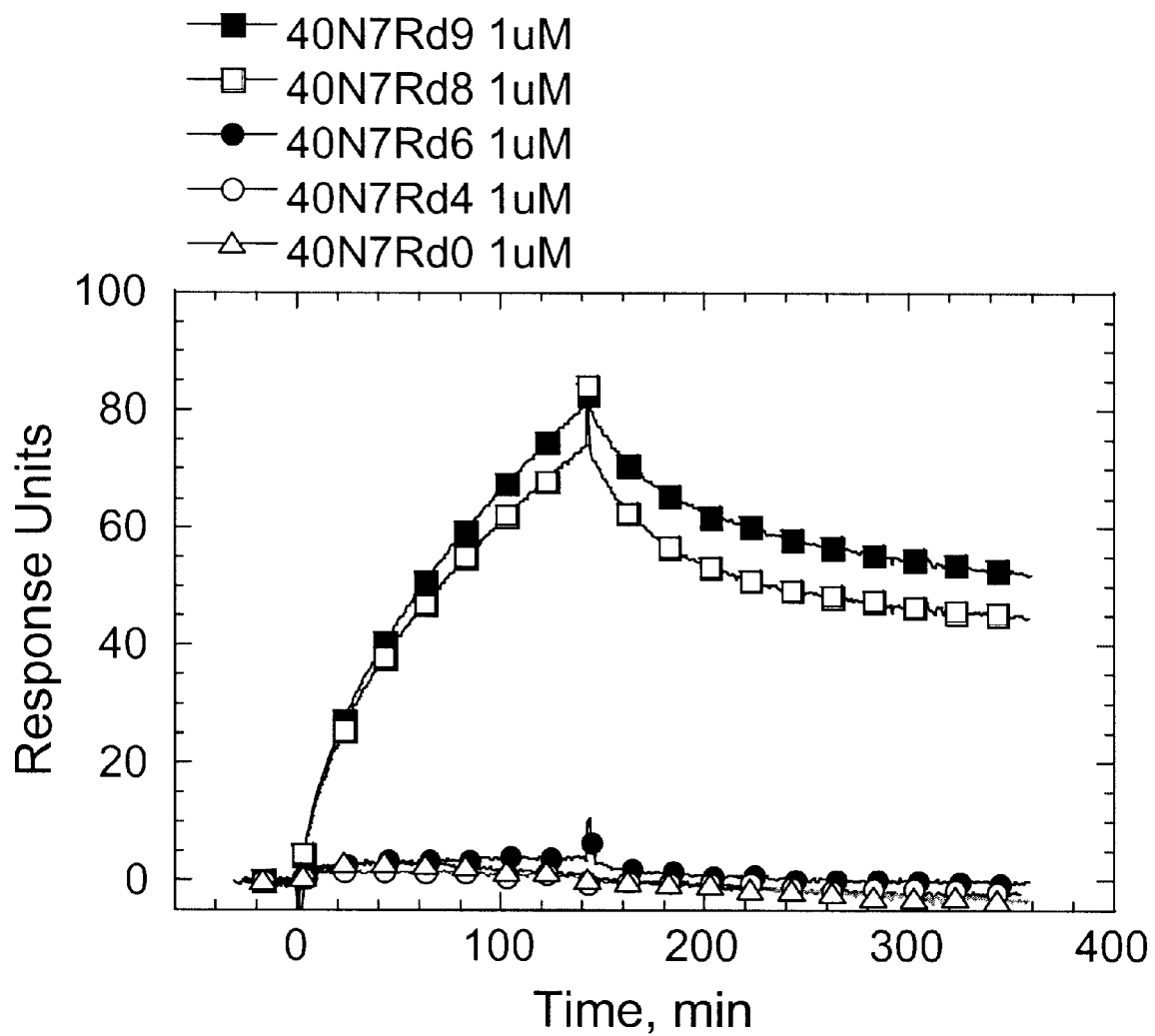
FIG. 3 shows affinity improvement during the spr SELEX. A CM5 chip was loaded with TGFβ2 using NHS-EDC coupling as described in the Materials and methods at about 18, 718, and 1692 response units for flow cell (FC) 1, 2, and 3, respectively. FC-4 was left blank as a control and was used to normalize the signals from the other FCs. The chip was then exposed to 1 μM of RNA pools from the SELEX rounds (Rd) as shown at 20 μl/min in binding buffer. Data were collected for an association and a dissociation phase as shown. The signal from FC-4 was subtracted from the other FCs.
Figure 4:
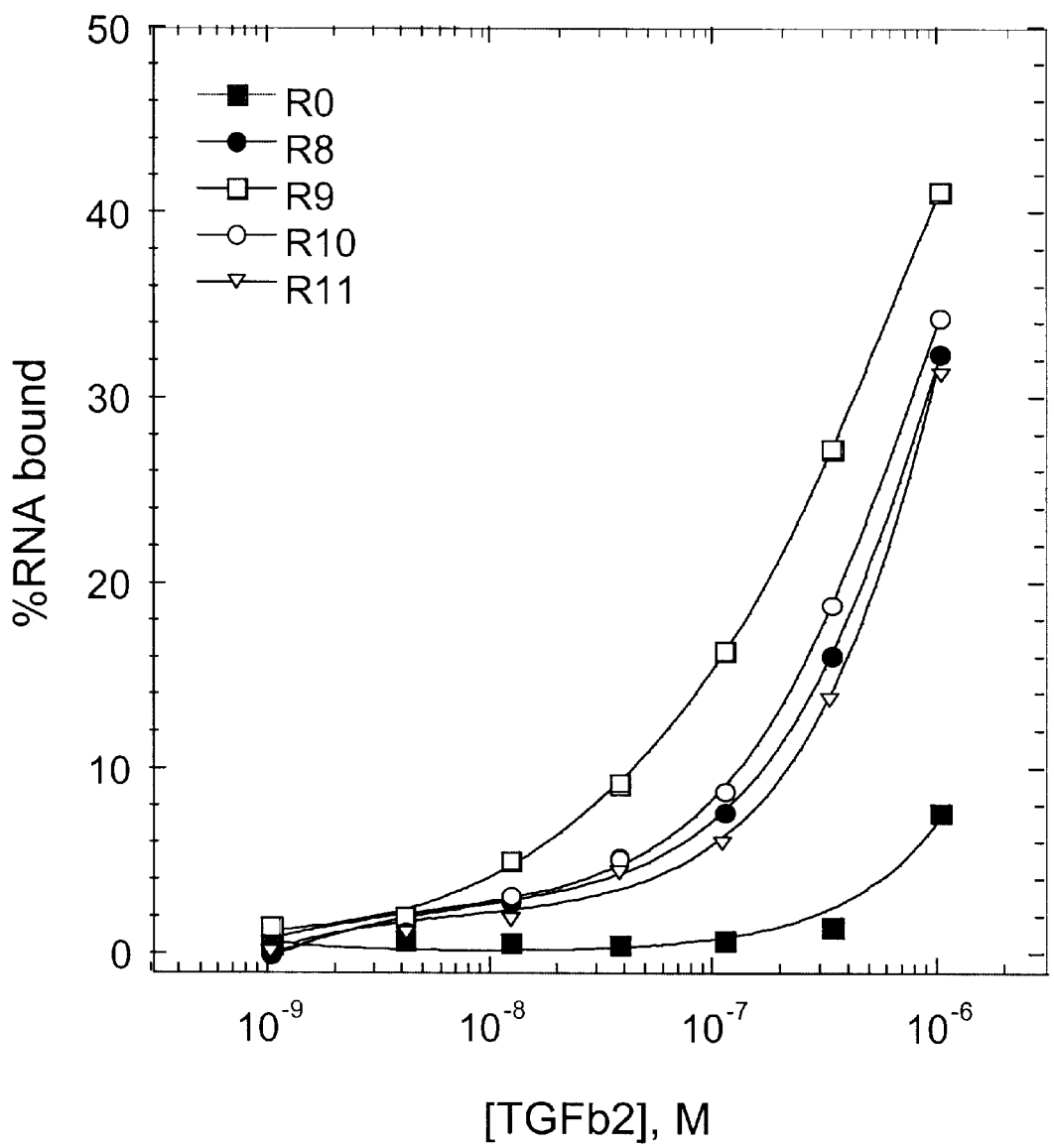
FIG. 4 shows Nitrocellulose filter binding curves with pools from the spr SELEX. High specific activity internally labeled RNA was used from rounds (R) as shown. Labeled RNA was incubated with various concentrations of TGFβ2 in the presence of ~100,000 fold molar excess unlabelled tRNA. Bound RNA was partitioned by nitrocellulose filtration and quantitated. Data were analyzed as described in the Materials and Methods.

TGFβ2 was coupled to a BIAcore biosensor using amine coupling chemistry. TGFβ2 coupled in this manner binds latency-associated protein, and recombinant soluble TGFβ receptors. FIG. 2 shows typical sensograms obtained with LAP and recombinant sRIII where we observed $k_{on}$ and $k_{off}$ rates indicative of avid binding. During this SELEX experiment as summarized in Table 4, a binding signal was first observed on the biosensor in round 6, increased up to round 9, and then decreased in rounds 10 and 11. FIG. 3 shows sensograms with 0, 4-spr, 6-spr, 8-spr, and 9-spr. FIG. 4 shows typical filter binding curves, in the presence and absence of competitor tRNA, with representative pools from the spr SELEX and from these data it seems that round 9 binds in a biphasic manner with a high affinity and low affinity $K_d$ of 30 and 160 nM, respectively.

In bioactivity assays the $K_i$ of the round 0 pool was about 2.6 μM and the $K_i$ of the round 9-spr pool was about 711 nM (see below). Sequence analysis of representative pools indicated that such pools maintained significant complexity up to round 8 while after round 9 such pools were strongly biased towards a single sequence.

Round 8-spr was cloned and sequenced. A total of 69 clones representing 51 different sequences were analyzed. Four sequences (#8.2, 8.3, 8.9, and 8.48; see Table 5) were represented more than once and accounted for 21 of the 69 clones. All four of these sequences bound TGFβ2 and were 2 or 3 base variants of a clone (14i-1) isolated from the filter SELEX (see below). Twenty three other sequences were nonbinding or filter-binding sequences (see Table 5) and 25 clones were not tested for binding.

Resonant Mirror (rm) Optical Biosensor SELEX

Since the affinity of nucleic acid pools selected on the surface plasmon resonance biosensor peaked at round 9-spr, resonant mirror (rm) optical biosensor technology was tested to determine if it could advance the affinity of nucleic acid ligands any further. Resonant mirror optical biosensor technology offers many of the same advantage as surface plasmon biosensor technology, but in addition the binding is done in a cuvette under equilibrium conditions rather than over the surface of a chip under flow conditions. Within the cuvette the binding can be extended for long time periods. Therefore the nucleic acid/protein binding reaction can be more stringent and selective.

For resonant mirror SELEX, TGFβ2 was coupled to two biosensor cuvettes using amine coupling chemistry. In one cuvette the TGFβ2 was inactivated by SDS denaturation and this cuvette served to assess background. The other cuvette containing active TGFβ2 was used for the SELEX. Beginning with round 9-spr, five rounds were done using resonant mirror optical biosensor technology. The conditions used for and the results of the resonant mirror SELEX are shown in Table 6.

Figure 5:
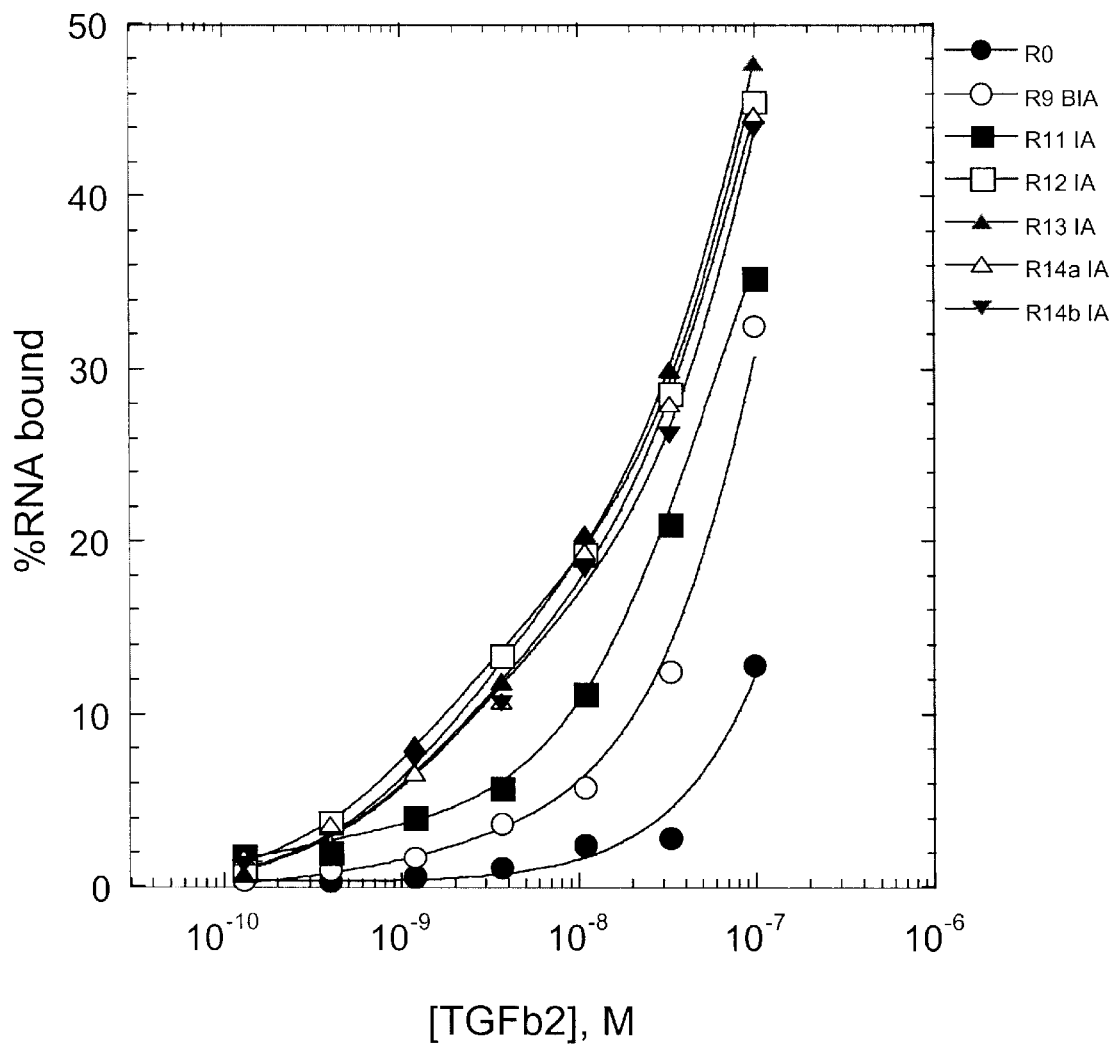
FIG. 5 shows nitrocellulose filter binding curves with various pools. High specific activity internally labeled RNA was used from rounds (R) as shown. Labeled RNA was incubated with various concentrations of TGFβ2 (no competitor tRNA was used). Bound RNA was partitioned by nitrocellulose filtration and quantitated. Data were analyzed as described in the Materials and Methods.

Biosensor signals were observed for each round. The binding of the nucleic acid pools from rounds 10-rm to 12-rm was assessed (Table 6; FIG. 5). The pool $K_d$ improved modestly up to round 12-rm with no further improvement in the subsequent rounds. The round 12-rm pool binds biphasically with high and low affinity Kd of ~2 nM and ~150 nM, respectively.

In bioactivity assays the $K_i$ of the round 13-rm pool was about 505 nM. Round 13-rm was chosen for subcloning and sequence analysis. Of 15 clones that were sequenced, all 15 (Table 7) were 1 to 5 base variants of a clone (14i-1) which was originally isolated from the filter SELEX (see below).

Filter Partitioning SELEX

Round 8-spr was used as the starting material for a filter SELEX. The properties of round 8-spr were studied and it was found that 1) a significant fraction bound to a nitrocellulose filter (10%), 2) significant nucleic acid binding (defined here as signal/noise >2) to TGFβ2 was not detectable using nucleic acid-excess conditions, and 3) in the presence or absence of polyanionic competitors there was a significant decrease in the binding of round 0, but not round 8-spr to TGFβ2. These findings had implications that are addressed below.

Use of a Competitor.

The binding of round 8-spr nucleic acid to TGFβ2 in the presence of a polyanionic competitor (yeast tRNA) was studied at various ratios of competitor to nucleic acid. It was found that a 75,000 fold excess of tRNA over round 8-spr nucleic acid resulted in 50% inhibition of binding, whereas a 6,000 fold excess of tRNA over the round 0 nucleic acid pool resulted in 50% inhibition of binding. Heparin also competed with RNA for binding to TGFβ2 but about 10-fold more heparin was needed to inhibit RNA binding to TGFβ2 to the same degree as that observed using tRNA. By including a 100,000-fold excess of yeast tRNA over RNA in a TGFβ2/RNA binding experiment, a 100-fold difference in binding between round 0 and round 8-spr was detected, whereas a 3-fold difference was observed in the absence of any competitor. Thus in the presence of an appropriate amount of competitor, the binding of selected nucleic acid pools is unaffected, whereas the binding of round 0 nucleic acid is reduced substantially. When competitors are not included in studying the binding of TGFβ2 to nucleic acid the affinity of nucleic acids selected using the SELEX process can be grossly underestimated. In this regard TGFβ2 is similar to other "professional" nucleic acid binding proteins (e.g., restriction enzymes, polymerases, transcription factors, etc.), in that it possesses both a low affinity, nonspecific and a high affinity, specific nucleic acid binding activity. The difference between these 2 binding modes can be revealed in the presence of competitors. Competitors are often used in the study of transcription factors. For example, it can be difficult to detect specific binding of a crude extract containing a transcription factor to oligonucleotides representing their cognate site in gel-shift experiments, unless a competitor, such as poly [dI-dC]•poly [dI-dC], is included in the binding reaction.

Nonspecific binding can involve the binding of multiple proteins per nucleic acid, often at low affinity sites, giving a false appearance of high affinity. A protein can bind at multiple sites on a nucleic acid or protein aggregates may form on a single protein bound to a nucleic acid. TGFβ2 is well known to be "sticky". In the absence of a competitor of nonspecific interactions, TGFβ2 may form large networks and complexes of nucleic acid and protein involving primarily nonspecific interactions. Gel shift analysis of TGFβ2, in the absence of competitor, supports these ideas because TGFβ2 does not form distinct (one to one) complexes with nucleic acid in gels, but instead either remains in the well at the top of a gel or forms smears that may represent large heterogeneous nucleic acid/protein complexes.

Besides the implications for doing binding curves, the nucleic acid-binding properties of TGFβ2 may have implications for SELEX. For example the high level of nonspecific binding of nucleic acid by TGFβ2 may have interfered with previous SELEXs by obscuring specific interactions or preventing the isolation of nucleic acid/protein complexes that involved only specific binding interactions. That is, if mixtures of specific and nonspecific nucleic acid interactions exist in nucleic acid/TGFβ2 complexes that form, then the selection for specific interactions may be difficult, if the nonspecific interactions are not eliminated. Lack of progress in some previous SELEX experiments may have been due to efficient competition by the large excess ($>10^{12-10^{14}}$) of low affinity nucleic acids that contain nonspecific binding sites with a smaller number (~10–1000) of high affinity nucleic acids that contain specific binding sites, especially in early rounds of SELEX.

Use of Protein-excess or Nucleic Acid-excess Conditions

Given the discussion above, a question arises as to which type of SELEX condition is better for a protein such as TGFβ2, protein-excess or nucleic acid-excess. Protein-excess conditions may tend to encourage nonspecific interactions. However as long as the competitor/nucleic acid ratio is high enough to eliminate enough nonspecific interactions, but retain specific interactions, this may not be an issue. One advantage to using protein excess is the bound to backround ratios are better and backround is lower, which would results in better levels of enrichment.

Nucleic acid-excess conditions may not discourage nonspecific interactions because within nucleic acid pools used for SELEX the ratio of nonspecific to specific binding nucleic acids (which is what is most important) would be the same no matter what the nucleic acid concentration is. In addition nucleic acid-excess would reduce the competitor/ nucleic acid ratio which would tend to increase nonspecific interactions. As discussed above the ratio of tRNA to nucleic acid must be at least 100,000 in early round of the filter SELEX in order for affinity enrichment to be efficient. This can be technically difficult in early rounds of SELEX when the nucleic acid concentration is typically higher. One advantage to using excess nucleic acid is that more members of a given sequence would be represented in a pool. However if there had been enough enrichment (e.g., using a method such as surface plasmon resonance SELEX) prior to filter SELEX there will probably be multiple representatives of a given sequence and this would not be an issue.

Filter SELEX Conditions

The conditions used at each round of the filter SELEX are shown in Table 15. Multiple conditions (up to 12) were used in each round varying nucleic acid/protein ratios, competitor/nucleic acid ratios, filter washing buffers, and filter washing volumes. Typically conditions that resulted in the lowest background (<1%) and a significant bound/ background ratio (>2) were processed for the next round. Only data for SELEX rounds that were used in the next round are shown in Table 15.

The SELEX began by using an amount of tRNA competitor (100,000-fold excess) that was determined in the SELEX reaction to inhibit binding of round 8-spr to TGFβ2 by about 60%. SELEX reactions with competitor were done for round 9b through 14i. The inclusion of tRNA in round 9 also dramatically reduced binding of round 8-spr nucleic acid to nitrocellulose filters from ~10–15% to ~1%. The higher the "background" binding is in a SELEX reaction, the lower the maximum possible enrichment. Thus inclusion of tRNA in the early rounds of the filter SELEX may have had a dual benefit. It not only may have eliminated nonspecific binding of TGFβ2 to nucleic acid, but also allowed more enrichment by reducing background. At round 15c lower affinity competitors were no longer effective at reducing binding of nucleic acid and were not used. This is presumably because the nucleic acid pool bound TGFβ2 with adequate specificity and affinity. Therefore from round 16 to 22, the presumed specific nucleic acids were allowed to compete with each other by using more traditional nucleic acid-excess conditions.

The background increased to unacceptable levels in rounds 15c and 16a. Gel shift partitioning was investigated as an alternative partitioning procedure at this point but did not work. By modifying the washing conditions the background was reduced to 0.2% in round 17a. After round 18b it was possible to do SELEX rounds at protein concentrations below 1 nM and under nucleic acid-excess conditions. It was also found that nucleic acid concentrations above 1–5 nM also helped to reduce background in some rounds.

In summary, during the filter SELEX, the concentration of the protein was reduced 30,000-fold, from 300 nM in round 9b to 10 pM in round 22a. The background binding to filters was reduced from 10% to 0.1%. Nucleic acid pools that bound to TGFβ2 only when protein-excess conditions (~100 protein/1 nucleic acid) were used were selected to bind under high nucleic acid/protein (>100/1) or competitor/ nucleic acid ($>10^7/1$)-excess conditions.

Binding of Nucleic Acid Pools from Filter SELEX

The binding of TGFβ2 to selected nucleic acid pools improved steadily, but slowly and erratically. There was an improvement in the binding of round 10 b ($K_d$=~100 nM) compared to the starting pool (round 8-spr; $K_d$=~500 nM). The affinity of round 11a was the same as 10b and that of round 12d improved modestly to ~40 nM. Rounds 13i and 15c bound TGFβ2 approximately the same ($K_d$=~30), while round 14i may have bound worse ($K_d$=~75). Round 16a nucleic acid ($K_d$=~10 nM) bound slightly better than round 15c. There was ~2-fold improvement in affinity of the nucleic acid pool from rounds 16a to 17a ($K_d$=~5 nM). The $K_d$ of round 18a nucleic acid (~5 nM) was equivalent to round 17a nucleic acid. There was another slight increase in affinity from round 18b to 19a ($K_d$=~2–3 nM). The affinity of rounds 20a, 21a, and 22a plateaued at about 1 nM. The SELEX was stopped at round 22a because the bound to background ratio was below 2 and it would have been technically difficult to reduce the protein concentration to 1–3 pM in round 23.

In summary the $K_d$ improved from ~500 nM in round 9b to ~1 nM in round 21a, resulting in an overall improvement of ~500-fold in the filter SELEX and >10,000-fold in the entire SELEX. The average improvement per round was only about 1.6-fold. This rate of improvement is slow compared to an average SELEX experiment, which may take ~5 rounds using only surface plasmon resonance technology or ~10 rounds using only filter partitioning.

Inhibition of Bioactivity by Nucleic Acid Pools

Rounds 0, 9-spr, 13-rm, 14i, 18b, and 19a, and latency-associated protein (LAP) were tested on mink lung epithelial cells for their ability to reverse TGFβ2-mediated inhibition of $^3$H-thymidine incorporation. The results are that the $K_i$ of the round 9-spr pool was about 711 nM. The $K_i$s of the round 14i, 18b, 19a, and 21a pools were about 231 nM, 309 nM, 154 nM and 10 nM, respectively. The $K_i$ of LAP was about 0.5 nM.

From these results it can be concluded that inhibitors of TGFβ2 were enriched in the later rounds of the TGFβ2 SELEX. In addition there is a continuous correlation between the affinity measured in vitro and the inhibitory activity measured in vivo:

LAP<round 19A<round 14i<round 13-rm<round 8-spr<round 0

Sequencing of Nucleic Acid Ligand Clones Isolated from Filter SELEX

Based on several criteria (pool $K_d$, filter-binding background, bound to noise background, inhibitory activity in cell assay, and absence of aberrant products during the RT-PCR steps of SELEX) round 21a was subcloned for sequence analysis. Forty eight clones were sequenced from round 21a (Table 8). Two unique sequences represented by clones 21a-4 and 21a-21 (the first number refers to the SELEX round a clone was initially isolated from and the second number is a clone number) were identified. Several clones were minor variants (1–6 bases different) of clones 21a-4 and 21a-21. One hundred more clones were screened by PCR using primers specific for clones 21a-4 and 21a-21. Of these, 90 were clone 21a-21-like, 9 were clone 21a-4-like, and 1 was a third unique sequence (21a-48), which was shown to be a nitrocellulose filter-binding sequence. In conclusion, Round 21a consists almost entirely of two sequences and variations of those sequences. This was not surprising because round 21a was the second to last round and the bulk affinity of the nucleic acid pools had not improved much from round 19a to 21a.

Since the sequence diversity of round 21a was restricted, 3 other rounds (14i, 16a, 18a) were also sequenced. Only one more novel sequence (14i-1 and variants) was isolated. Two filter-binding sequences were also isolated (16a-1 and a variant of 21a-48). Therefore, as with rounds 8-spr, 13-rm, and 21a, these 3 rounds also did not contain diverse TGFβ2-binding nucleic acid ligands.

The sequences of 14i-1, 21a-4, and 21a-21 are shown in Table 8. The affinity of the sequences for human TGFβ2 is about 10 nM, 3 nM, and 1 nM respectively. Therefore these 3 sequences are ligands that bind human TGFβ2 with high affinity.

The ligands were tested for inhibitory bioactivity. The $K_i$ of 14i-1, 21a-4, and 21a-21 are about 200 nM, 30 nM and 10 nM respectively. Thus these ligands are also inhibitory ligands. As for the pools the binding affinity correlates well with the inhibitory activity. This is not surprising since it is likely the TGFβ2 ligands bind near the heparin binding site which is very close to the TGFβ receptor binding region. The inhibitory activity of ligand 21a-21 was also compared to that of antibodies.

Clones were isolated and sequenced from six rounds (8-spr, 13-rm, 14i, 16a, 18a, and 21a). The number of each type of sequence is summarized Table 9. Out of 264 clones analyzed by sequencing and 100 clones analyzed by a PCR-based analysis using ligand-specific primers (Table 10), only 3 different TGFβ2 ligand sequences (and minor variants) were obtained. Fifteen sequences were filter-binding sequences and 36 were nucleic acids that do not bind well to filters or TGFβ2. The degree of restriction in sequence diversity observed in this SELEX is very unusual. Generally one can isolate dozens of different nucleic acid ligands and usually it is possible to find high affinity rounds were one ligand represents <10% of the population.

Since sequencing and screening of 6 rounds of SELEX that are as much as 13 rounds apart did not result in a diverse set of sequences the properties of the pools were investigated further to determine where the sequence diversity was restricted. Selected nucleic acid pools were sequenced and semi-quantitative RT-PCR on nucleic acid pools using ligand-specific primers was done. The results are shown in (Table 10). Taken together with the sequencing results, it appears that a restriction in sequence diversity during the SELEX process may have occurred near rounds 6-spr or 7-spr.

Clone 14i-1 is first detectable in round 6-spr, becomes most frequent near round 14i, and decreases in frequency in later rounds. Clone 21a-4 is first detectable by sequencing in round 14i, is most abundant in round 16a, and decreases in frequency by round 21a. However 21a-4 may exist in prior rounds (RT-PCR analysis of pools using a primer specific for clone 21a-4 was not done.) Clone 21a-21 was rare in round 14i (<1/104 clones by sequencing; estimate <1/200–500 clones by RT-PCR), became more frequent in round 16a, and composes most of round 18b and 21a.

It appears the surface plasmon resonance biosensor SELEX resulted in a high degree of diversity restriction, which has been observed before using this technology. The reason why various later rounds would consist of virtually one sequence is not clear. Perhaps only a very small number of sequences bind TGFβ2 under the selection conditions used. Perhaps a change in selection conditions such as the inclusion of competitors at round 9 or the switch from protein-excess binding reactions to nucleic acid-excess binding reactions at round 16 resulted in the emergence of clone 21a-21 as the predominant clone by round 21a. It seems as though the selection pressures were significant because the predominant ligand in a pool changed in as few as 2 rounds.

The pattern of changes in the population of nucleic acid ligands can be explained by analogy to the theory of natural selection. In an early SELEX round, a variety of sequences will exist. Strong selective pressure may narrow the sequence variation considerably, to the point that a single sequence is predominant. However rare ligands still exist that can be selected in future rounds or during significant changes in selective pressure. This is true in any SELEX experiment, but the TGFβ2 SELEX experiment described here may be an extreme example. In spite of the restriction on sequence diversity, better binding ligands could eventually be isolated. Note that ligand 21a-21 was first identified by sequencing in round 16a. Thus rare, high affinity nucleic acid ligands may exist even in round 22 that would only become predominant under the correct selection conditions. One approach for isolating such rare sequences might be to specifically deplete late rounds of SELEX of known sequences (e.g., by hybrid selection, restriction enzyme digestion of PCR products, site-directed RNase H cleavage of nucleic acid), an approach that this TGFβ2 SELEX is well suited for since essentially only 5 different sequences (3 ligands and 2 filter binding sequences) were present in later rounds. Isolating a sequence that is present in <1/1000 clones might be easy using depletion methods, but would be tedious using sequencing or PCR screening methods.

These results raise questions about when a SELEX is done and how to judge whether it is done. In this SELEX, standard criteria for judging when a SELEX is done such as $K_d$ improvement, and sequencing of clones or bulk nucleic acid pools may not be good criteria for judging if the SELEX had proceeded as far as it could. Often there are technical limitations (background, reaction volumes, loss of low amounts of protein to large surfaces) that determine when a SELEX must be terminated and these are artificially limiting. Perhaps a "depletion SELEX" round should be done at the end of every SELEX to attempt enrichment of ligands that would be difficult to isolate by currently used methods.

Specificity of Human TGFβ2 Ligands

For nucleic acid ligands to be most useful in the applications claimed herein they should be highly specific for a particular subtype of TGFβ. The specificity of human TGFβ2 ligands was investigated by in several ways.

Figure 6:
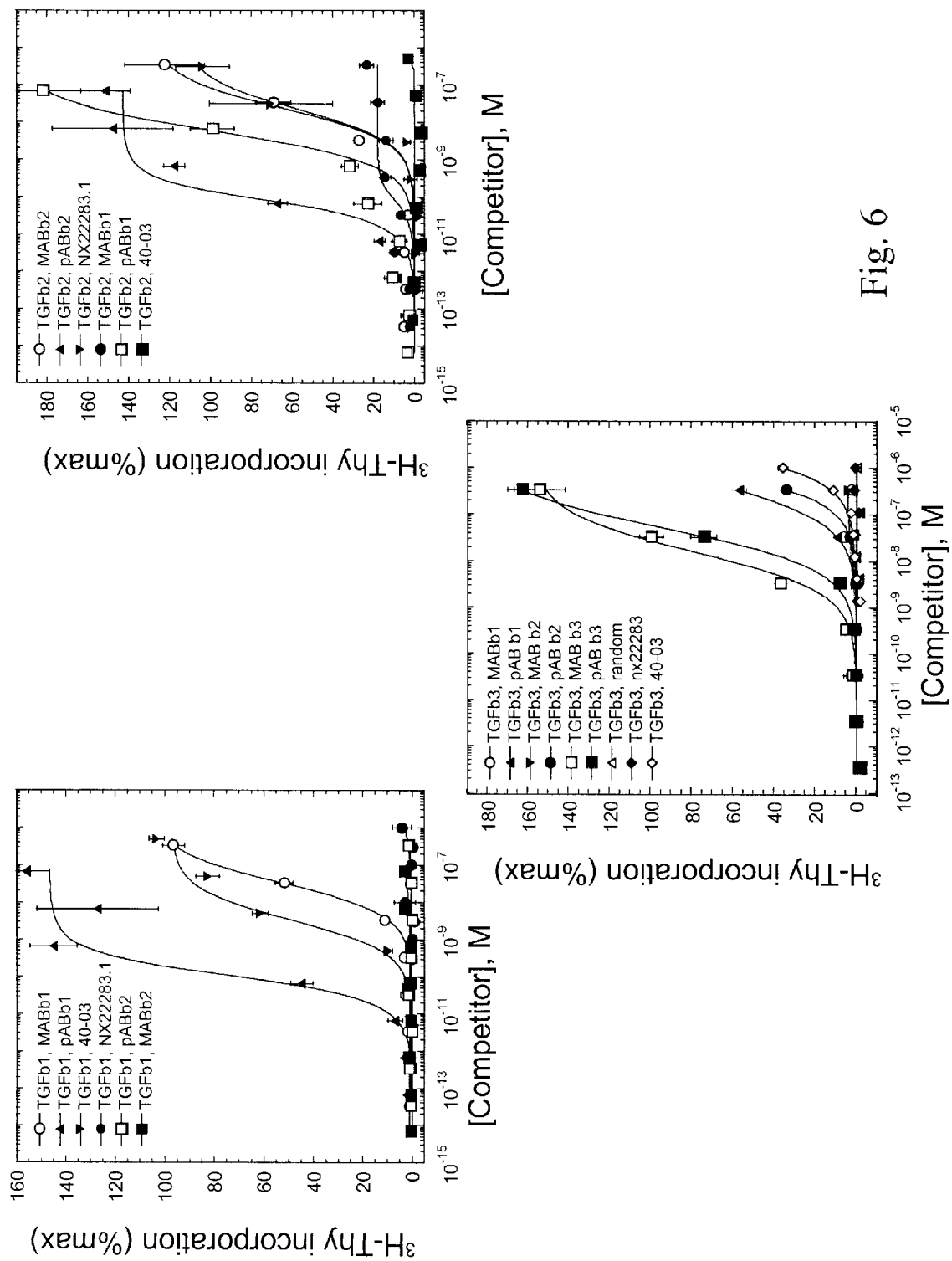
FIGS. 6A–6C shows specificity of the bioactivity of lead TGFβ1 and TGFβ2 aptamers and comparison with commercial antibody preparations. RNA was either synthesized by phosphoramidite chemistry (NX22283) or by in vitro transcription. Indicator cells (mink lung epithelial cells) were incubated with either TGFβ1, TGFβ2, or TGFβ3 and dilutions of RNA or antibody as described. The extent of cell proliferation was measured by $^3$H-thymidine incorporation and the data were analyzed as described. The points represent an average of n=2–6 and error bars are standard errors. Symbols designated by TGFβ1, TGFβ2, or TGFβ3 indicate data obtained from cells treated with either TGFβ1, TGFβ2, or TGFβ3, respectively. MAB and pAB designate monoclonal and polyclonal antibodies, respectively. Random, NX22283, and 40-03 designate the use of random RNA, the TGFβ2, or the TGFβ1 lead aptamer, respectively. The aptamer 40-03 was described in the TGFβ1 patent (U.S. patent application Ser. No. 09/046,247, filed Mar. 23, 1998).

The specificity of TGFβ2 ligands was examined using the cell culture bioactivity assay where the specificity of the TGFβ2 (described here) and TGFβ1 (see U.S. patent application Ser. No. 09/046,247, filed Mar. 23, 1998, entitled "High Affinity TGFβ Nucleic Acid Ligands and Inhibitors," which is incorporated herein by reference in its entirety) aptamers was compared to the specificity of antibodies. Two types of antibodies were used namely, monoclonal antibodies and immunopurified polyclonal antibodies. It was found (FIG. 6) that the TGFβ2 ligand NX22283 inhibited TGFβ2 protein bioactivity ($K_{i\_}$=10 nM), but not TGFβ1 ($K_{i\_}$>1000 nM) or TGFβ3 bioactivity ($K_{i\_}$>1000 nM). The TGFβ2 ligand NX22283 inhibits the TGFβ2 bioactivity with a potency equivalent to that of a monoclonal antibody while the most potent inhibitor of TGFβ2 bioactivity in this experiment was an affinity-purified polyclonal antibody.

The specificity of a TGFβ2 ligand for TGFβ2 compared to TGFβ3 was also analyzed in nucleic acid binding assays. The affinity of round 0 40N7 nucleic acid or the full-length TGFβ2 ligand 21a-21 to human TGFβ2 protein was >10 μM or 1 nM, respectively. The affinity of round 0 nucleic acid or ligand 21a-21 to human TGFβ3 protein was >10 μM or >30 μM, respectively. Therefore the TGFβ2 ligand does not bind significantly to TGFβ3.

It was found that the TGFβ1 ligand 40-03 (1 (see U.S. patent application Ser. No. 09/046,247, filed Mar. 23, 1998, entitled "High Affinity TGFβ Nucleic Acid Ligands and Inhibitors,") bound to TGFβ3 although 1000-fold worse. These results indicate there may be one or more amino acids in common between TGFβ1 and TGFβ3 that are not found in TGFβ2 so that a TGFβ1 ligand can bind TGFβ1 and TGFβ3 but not TGFβ2 and so that the TGFβ2 ligand 21a-21 binds TGFβ2 but not TGFβ1 or TGFβ3. Indeed, as shown in Table 12, there are 19 amino acids out of 122 that are found in TGFβ2, but not in TGFβ1 or TGFβ3. Three of these differences (Lys-25, Arg-26, and Lys-94 in TGFβ2) are within a putative heparin binding region and may be important for determining the binding specificity of TGFβ ligands.

Truncation of Nucleic Acid Ligands

It is desirable to obtain the smallest "truncate" of a full length nucleic acid ligand so that it can be synthesized efficiently at the least cost. The goal of this study was to obtain ligands that are less than half their original length (<35 bases), yet retain about the same affinity as the full length ligand. Several approaches were used to identify truncates of the three TGFβ2 ligands.

RNase H and hybrid 2'-OCH₃ RNA/DNA oligonucleotides (5'N7 cleave, 3'N7 cleave; Table 1) were used to remove the 5' and 3' fixed sequences from 2'-Fl pyrimidine, 2'-OH purine nucleic acid ligands as described in U.S. patent application Ser. No. 09/275,850, filed Mar. 24, 1999, entitled "The Truncation SELEX Method," which is hereby incorporated by reference in its entirety.

Second, the "boundaries" of the ligands were identified using a previously described method (Fitzwater and Polisky (1996) Meth. In Enzymol. 267:275–301). Boundaries define the 5' and 3' ends of the smallest truncate. However boundary determination does not identify internal deletions that can be made. Also because of the nature of the boundary determination method, if a boundary falls within a run of pyrimidines or is too close to either end, then which nucleotide is the boundary must be determined by other methods (e.g., generation of ligands beginning or ending with each candidate boundary position followed by analysis of their binding to TGFβ2).

A third method used relied on plausible structural motifs to define hypothetical sequence boundaries. Synthetic oligonucleotides corresponding to these boundaries were synthesized and were tested for binding to TGFβ2.

A fourth approach for identifying TGFβ2 ligand truncates was to look at the location of sequence variations in each ligand. In ligands 21a-4 and 21a-21 the changes that occurred in sequence variants were distributed randomly throughout their sequences. However in ligand 14i-1, the sequence changes in variants were highly localized. This implied that the variable region of ligand 14i-1 could tolerate changes without affecting binding and that the whole variable region may be dispensable.

A fifth approach was to make internal deletions based on predicted structures. Portions of putative bulges, loops, or base pair(s) within predicted stems can be deleted. The success of this method depends critically on how close the structural model is to the real structure. For 21a-21 the most stable structure was found to be incorrect. Only when a structure closer to the real structure was identified (by using the biased SELEX method) could internal deletions of 21a-21 successfully be made.

Truncation of Ligand 14i-1

Using the RNase H truncation method it was determined that ligand 14i-1 requires the 5' but not the 3' fixed sequence (Table 13). Consistent with this result, when both the 5' and 3' fixed sequences were removed, ligand 14i-1 did not bind TGFβ2.

Figure 7:
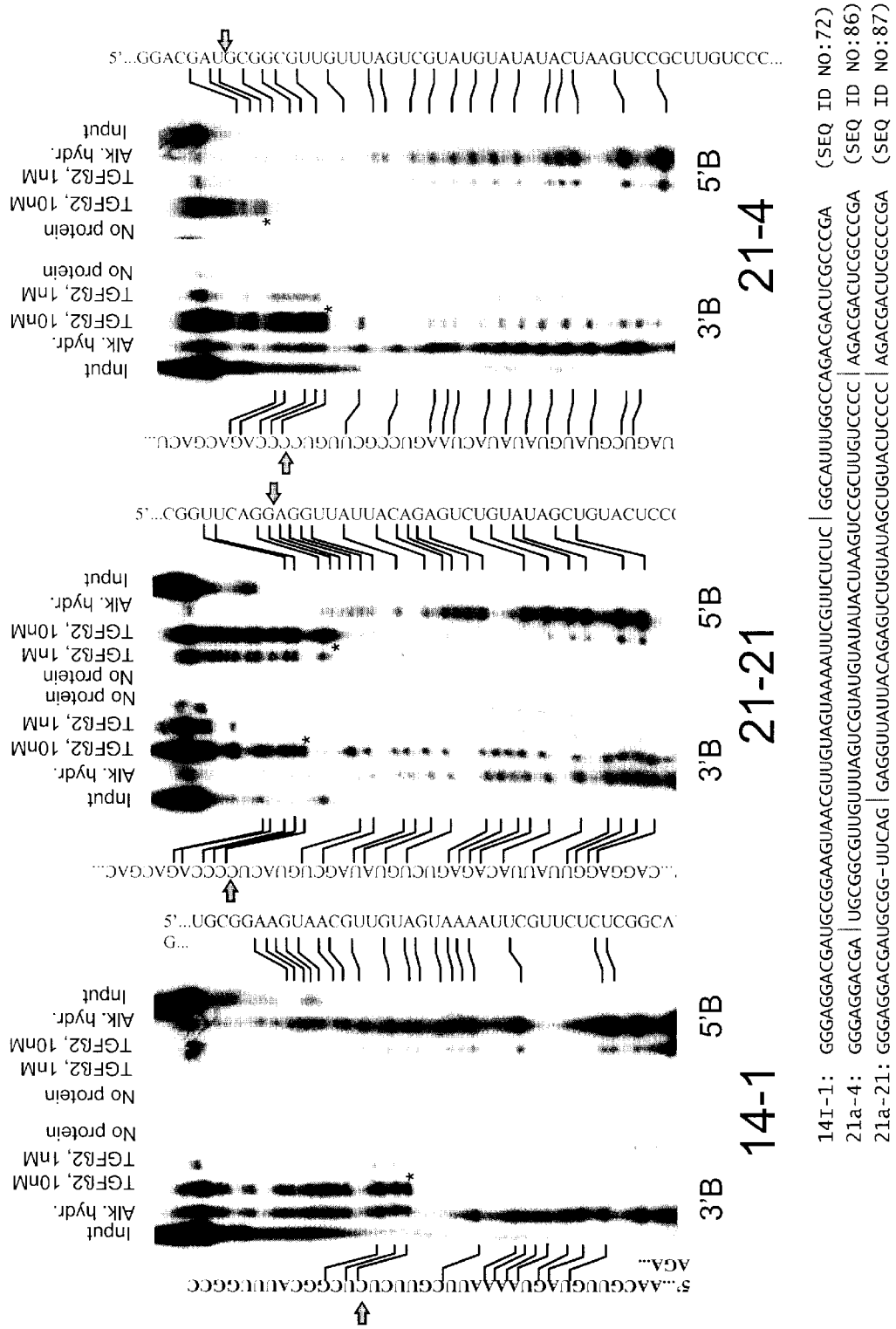
FIG. 7 shows boundaries of TGFβ2 ligands 14-1,21-21, and 21-4. RNA aptamers were end labeled at the 5' end (3'B) or at the 3' end (5'B), partially hydrolyzed at high pH, and partitioned for binding to TGFβ2 by nitrocellulose filtration as described in the Materials and Methods. The amounts of TGFβ2 used for binding partitioning is as shown. Recovered RNA was analyzed on high resolution sequencing gels and visualized by autoradiography. Unselected hydrolyzed RNA was used as a marker (Alk. hydr.) to align the banding pattern to the sequence of each ligand. The observed boundary bands are shown with (*) and their position in the sequence pattern is shown by arrowheads. No protein and input lanes show the background binding to nitrocellulose and the starting unhydrolyzed RNA. The observed boundaries for each ligand is summarized at the bottom of the figure.

Conventional boundary experiments defined the 3' end of ligand 14i-1 (FIG. 7) to be within positions 39–45. In the same experiment we failed to observe a clear boundary at the 5' end of this ligand. Of the 60 sequence variants of ligand 14i-1, 54 have nucleotide changes that occur within the last 16 bases at the 3' end of the selected sequence region. Most of the variants have single base changes, but a few have as many as 6 bases changed. Such changes may or may not affect binding. If they affect binding then that region is important for binding. More likely, since there are so many changes in so many clones within that region, those bases are probably not important. It was surmised they may be able to be deleted, possibly along with the adjacent 3' fixed region, without affecting binding. This idea was confirmed by two experiments:

1) The binding of 8 sequences that varied within the 16 base region and had different sequence changes was tested. They all bound as well to TGFβ2 as the 14i-1 ligand.
2) A 38 base long truncate of 14i-1 (14i-1t5-41; Table 13) that lacked the 3' fixed region and the 16 base variable region bound to TGFβ2 as well as the full length (71 base long) ligand.

Four sequences that removed additional bases from the ends of 14i-1 beyond those removed in 14i-1t5-41 were made [(14i-1t5–38, 14i-1t5–35, 14i-1(ML-87), and 14i-1 (Ml-89]. Also one internal deletion of 14i-1t5–41 was made [14i-1(ML-86)]. None of these bound to TGFβ2 (Table 13). Taken as a whole these experiments showed that the boundaries of ligand 14i-1 fall within positions 5–7 at the 5' end and 39–41 at the 3' end. All these results defined a truncate for ligand 14i-1 that is 38 bases long (Table 13).

Truncation of Ligand 21a-4

Using the RNase H truncation method it was determined that ligand 21a-4 requires the 5' but not the 3' fixed sequence (Table 14). When both the 5' and 3' fixed sequences were removed ligand 21a-4 did not bind TGFβ2.

The boundaries of ligand 21a-4 (FIG. 7) are at positions U11 in the 5' fixed region and within positions 52–56 on the 3' end, defining a truncate that is between 42–46 bases long (Table 8). This is consistent with RNase H truncation results which show 21a-4 requires the 5' end but not the 3' end to bind TGFβ2.

By examining hypothetical structures, the boundaries for 21a-4 were predicted to occur at position G12 at the 5' end and position C48 at the 3' end. These positions agree well with the region defined by the boundary method. A 37 base long truncate of 21a-4 (excluding sequences required to initiate transcription), beginning at position 12 and ending at position 48 [(21a-4(ML-110); Table 14)], bound as well to TGFβ2 as the full length 21a-4 ligand.

One sequence that removes 4 additional bases from the 3' end of 21a-4(ML110) was made that is called 21a-4(ML-111). The binding of 21a-4(ML-111) was reduced 30-fold compared to 21a-4(ML-110). Also three internal deletions of 21a-4(ML-110) were made [21a-4(ML-92, ML-108, and ML-109)]. None of these bound well to TGFβ2 (Table 14). A sequence [21a-4(ML-91)] that added 2 bases to the 3' end of 21a-4(ML111) did not have any improved binding compared to 21a-4(ML-110). Thus, the smallest truncate of ligand 21a-4 identified, that retains binding, is 42 bases long.

Truncation of Ligand 21a-21

Using the RNase H truncation method it was concluded that ligand 21a-21 requires the 3' but not the 5' fixed sequence (Table 11). However, when both the 5' and 3' fixed sequences were removed, ligand 21a-21 bound TGFβ2. This seems paradoxical since removal of the 3' end alone eliminates binding. However, the data can be interpreted to mean that the 3' deletion folds in a structure that does not bind to TGFβ2, while the truncate that lacks both ends does not fold into a dead end structure. Indeed Mfold structure predictions indicate this may be the case.

The boundaries of ligand 21a-21 (FIG. 7) are at position G21 on the 5' end and within positions 50–55 on the 3' end, defining a truncate that is 30–35 bases long. The results are consistent with RNAse H truncation data which shows that 21a-21 requires neither the 5' nor the 3' end to bind TGFβ2. The truncate identified by boundaries falls completely within that defined by RNase H truncation.

Synthetic sequences based on putative structures were also tested as summarized in Table 11. Results from these experiments are in agreement with the RNAse H and conventional boundary experiments.

Several additional end truncates and internal deletions of 21a-21(ML-95) were made (Table 11). The 9 end truncates included 21a-21(ML-96), 21a-21(ML-97), 21a-21(ML-103) 21a-21(ML-104) 21a-21(ML-105), NX22286, NX22301, NX22302, and NX22303. Of these only NX22301, which removes one base at the 5' end, binds as well as 21a-21 (ML-95). Internal deletions included 21a-21(ML-99), 21a-21(ML-101), 21a-21(ML-102), 21a-21(ML-114), 21a-21 (ML-115), 21a-21(ML-116), 21a-21(ML-118), 21a-21(ML-120), 21a-21(ML-122), 21a-21(ML-128), 21a-21(ML-132), 21a-21(ML-134), 21a-21(ML-136), and 21a-21(ML-138). Of these 14 internal deletions, only 21a-21(ML-130) bound about as well as 21a-21(ML-95).

Three sequences [21a-21(ML-94), NX22283, and NX22285), were made that are longer than 21a-21(ML-95). Of these only NX22285 may have bound (marginally) better than 21a-21(ML-95). Thus, the shortest ligand identified that binds TGFβ2 is the 34-mer NX22284.

NX22283 and NX22284, which are synthetic analogs of the transcribed ligands 21a-21(ML-94) and 21a-21(ML-95), respectively, bound with identical affinity to TGFβ2 (Table 11). The synthetic nucleic acids also have the same inhibitory bioactivity as their transcribed analogs; on the other hand, the short, 30-base long NX22286 and its transcribed analog 21a-21(ML-96) do not bind TGFβ2 and they do not inhibit TGFβ2 bioactivity. Therefore synthetic nucleic acids have the same properties as their transcribed counterparts.

To summarize, truncated 14i-1, 21a-4, and 21a-21 ligands were identified that bind TGFβ2 as well as the full length ligands and are 38, 37 (excluding 5 bases added to improve transcription yield), and 32 bases long, respectively. Twenty four sequences were made in an attempt to shorten the NX22284 truncated ligand (8 single base deletions and 16 multiple base deletions). Only 2 of them, (21a-21(ML-130) and NX22301, bind to TGFβ2. Therefore it appears that the sequence and spacing of structural elements in NX22284 must be maintained for binding to occur.

Competition Between Ligands for Binding TGFβ2

Examination of the ability of different ligands to compete with each other for binding to a protein can indicate whether the ligands bind to a similar (or overlapping) or distinctly different regions on the protein.

The ability of NX22283, a truncate of ligand 21a-21 (Table 14), to compete with 4 ligands (14i-1, 21a-4, 21a-21, and NX22283) was tested. The results were that NX22283 competed best with itself, then with 21a-21, 21a-4, and 14i-1, in decreasing effectiveness. Thus, the ability of NX22283 to compete correlates with how related its sequence is to the sequence of the test ligand. NX22283 is most closely related to itself and competes best with itself. NX22283 is a truncate of 21a-21, and competes with 21a-21 second best. The sequence of 21a-4 may be distantly related to 21a-21 and NX22283 competes with 21a-4 third best. The sequence of ligand 14i-1 is not related to NX22283, and NX22283 is least capable of competing with 14i-1.

The concentration range of NX22283 required to inhibit 50% of the binding of the other ligands was 10-fold. Since these differences in the amount of NX22283 it took to compete off the other ligands can be attributed to differences in their affinity there is probably only one type of binding region for these ligands on TGFβ2. However, there may be one or more similar sites per homodimer of TGFβ2. If there were two distinct types of nucleic acid binding sites on TGFβ2 (as is the case for the HIV-1 gag protein; Lochrie et al. (1997) Nuc. Acids Res. 25:2902–2910) it should take >1000 times as much competitor (i.e., the difference between the $K_d$ of round 0 nucleic acid and the $K_d$ of NX22283) to compete off a ligand binding at a second distinct site, because presumably a ligand that has high affinity at one site would have low affinity for a distinct site. This was not observed.

Off-rate of NX22283

The half-life for NX22283-TGFβ2 complex was measured in 2 experiments to be 0.5 or 3 minutes. Almost all of the ligand dissociated from TGFβ2 in 60–75 minutes. Although these times may seem short, they are typical of in vitro off-rate measurements for nucleic acid ligands that have been isolated by filter partitioning SELEX.

Example 3

Nucleic Acid Ligands Isolated by the SELEX Method Using a Biased Round 0 library A biased SELEX is one in which the sequences in a nucleic acid pool are altered to bias the result toward a certain outcome. The primary goals of a "biased" SELEX are to obtain ligands that have a higher affinity and to determine what the putative secondary structure of a ligand may be. The starting, round 0 nucleic acid library (called 34N7.21a-21) used for the TGFβ2 biased SELEX had the same 5' and 3' fixed regions (5'N7 and 3'N7) as the prior TGFβ2 SELEX (Table 1). It was made as a 2'-F pyrimidine, 2'-OH purine nucleic acid. However, as described in the "Materials and Methods" section, the random region was 34 bases long. Within the randomized region 62.5% of the nucleotides at each position correspond to the NX22284 sequence. The remaining 37.5% correspond to the other three nucleotides. Thus each position is mutagenized and the sequence of the pool is biased toward the NX22284 sequence. Selection for ligands that bind to TGFβ2 using such a pool should allow variants of NX22284 to be isolated, some of which may not have been present in the original 30N7 round O pool.

The bulk $K_d$ of the round 0 34N7.21a-21 pool was about 870 nM (Table 15) using protein-excess binding conditions. This is at least 10-fold better than for the unbiased round 0 40N7 pool, as would be expected. This round 0 nucleic acid pool also bound under nucleic acid-excess conditions in small scale SELEX type reactions, although poorer than in protein-excess reactions, as would be expected. The progress of the biased SELEX is shown in Table 15.

The conditions used in the biased SELEX and the results are shown in Table 15. A total of 9 rounds were done. Attempts were made to obtain higher affinity ligands by using competitors, starting at round 4. Both yeast tRNA (low affinity) and NX22284 (high affinity) were used as competitors. Both are nonamplifiable during the PCR step of SELEX. The "A" series was done without competitors while the "B" series was done with competitors.

The binding of the nucleic acid pools to TGFβ2 was measured for rounds 0 to 8 (Table 15) and found to improve from ~870 nM for the round 0 nucleic acid library to ~1 nM for the round 5a nucleic acid pool. Competition seemed to have little consistent effect on affinity improvement in this SELEX experiment. Probably competition should have been initiated with NX22284 at round 1. Peak improvement in the pool affinity plateaued in rounds 5, 6 and 7, and 8. Therefore round 5a, the earliest round with the best affinity, was subcloned and sequenced.

Sequences of TGFβ2 Nucleic Acid Ligands Obtained from a Biased SELEX.

As shown in Table 16, 25 unique sequences were obtained. One to nine changes from the starting sequence were found. All of the clones were 34 bases long within the selected sequence, consistent with studies (see "Truncation of ligand 21a-21" above) where it was difficult to delete any internal bases.

Figure 8:
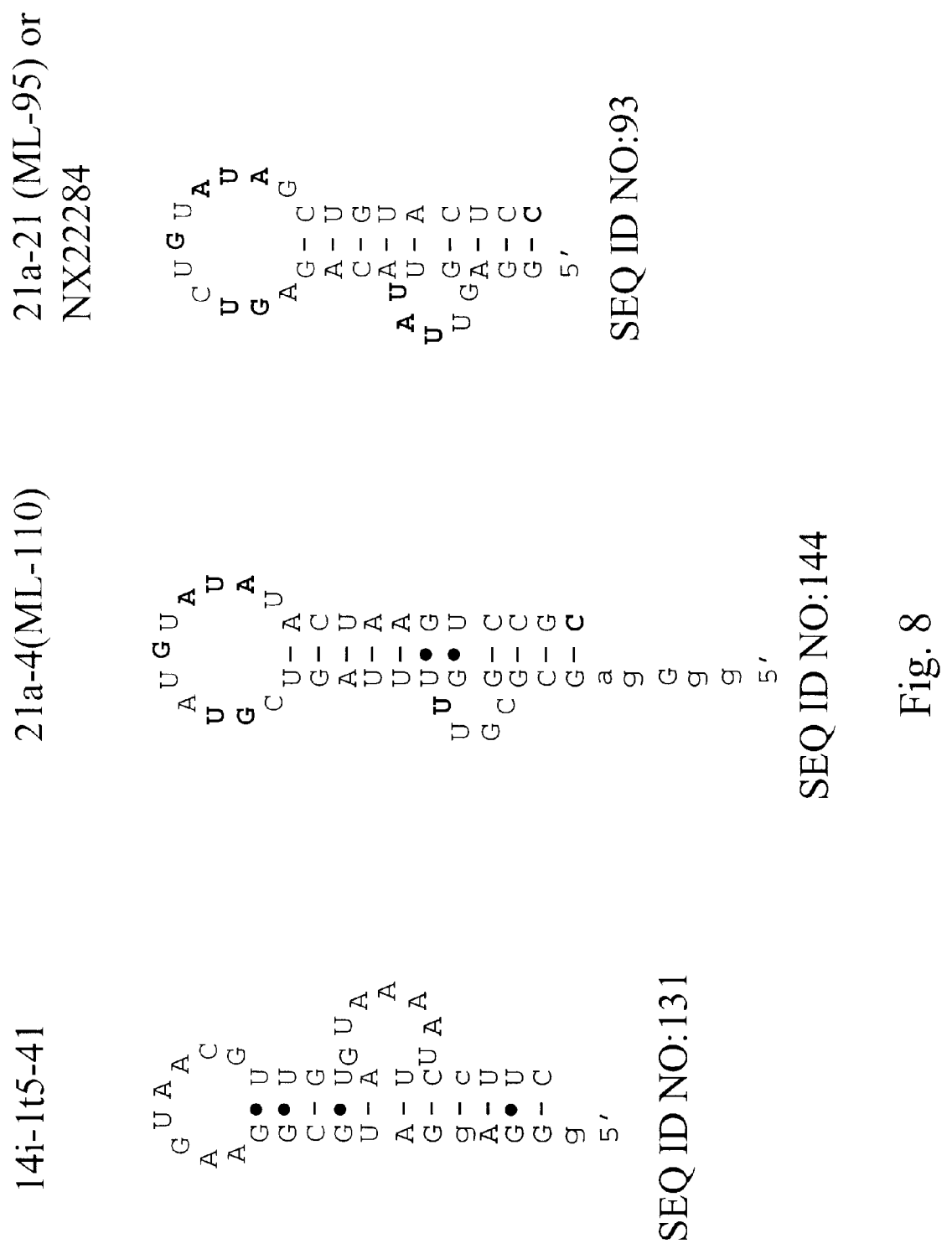

Covariance between pairs of positions was analyzed by eye and by using the consensus structure matrix program (Davis et al. (1995) Nucleic Acids Research 23:4471–4479). Covariance was observed between 2 different areas implying the existence of 2 stems in the structure. The pattern of covariance suggests the structural model shown in FIG. 8 or a similar variant of that structure (e.g., some base pairing could occur within the loop). This predicted structure is the third most stable structure predicted by the Mfold program (Zuker (1989) Science, 244:48–52). A curious example of possible covariance is observed at positions 15 and 25 in the loop region. A15 and G25 were observed to covary to C15 and U25 in 2 clones (#18 and #29). Ligand 21a-4 also has the C/U combination at the bottom of its putative loop.

Of 34 bases, 11 are "invariant" among these 25 clones (Table 16). All of the invariant positions are predicted to occur in the loop and bulge regions except C34, the last nucleotide. The last base of all 3 truncated TGFβ2 ligands (FIG. 8) is a C. Removal of this C results in loss of binding. If invariant positions indicate regions where TGFβ2 binds the NX22284 ligand, then binding may occur primarily in the bulge and stem loop regions. The stems must be base paired, but can vary in sequence implying that the structure of the stems may be more important than their sequence. The stem may be a structure used to present the bulge, loop and C34 nucleotides in the proper orientation to bind TGFβ2.

Clone 5a-11 from the biased SELEX is similar to clone 21–4 from the primary SELEX, particularly at positions that are invariant in clones from the biased SELEX, thus reinforcing the new structural model and the importance of the invariant positions. It has not been possible to fit ligand 14i-1 into a similar structure. Perhaps it represents a second sequence motif capable of binding TGFβ2.

Binding of Nucleic Acid Ligands Isolated from the Biased SELEX

The binding of clones from the biased SELEX was compared to the binding of full length ligand 21a-21. The majority of the clones bound as well to TGFβ2 as 21a-21 (Table 16). One clone (#20) bound about 6-fold worse and one clone (#13) bound about 5-fold better than full length ligand 21a-21. The average $K_d$ of the clones (weighting clones found more than once) is 1.2 nM, which agrees with the round 5a pool $K_d$ of ~1 nM. Thus the ligands that were isolated in this manner were not vastly different in affinity from the starting sequence.

One would expect there to be an optimal number of changes that results in higher affinity ligands. Clones with only a few changes might be expected to bind about the same as the starting sequence, clones with a threshold number of changes may bind better, and clones with too many changes may bind worse. Indeed there may be a correlation between the number of changes and the affinity. Clones with 1 to 4 changes tend to bind the same or worse than ligand 21a-21. Clones with 5–8 changes tend to bind better than ligand 21a-21. The worst binder (#20) was the one with the most changes (9). The ligand that bound to TGFβ2 the best (clone #13) had 7 changes relative to the starting sequence.

When the clones that bound better and those that bound worse are aligned (Table 17) it appears that an A at position 5 may be important for higher affinity binding since the ligands that bind to TGFβ2 best all have an A at position 5 and all clones with an A at position 5 bind at least as well as 21a-21. In contrast clones with a U, C, or G at position 5 tend to bind worse than 21a-21. With regard to the pattern of base pair changes in the putative stems there is no single change that correlates with better binding. In addition, the better binders do not consistently have GC-rich stems. However the pattern of changes in the stems of the poor binders does not overlap with that seen in the stems of the better binders. Thus, various stem sequences may result in better binding for subtle reasons.

A point mutant that eliminated binding of the full length 21—21 transcript (21a-21(ML-107); Table 11) changes U at position 6 to G. A G was found at position 6 in three clones from the biased SELEX (#4, 9, and 35), one of which (clone #4) has only one other base change while the others had additional changes. All three clones from the biased SELEX that have a G at position 6 bind TGFβ2. Thus it would seem that the U6G change alone eliminates binding, but this binding defect can be reversed when combined with other sequence changes.

To summarize, some changes (such as A at position 5) may act independently and be able to confer better binding alone, while others changes (e.g, at position 6 and in the stems) may influence binding in a more unpredictable way that depends on what other changes are also present.

Presumably sequences that lack an "invariant" nucleotide would not bind to TGFβ2. Some of the invariant bases have been deleted and others have been changed (Table 11. None of these 10 altered sequences [21a-4(ML-111); 21a-21(ML-96, 97, 101, 102, 103, 104, 105, 120, NX22286] bind to TGFβ2.

Example 4

Substitutions of 2'-OH Purines with 2'-OCH$_3$ Purines in NX22284

Substitutions of 2'-OH purines with 2'-OCH$_3$ purines sometimes results in nucleic acid ligands that have a longer half life in serum and in animals. Since the nucleic acid ligands described here are ultimately intended for use as diagnostics, therapeutics, imaging, or histochemical reagents the maximum number of 2'-OH purines that could be substituted with 2'-OCH$_3$ purines in ligand NX22284 was determined. NX22284 is a 34-mer truncate of the 70 base long 21a-21TGFβ2 ligand (Table 18). NX22284 has 17 2'-OH purines and binds about 2-fold worse than ligand 21a-21.

Initially an all 2'-OCH$_3$ purine substituted sequence was synthesized (NX22304). Another sequence has all 2'-OH purines substituted with 2'-OCH$_3$ purines except six purines at its 5' end. Neither bound to TGFβ2 or had measurable bioactivity (Table 18).

Therefore a set of sequences was synthesized (NX22356-NX22360; Table 18) such that groups of 3 or 4 2'-OH purines were substituted with 2'-OCH$_3$ purines. The binding of NX22357 was reduced about 2-fold and the bioactivity was reduced 10-fold. The binding and bioactivity of NX22356, NX22258, and NX22360 were unaffected. In contrast the binding of NX22359 was reduced over 100-fold and its bioactivity was reduced over 30-fold. Therefore the sequence of NX22359 was "deconvoluted" one base at a time in order to determine which individual purines in NX22359 cannot be 2'-OCH$_3$ purines NX22374, NX22375, and NX22376 are deconvolutions of NX22359. All three of these sequences had greatly reduced binding and bioactivity. This suggests that G20, A22, and A24 cannot be 2'-OCH$_3$ purines.

NX22377 was designed to determine if a sequence with an intermediate number of 2'-OCH$_3$ purines could bind TGFβ2 and retain bioactivity. NX22377 has 10 2'-OCH$_3$ purines out of 17 (representing the 2'-OCH$_3$ purines in NX22356, NX22357, and NX22360). The binding and bioactivity of NX22377 are identical to NX22284.

NX22417 was designed to test the possibility that G20, A22, and A24 must be 2'-OH purines in order to retain binding and bioactivity. In NX22417 G20, A22, and A24 are 2'-OH purines while the other 14 purines are 2'-OCH$_3$. NX22417 binds to TGFβ2 as well as NX22284, but its bioactivity is reduced about 10 fold. Since substitution of G20 (NX22374) or A24 (NX22376) alone had a less severe effect than substitution of A22 (NX22375), nucleic acids were synthesized that had all 2'-OCH$_3$ purines except position A22 (see NX22384) or G20 and A22 (see NX22383). NX22383 and NX22384 did not bind or inhibit TGFβ2, again suggesting that at least 3 purines at positions 20, 22, and 24 must be 2'OH to retain binding and bioactivity.

NX22384 was analyzed by mass spectroscopy to ensure its lack of binding and inhibitory activity was not due to incomplete deprotection or an incorrect sequence. The results are that NX22383 may be 0.5–0.9 daltons more than the predicted molecular weight and therefore is very likely to be what it should be.

Since NX22357 bound to TGFβ2 slightly worse than NX22284 but had a 10-fold reduced bioactivity, it was possible that one or more of the three 2'-OCH$_3$ purines in NX22357 (G5, A8, A11) may also be required for bioactivity. This notion was tested by synthesizing NX22420 and NX22421. NX22421 has all three of these bases (G5, A8, and A11) as 2'-OH purines (along with G20, A22, and A24, which require 2'-OH groups). NX22420 has A8 (along with G20, A22, and A24) as 2'-OH purines. NX22421 has G5, A8, and A11 (along with G20, A22, and A24) as 2'-OH purines. A8 was retained as a 2'-OH purine in both NX22420 and NX22421 because it was invariant among the clones from the biased SELEX and therefore it was inferred that A8 might be less tolerant to change at the 2' ribose position (as was the case for G20, A22, and A24). Indeed both NX22420 and NX22421 had approximately the same binding and inhibitory activity as NX22284. In summary, the NX22284 sequence can retain maximal binding and inhibitory activity when four purines (A8, G20, A22, and A24) are 2'-OH and the other purines are 2'-OCH$_3$. Note that all four of these positions were invariant among the clones isolated using the biased SELEX method.

While studies were being done on substituting the 2'-OH purines of NX22284, two shorter versions of NX22284 (21a-21[ML-130] and 21a-21[ML-134]; Table 11) were discovered that bound well to TGFβ2 as transcripts. The 2'-OCH$_3$ purine substitution pattern of NX22420 was transferred to these sequences. NX22426 is the 2'-OCH$_3$ purine analog of 21a-21(ML-134) and NX22427 is the 2'-OCH$_3$ purine analog of 21a-21(ML-130). NX22426 bound well to TGFβ2, but had 25-fold reduced bioactivity. NX22427 may have slightly better binding and inhibitory activity than NX22284.

In summary, the human TGFβ2 ligand isolated by using combined spot, spr, and filter SELEX methods which have the best combination of affinity, short length, and inhibitory activity is NX22427, a 32-mer with 12 2'-OCH$_3$ purines out of a total of 16 purines.

Substitutions of 2'-OH Purines with 2'-OCH$_3$ Purines in NX22385

Some of the ligands that were isolated using the biased SELEX method (e.g., clone 13) bound better to TGFβ2.

To compare the properties of a truncated clone 13 to truncated 21a-21, NX22385 was synthesized. NX22385 (Table 19) is a 34 base long, 2'-F pyrimidine, 2'-OH purine version of biased SELEX clone #13. It binds about 2.5-fold better than NX22284, the corresponding 34 base long truncate of 21a-21, but its inhibitory activity is about 4-fold worse.

For reasons mentioned in the previous section it was of interest to determine if the properties of a truncated clone 13t when synthesized as a 2'-F pyrimidine, 2'-OCH$_3$ purine nucleic acid. Two 2'-OCH$_3$ purine versions of NX22385 (NX22424 and NX22425; Table 19) were synthesized based on the 2'-OCH$_3$ pattern of NX22420, a truncate of 21a-21. In both nucleic acids A8, G20, A22, and A24 were retained as 2'-OH purines, as in NX22420. In NX22424, the purines that are unique to clone 13 (A5, A6, and G12) are 2'-OH purines. In NX22425, those purines are 2'-OCH$_3$ purines. Analogs of NX22424 and NX22425 were also synthesized in which A24 (NX22386) or G20 and A24 (NX22387) are 2'-OCH$_3$ purines. NX22386 and NX22387 were expected to serve as negative controls since 2'-OCH$_3$ G20 or A24 version of NX22284 were inactive. As expected NX22386 and NX22387 did not bind or inhibit TGFβ2. NX22424 and NX22425 bound to TGFβ2 as well as NX22284, but were reduced >100-fold in bioactivity (Table 19). Therefore, while other sequences that bind as well as NX22284 were isolated, no other sequence was identified that have better bioactivity.

Example 5

Pharmacokinetic Properties of NX22323

Figure 9:
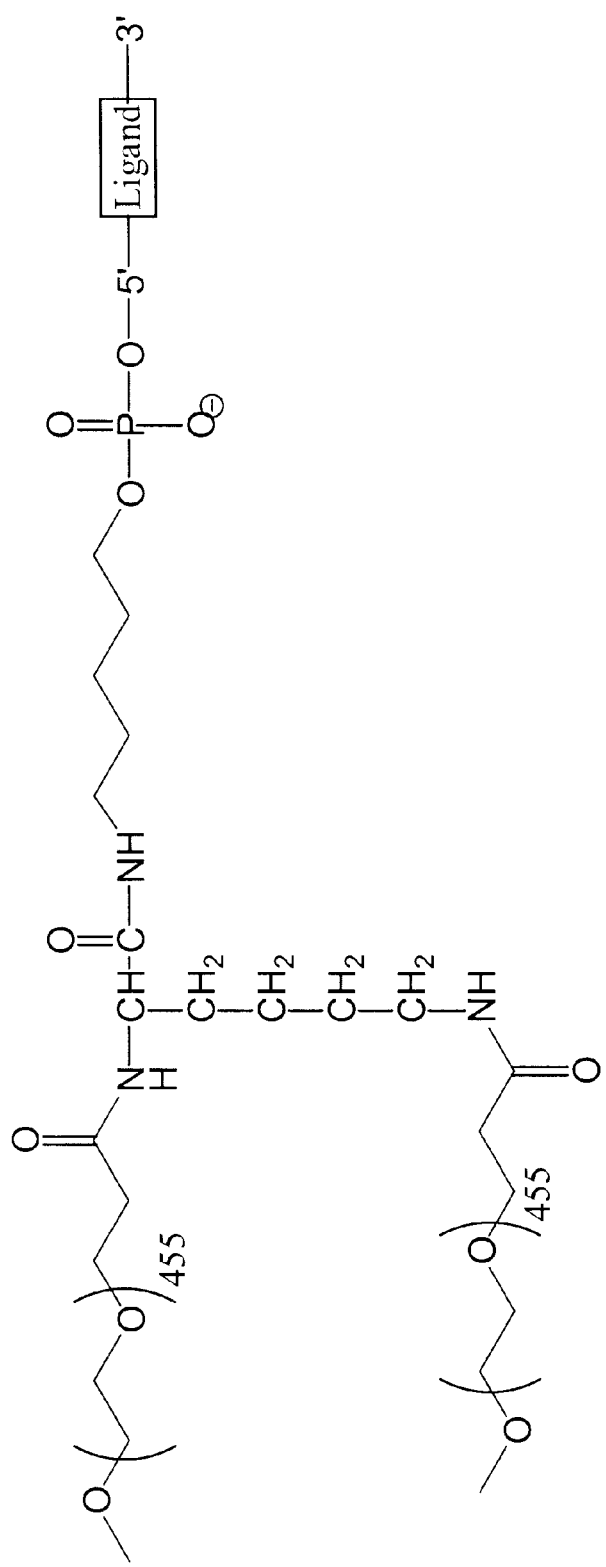
FIG. 9 shows the molecular description of NX22323 40k PEG. rG=2'OH G; rA=2'-OH A; EU=2'FU; fC=2'FC.
Figure 11:
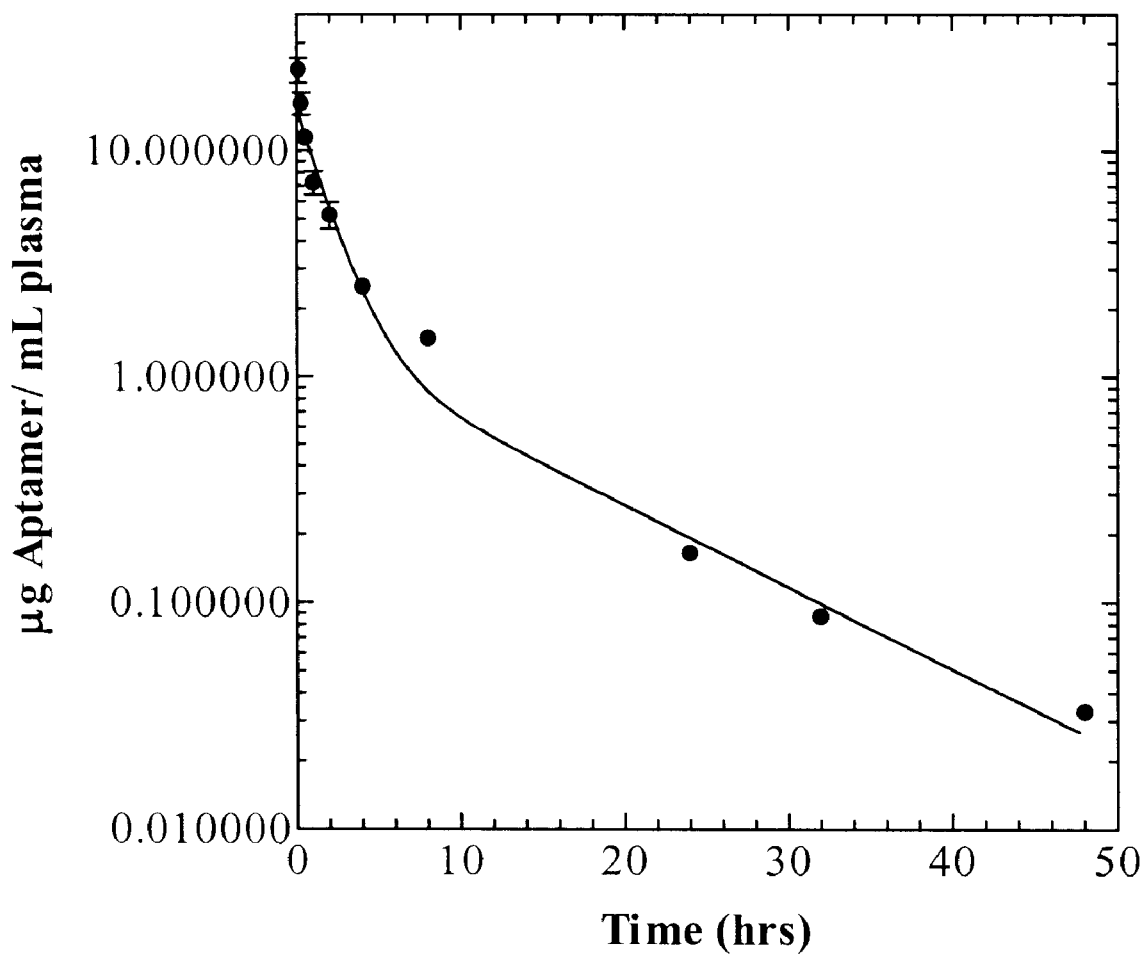
FIG. 11 shows the pharmacokinetics of TGFP aptamer in sprague dawley rats.

NX22323 is a 5'-polyethylene glycol-modified version of NX22284 (see Table 11; FIG. 9). The plasma concentrations of NX22323 were measured in rats over a 48 hour time period and are shown in FIG. 11 with the corresponding pharmacokinetic parameters in Tables 20 and 21. These data demonstrate biphasic clearance of NX22323 from plasma with an initial clearance half life ($\alpha T_{1/2}$) of 1 hour and a terminal clearance half life ($\beta T_{1/2}$) of 8 hours. The volume of distribution at steady state was approximately 140 mL/kg suggesting only minor distribution of the aptamer with the majority remaining in plasma and extracellular water. The clearance rate determined by compartmental analysis was 0.40 mL/(min*kg). This value was consistent with other aptamers with similar chemical composition (5'-PEG 40K, 3'-3' dT, 2'F pyrimidine, 2'-OH purine nucleic acid). These data support daily administration of NX22323 for efficacy evaluation.

Example 6

2' Omethyl Modification of Lead Truncate Ligand CD70

Figure 10:
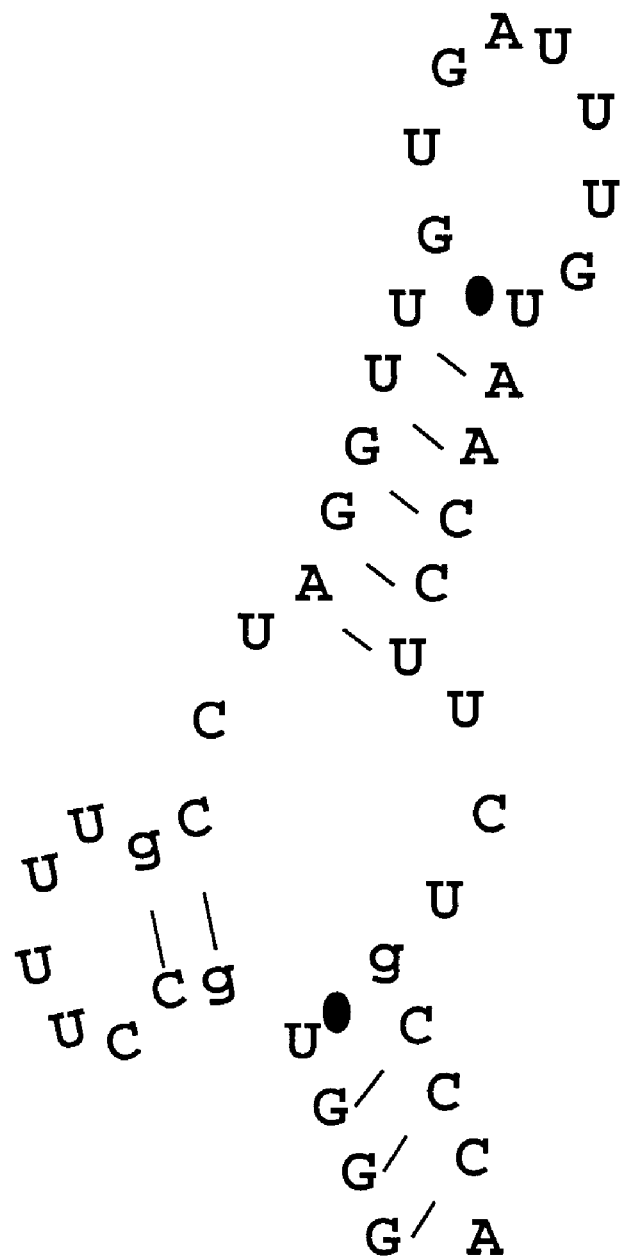
FIG. 10 shows the putative structure of lead truncate ligand CD70. Lower case letters indicate positions requiring 2'OH. • indicates GU base pairing.

TGFβ1 nucleic acid ligands are disclosed in U.S. patent application Ser. No. 09/275,850, filed Mar. 24, 1999, entitled "The Truncation SELEX Method," which is incorporated herein by reference. A lead aptamer was generated by truncation SELEX by hybridization (see Table 11, Family 4, Ligand #70 in U.S. patent application Ser. No. 10 09/275, 850), herein called CD70. CD70 derivative oligonucleotides were synthesized containing 2'OMe modifications at various positions as summarized in Table 22. The results suggest that 13 out of 16 purines can be substituted with their 2'OMe counterparts without any loss of activity. The molecule with the maximum 2'OMe modifications (CD70-m13) is also bioactive (Table 22). FIG. 10 shows a putative structure of CD70-m13 and the positions of that require the presence of 2'OH nucleotides. Of interest is the A position at the 3' end of the molecule which according to the proposed structure does not participate in a secondary structure. Deletion of this single stranded A affects somewhat the binding activity of the molecule but it completely eliminates its bioactivity (Table 22). The 2'OH bases and the 3' final A are in close proximity in the proposed structure. This suggests a domain of the molecule responsible for target binding. Under these circumstances, it is expected that the loop shown at the top of the proposed structure (FIG. 10) may not be necessary for binding. This was confirmed by replacing such a loop with a PEG linker and showing that such modified molecules retain binding (Table 22). The PEG linker was conjugated to the aptamer as shown in U.S. patent application Ser. No. 08/991,743, filed Dec. 16, 1997, entitled "Platelet Derived Growth Factor (PDGF) Nucleic Acid Ligand Complexes," which is hereby incorporated by reference in its entirety. The shortest binding aptamer identified from these experiments is CD70-m22, a 34-mer (including the PEG linker).

TABLE 1. Sequences used during SELEX.

(all are shown in a 5' to 3' direction, and separated by a blank every 10 bases)

Sequences Involved in SELEX Process:

(P0; DNA template for round 0 of spot SELEX)
TCGGGCGAGT CGTCTGNNNN NNNNNNNNNN NNNNNNNNNN NNNNNNNNNN 50
NNNNNNCCGC ATCGTCCTCC C 71 (SEQ ID NO: 1)
A=dA; C=dC; G=dG; T=dT; N+25% each of dA, dC, dG, or dT (5'N7; primer used in PCR steps of SELEX)
TAATACGACT CACTATAGGG AGGACGATGC GG 32 (SEQ ID NO: 2)
A=dA; C=dC; G=dG; T=dT (3'N7; primer used in RT and PCR steps of SELEX)
TCGGGCGAGT CGTCTG 16 (SEQ ID NO: 3)
A=dA; C=dC; G=dG; T=dT (Transcription template for round 0 of spot SELEX)
TAATACGACTCACTATAGGGAGGACGATGCGG-40N-CAGACGACTCGCCCGA 88 bp (SEQ ID NO:4)
ATTATGCTGAGTGATATCCCTCCTGCTACGCC-40N-GTCTGCTGAGCGGGCT (SEQ ID NO: 5)
A=dA; C=dC; G=dG; T=dT; N=25% each of dA, dC, dG, or dT (R0 40N7; nucleic acid library for round 0 of spot SELEX)
GGGAGGACGA UGCGGNNNNN NNNNNNNNNN NNNNNNNNNN NNNNNNNNNN 50
NNNNNCAGAC GACUCGCCCG A 71 (SEQ ID NO: 6)
A=2'-OH A; C=2'-F C; G=2'-OH G; N=25 % each of 2'-OH A, 2'-F C, 2'-OH G, and 2'-F U; U=2'-F U (34N7.21a-21 DNA template for round 0 of biased SELEX)
GGGAGGACGA TGCGGNNNNN NNNNNNNNNN NNNNNNNNNN NNNNNNNNNC 50
AGACGACTCG CCCGA 65 (SEQ ID NO: 7)
A=dA; C=dC; G=dG; T=dT, N=62.5% NX22284 sequence as DNA and 12.5% of the other 3 nucleotides (dA, dC, dG, or dT) at each position (Transcription template for round 0 of biased SELEX)
TAATACGACTCACTATAGGGAGGACGATGCGG-34N-CAGACGACTCGCCCGA 82 bp (SEQ ID NO: 8)
ATTATGCTGAGTGATATCCCTCCTGCTACGCC-34N-GTCTGCTGAGCGGGCT (SEQ ID NO: 9)
A=dA; C=dC; G=dG; T=dT, N=62.5% NX22284 sequence as DNA and 12.5% of the other 4 nucleotides (dA, dC, dG, or dT) at each position
(34N7.21a-21 nucleic acid library for round 0, biased SELEX)
GGGAGGACGA UGCGGNNNNN NNNNNN NNNNNNNNNN NNNNNNNNNC 50
AGACGACUCG CCCGA 65 (SEQ ID NO: 10)
A=2'-OH A; C=2'-Fl C; G=2'-OH G; N=62.5% NX22284 sequence and 12.5% of other 4 nucleotides (2'-OH A, 2'-F C, 2'-OH G, or 2'-F U) at each position; U=2'-F U
Sequences Used for Subcloning, Screening, Sequencing Ligand
(ML-34; used for subcloning)
CGCAGGATCC TAATACGACT CACTATA 27 (SEQ ID NO: 11)
A=dA; C=dC; G=dG; T=dT
(ML-78; used for subcloning)
GGCAGAATTC TCATCTACTT AGTCGGGCGA GTCGTCTG (SEQ ID NO: 12)
A=dA; C=dC; G=dG; T=dT
(RSP1; vector-specific primer used to screen transformants for ligand inserts)
AGCGGATAAC AATTTCACAC AGG 23 (SEQ ID NO: 13)
A=dA; C=dC; G=dG; T=dT
(FSP2; vector-specific primer used to screen transformants for ligand inserts)
GTGCTGCAAG GCGATTAAGT TGG 23 (SEQ ID NO: 14)
A=dA; C=dC; G=dG; T=dT
(RSP2; primer for sequencing ligands)
ACTTTATGCT TCCGGCTCG 19 (SEQ ID NO: 15)
A=dA; C=dC; G=dG; T=dT
Sequences Used to Detect Specific Ligands
(ligand 14i-1 specific primer; ML85)
GCCAAATGCC GAGAGAACG 19 (SEQ ID NO: 16)
A=dA; C=dC; G=dG; T=dT
(ligand 21a-4 specific primer; ML-79)
GGGGACAAGC GGACTTAG 18 (SEQ ID NO: 17)
A=dA; C=dC; G=dG; T=dT
(ligand 21a-21 specific primer; ML-81)
GGGAGTACAG CTATACAG 18 (SEQ ID NO: 18)
A=dA; C=dC; G=dG; T=dT
Sequences Used for RNAse H Cleavage
(5'N7 cleave)
CCGCaugcuc cuccc 15 (SEQ ID NO: 19)
a=2'-OCH$_3$ A; c=2'-OCH$_3$ C; C=dC; g=2'-OCH$_3$ G; G=dG; u=2'-OCH$_3$ U
(3'N7 cleave)
ucgggcgagu cgTCTG 16 (SEQ ID NO: 20) a=2'-OCH$_3$ A; c=2'-OCH$_3$ C; C=dC; g=2'-OCH$_3$ G; G=dG; u=2'-OCH$_3$ U; T=dT

TABLE 2

Conditions and results of filter SELEX

| Round[a] | [RNA][b], nM | [TGFβ2], nM | RNA[b]/protein | [Competitior] | % Bound | % Background | Bound/Background | Kd (nM) |
|---|---|---|---|---|---|---|---|---|
| 9b | 1 nM | 100 nM | 0.01 | 100 μM tRNA | 4.2 | 1.1 | 4 | nd |
| 10b | 1 nM | 30 nM | 0.03 | 100 μM tRNA | 4.3 | 0.13 | 33 | 100 |
| 11a | 1 nM | 30 nM | 0.03 | 100 μM tRNA | 1.5 | 0.2 | 8 | 75 |
| 12d | 0.2 nM | 20 nM | 0.01 | 250 μM tRNA | 2.2 | 0.3 | 7 | 40 |
| 13i | 0.4 nM | 10 nM | 0.04 | 10 μM tRNA | 2.6 | 0.16 | 16 | 30 |
| 14i | 0.1 nM | 10 nM | 0.01 | 10 μM heparin | 14.5 | 0.55 | 20 | 75 |
| 15c | 10 nM | 10 nM | 1.0 | 0 | 8.8 | 2.2 | 4 | 30 |
| 16a | 55 nM | 10 nM | 5.5 | 0 | 9.6 | 2.1 | 5 | 10 |
| 17a | 30 nM | 3 nM | 10 | 0 | 1.9 | 0.17 | 11 | 5 |
| 18b | 15 nM | 3 nM | 5 | 0 | 2.3 | 0.6 | 4 | 5 |
| 19a | 7 nM | 0.1 nM | 70 | 0 | 0.17 | 0.05 | 3 | 2 |
| 20a | 0.33 nM | 0.03 nM | 11 | 0 | 0.1 | 0.04 | 3 | 1 |
| 21a | 0.63 nM | 0.03 nM | 21 | 0 | 0.3 | 0.1 | 3 | 1 |
| 22a | 0.07 nM | 0.01 nM | 7 | 0 | 0.12 | 0.09 | 1 | 1 |

[a]Number designates the round of SELEX and letter designates the condition used for that round.
[b]NA, nucleic acid library
Only those rounds that were carried to the next round are shown

TABLE 3

Conditions and results of Spot SELBX

| Rd | Protein (pmoles) | RNA (pmoles) | Washes[1] (μl/min) | Signal/ Noise | % Input | Incubation | Pre-adsorb[2] |
|---|---|---|---|---|---|---|---|
| 1 | *200 | 2000 | 2 (500/10) | 4.90 | ND[3] | 4 hrs, 20° C. | No |
| 2 | *200 | 1500 | 2 (1000/10) | 1.80 | ND | 0.5 hrs, 37° C. | 5 layers, 0.75 hrs |
| 3 | *200 | 1500 | 2 (1000/10) | 5.50 | ND | 1 hr, 37° C. | 5 layers, 1 hr |
| 4 | *200 | 1000 | 2 (1000/10) | 11.20 | 0.18 | 1 hr, 37° C. | 5 layers, 2.5 hrs |
|  | *67 | 1000 | 2 (1000/10) | 3.70 | 0.06 | 1 hr, 37° C. | 5 layers, 2.5 hrs |
|  | 22 | 1000 | 2 (1000/10) | 1.58 | 0.03 | 1 hr, 37° C. | 5 layers, 2.5 hrs |
| 5 | 67 | 100 | 2 (1000/20) | 26.00 | 1.30 | 1 hr, 37° C. | 10 layers, 0.75 hrs |
|  | *22 | 100 | 2 (1000/20) | 11.00 | 0.56 | 1 hr, 37° C. | 10 layers, 0.75 hrs |
|  | 7.3 | 100 | 2 (1000/20) | 2.70 | 0.10 | 1 hr, 37° C. | 10 layers, 0.75 hrs |

TABLE 3-continued

Conditions and results of Spot SELBX

| Rd | Protein (pmoles) | RNA (pmoles) | Washes[1] (μl/min) | Signal/ Noise | % Input | Incubation | Pre-adsorb[2] |
|---|---|---|---|---|---|---|---|
| 6 | 22 | 50 | 2 (1000/20) | 20.70 | 1.00 | 1 hr, 37° C. | 10 layers, 0.75 hrs |
|  | *7.3 | 50 | 2 (1000/20) | 4.00 | 0.20 | 1 hr, 37° C. | 10 layers, 0.75 hrs |
|  | 2.4 | 50 | 2 (1000/20) | 1.20 | 0.06 | 1 hr, 37° C. | 10 layers, 0.75 hrs |
| 7 | 22 | 7 | 3 (1000/50) | 24.00 | 1.30 | 1 hr, 37° C. | 10 layers, 1.5 hrs |
|  | *7.3 | 7 | 3 (1000/50) | 7.50 | 0.40 | 1 hr, 37° C. | 10 layers, 1.5 hrs |
|  | 2.4 | 7 | 3 (1000/50) | 1.50 | 0.07 | 1 hr, 37° C. | 10 layers, 1.5 hrs |
| 8 | *7.3 | 3 | 2 (1000/60) | 77.00 | 0.41 | 0.75 hr, 37° C. | 10 layers, 1.5 hrs |
|  | 2.4 | 3 | 2 (1000/60) | 8.50 | 0.04 | 0.75 hr, 37° C. | 10 layers, 1.5 hrs |
|  | 0.7 | 3 | 2 (1000/60) | 1.00 | ND | 0.75 hr, 37° C. | 10 layers, 1.5 hrs |
| 9 | *7.3 | 1 | 2 (1000/20) | 87.00 | 0.23 | 1 hr, 37° C. | 10 layers, 1.5 hrs |
|  | 2.4 | 1 | 2 (1000/20) | 4.00 | 0.01 | 1 hr, 37° C. | 10 layers, 1.5 hrs |
|  | 0.7 | 1 | 2 (1000/20) | 2.50 | 0.006 | 1 hr, 37° C. | 10 layers, 1.5 hrs |
| 10 | 7.3 | <1 (no tRNA) | 2 (1000/20) | 13.70 | ND | 0.5 hr, 37° C. | 10 layers, 1.5 hrs |
|  | 7.3 | <1 ($10^1$ tRNA)[4] | 2 (1000/20) | 10.50 | ND | 0.5 hr, 37° C. | 10 layers, 1.5 hrs |
|  | 7.3 | <1 ($10^2$ tRNA) | 2 (1000/20) | 5.00 | ND | 0.5 hr, 37° C. | 10 layers, 1.5 hrs |
|  | 7.3 | <1 ($10^3$ tRNA) | 2 (1000/20) | 1.80 | ND | 0.5 hr, 37° C. | 10 layers, 1.5 hrs |

*pool carried to next round
[1]Number of washes, volumes and duration
[2]Number of filters and duration of incubation during the background counterselection step
[3]ND, not determined
[4]Fold excess tRNA over the aptamer pool

TABLE 4

Conditions and results surface plasmon resonance biosensor (spr) SELEX.

Progress of BIA SELEX with TGFβ2

| Rd | TGFβ2, RU[1] | | | | [RNA], μM[2] | Injections (vol, μL)[3] | Fractions (min each)[4] | Fraction FW[5] | RU after SDS[6] |
|---|---|---|---|---|---|---|---|---|---|
|  | FC1 | FC2 | FC3 | FC4 | | | | | |
| 2 | 1293 | 874 | 294 | 0 | 4 | 4 (40) | 3 (5) | 3rd & SDS | ~100 |
| 3 | 1176 | 1178 | 1181 | 0 | 15 | 4 (40) | 3 (5) | 3rd & SDS | ~50–100 |
| 4 | 3010 | 2037 | 1767 | 0 | 10 | 6 (40) | 3 (5) | 3rd & SDS | ~80 |
| 5 | 5520 | 5334 | 4265 | 0 | 5 | 6 (40) | 3 (5) | 3rd & SDS | ~100–150 |
| 6 | 4075 | 3143 | 298 | 0 | 5 | 6 (40) | 3 (5) | 3rd & SDS | ~75–100 |
| 7 | 3773 | 2616 | 2364 | 0 | 2 | 6 (40) | 3 (5) | 3rd & SDS | ~330–220 |
| 8 | 2574 | 1842 | 1461 | 0 | 5 | 4 (40) | 3 (5) | 3rd & SDS | ~60–105 |
| 9 | 3180 | 2029 | 1688 | 0 | 3 | 4 (40) | 3 (5) | 3rd & SDS | ~77–114 |
| 10 | 344 | 718 | 1692 | 0 | 1 | 4 (40) | 6 (10) | 6th & SDS | ~50 |
| 11 | 217 | 675 | 386 | 0 | 5 | 2 (40) | 6 (10) | 6th & SDS | ~50–62 |

[1]Amount of TGFβ2 immobilized expressed in resonance units where 1 RU corresponds to 1 pg of protein per mm². The protein is immobilized in an area of 1.2 mm²
[2]concentration of RNA pools
[3]Number of injections and volume of each injection
[4]Number and length in min (in parentheses) of each fraction
[5]Fractions carried to the next round
[6]Amount of RNA eluted after SDS treatment expressed in response units
FC1, FC2, FC3, and FC4 designate the four flowcells of the BIA chip.

TABLE 5

Sequence isolated from round 8 of surface plasmon resonance SELEX.

| NAME[a] | SEQ ID NO. | SEQUENCE[b] | BINDING[c] |
|---|---|---|---|
| 8.1 (1) | 21 | GGGAGGACGAUGCGG UCCUCAAUG-AUCUU---------UCCUGUUUAUGCUCCC CAGACGACUCGCCCGA | FILTER |
| 8.2 (1) | 22 | GGGAGGACGAUGCGG AAGUAACGUU<u>UA</u>AGUAAAAUUCGUUCUCUCGG<u>U</u>AUUUGGC CAGACGACUCGCCCGA | TGFβ2 |
| 8.3 (14) | 23 | GGGAGGACGAUGCGG AAGUAACGUUG<u>A</u>AGUAAAAUUCGUUCUCUCGG<u>C</u>AUUUGGC CAGACGACUCGCCCGA | TGFβ2 |
| 8.5 (1) | 24 | GGGAGGACGAUGCGG UCCUAACCAUCACAAUCUCAAUUCUAUAUUUUCCCGCCC CAGACGACUCGCCCGA | NONE |
| 8.6 (1) | 25 | GGGAGGACGAUGCGG --AAACCAAAAGACCACAUCUCCAUACUCACGCUCUGCCC CAGACGACUCGCCCGA | NONE |
| 8.8 (1) | 26 | GGGAGGACGAUGCGG AUAGAUCGGUCCGAUAAGUCUUUCAUCUUUACCUGGCCCC CAGACGACUCGCCCGA | NONE |
| 8.9 (4) | 27 | GGGAGGACGAUGCGG AAGUAACGUUG<u>A</u>AGUAAAAUUCGUUCUCUCGG<u>U</u>AUUUGGC CAGACGACUCGCCCGA | TGFβ2 |
| 8.11 (1) | 28 | GGGAGGACGAUGCGG ACGAUCCUUUCCUUAACAUUUCAUCAUUUCUCCUGUGCCC CAGACGACUCGCCCGG | FILTER |
| 8.12 (1) | 29 | GGGAGGACGAUGCGG UCCAUCAACAAUCUUAUCAUUAUGUUUUUCCUUCCCGCCC CAGACGACUCGCCCGA | NONE |
| 8.13 (1) | 30 | GGGAGGACGAUGCGG UCCUCUGAGCCGAUCUUCUUCACUACUUCUUUUUCUGCCC CAGACGACUCGCCCGA | FILTER |
| 8.15 (2) | 31 | GGGAGGACGAUGCGG UUCCUCAAUUCUUCCAUCUUCAUAAUGUUUCCCUUUGCCC CAGACGACUCGCCCGA | FILTER |
| 8.18 (1) | 32 | GGGAGGACGAUGCGG UCUACCCUUUAGCAGUAUUUGUUCCAUCGUUGUUUGCCC CAGACGACUCGCCCGG | NONE |
| 8.20 (1) | 33 | GGGAGGACGAUGCGG UCUCAACGAAGAACAUCGUUGGAUACUGUUUGUCCCGCCC CAGACGACUCGCCCGA | NONE |

TABLE 5-continued

Sequence isolated from round 8 of surface plasmon resonance SELEX.

| NAME[a] | SEQ ID NO. | SEQUENCE[b] | | | BINDING[c] |
|---|---|---|---|---|---|
| 8.21 (1) | 34 | GGGAGGACGAUGCGG | UUCAGUUUCCUUCAGUUUUCGUUUCUAAUUCUUGUGUCCC | CAGACGACUCGCCCGA | FILTER |
| 8.22 (1) | 35 | GGGAGGACGAUGCGG | ----------AGCGGAUUAAUUAGUCUGACUUCUUGUCCC | CAGACGACUCGCCCGA | |
| 8.23 (1) | 36 | GGGAGGACGAUGCGG | AGACAUCUUUGUCUCGAUUAGUCAUGUUCCUUACCUGCCC | CAGACGACUCGCCCGA | NONE |
| 8.24 (1) | 37 | GGGAGGACGAUGCGG | --UCCCUAGCAAGCAGCUUCUCAUCUUAUUUUUCCGCCC | CAGACGACUCGCCCGA | |
| 8.25 (1) | 38 | GGGAGGACGAUGCGG | UGCACAGUGAUGGAUGACAUUGUAUAACGGUAUGCGUCCC | CAGACGACUCGCCCGA | |
| 8.26 (1) | 39 | GGGAGGACGAUGCGG | -ACCUAUCUUUCUUCCAAGUCAUAGUUUUACUUCCCGCCC | CAGACGACUCGCCCGA | FILTER |
| 8.28 (1) | 40 | GGGAGGACGAUGCGG | AUGAGACCUAAUCAUCGAUCCGCUAUCUAAAACCUCACCC | CAGACGACUCGCCCGA | NONE |
| 8.29 (1) | 41 | GGGAGGACGAUGCGG | UCCUCAGACAAAUCUUUCUUGAAUCUUUCCUUAACUGCCC | CAGACGACUCGCCCGA | FILTER |
| 8.31 (1) | 42 | GGGAGGACGAUGCGG | -ACCGAUUCUCCAACUUGACAUUUAUUCCUCUUUCUGCCC | CAGACGACUCGCCCGA | FILTER |
| 8.33 (1) | 43 | GGGAGGACGAUGCGG | UCCUCUGAGCCAAUCUUCUUCGCUACUUCUUUUUCUGCCC | CAGACGACUCGCCCGA | FILTER |
| 8.34 (1) | 44 | GGGAGGACGAUGCGG | AUUCUUUCUCCAACGCUUUUCACUACCUACAUUUCUGCCC | CAGACGACUCGCCCGA | FILTER |
| 8.35 (1) | 45 | GGGAGGACGAUGCGG | AUCCUAUCCUCUGAAUAUCAUUAAAUCAUCUUCUCCGCCC | CAGACGACUCGCCCGA | NONE |
| 8.36 (1) | 46 | GGGAGGACGAUGCGG | UUCAAUCAUCUUCACUCU-CAUUUCCUUUUUCCUACUCCC | CAGACGACUCGCCCGA | FILTER |
| 8.38 (1) | 47 | GGGAGGACGAUGCGG | CGAUAGAAUCUAGUCGUUCUAGAUGACUGGUACGUGCCC | CAGACGACUCGCCCGA | |
| 8.39 (1) | 48 | GGGAGGACGAUGCGG | UAGUAAUCCUUGUCUUCCAUUUCUCUUUACCCUUUUGCCC | CAGACGACUCGCCCGA | FILTER |
| 8.40 (1) | 49 | GGGAGGACGAUGCGG | ----CCCAUUAGUCCUCAUUAGU------CCCCUGUGCCC | CAGACGACUCGCCCGA | NONE |
| 8.41 (1) | 50 | GGGAGGACGAUGCGG | CAUCUUAUCCUCCAUCAGUUACUUUCGUUAUUCCCGCCC | CAGACGACUCGCCCGA | |
| 8.45 (1) | 51 | GGGAGGACGAUGCGG | UCC-AAAUCCUCUUCCCAUGUUAGCAUUCAGCCUUGUCCC | CAGACGACUCGCCCGA | |
| 8.46 (1) | 52 | GGGAGGACGAUGCGG | -UUCCGACAAUUUCCUCCACCAUUAGAUUUCUUGCUGCCC | CAGACGACUCGCCCGA | |
| 8.47 (1) | 53 | GGGAGGACGAUGCGG | UCUUGAUCCUCCUUUGUGUCUUUCUUUGUCUUCCCUGCCC | CAGACGACUCGCCCGA | |
| 8.48 (2) | 54 | GGGAGGACGAUGCGG | AAGUAACGUUG<u>A</u>AGUAAAAUUCGUUCUCUCGG<u>U</u>AUU<u>-</u>GGC | CAGACGACUCGCCCGA | TGFα2 |
| 8.49 (1) | 55 | GGGAGGACGAUGCGG | -UCCGAUCAGUUCCUUCGAUUAAUCUUCUUUCCUGCCCC | CAGACGACUCGCCCGA | |
| 8.51 (1) | 56 | GGGAGGACGAUGCGG | AAUCCUUCUCCCCUGAUGAAUAUGACCUUUUUCUUGCUCCC | CAGACGACUCGCCCGA | |
| 8.52 (1) | 57 | GGGAGGACGAUGCGG | AUGAUCUUUAAUGUCUGGUUUGAGGUCAAUGCGGGUGCCC | CAGACGACUCGCCCGA | |
| 8.56 (1) | 58 | GGGAGGACGAUGCGG | AGAUGGUACUCCAUCUCCUUUAUGUGCCCAUCGCUGCCC | CAGACGACUCGCCCGA | |
| 8.57 (1) | 59 | GGGAGGACGAUGCGG | UCCUC-GAUUCU---------AAUUUACUCCUUUUUCCCC | CAGACGACUCGCCCGA | |
| 8.61 (1) | 60 | GGGAGGACGAUGCGG | UCUACCCUUUAGCAGUAUUUGUUUCCAUCGUUGUUUGCCC | CAGACGACUCGCCCGA | |
| 8.62 (1) | 61 | GGGAGGACGAUGCGG | -CACAAUAUUCUCCUCUACUUCCACGUAUUUUCCUGUCCC | CAGACGACUCGCCCGA | |
| 8.64 (1) | 62 | GGGAGGACGAUGCGG | UCCUCAACCUUAGACUUUCAUUUCUUCAGUUCUUCUGCCC | CAGACGACUCGCCCGA | |
| 8.65 (1) | 63 | GGGAGGACGAUGCGG | UAGUGGUCUGUCAAAGGAAUAGCUAGUAGUGUUUGGUCCC | CAGACGACUCGCCCGA | |
| 8.69 (1) | 64 | GGGAGGACGAUGCGG | CAUCUUCCUUAGCAUACCAGUUUAUUCCUUUCCCUGUCCC | CAGACGACUCGCCCGA | |
| 8.71 (1) | 65 | GGGAGGACGAUGCGG | ACCUCUCAUGAUCAGCAUCUCGCGUAAUCACGGUUCACCC | CAGACGACUCGCCCGA | |
| 8.72 (1) | 66 | GGGAGGACGAUGCGG | UCCGUACUCCAUUUCCUAUUUGAUUCCUUUUCCUCUGCCC | CAGACGACUCGCCCGA | |
| 8.74 (1) | 67 | GGGAGGACGAUGCGG | AACCCACGACCUUACCUUAAUCAUGUAUUUCUCUCUGCCC | CAGACGACUCGCCCGA | |
| 8.75 (1) | 68 | GGGAGGACGAUGCGG | ------AGAUAAUGAGUGUCGGUGAUUAUAGAUGCUGCCC | CAGACGACUCGCCCGA | |
| 8.76 (1) | 69 | GGGAGGACGAUGCGG | UUCCUCAAUUCUUCCAUCUUCAUAAUGUUUCCCUUUGCCC | CAGACGACUCGCCCGA | |
| 8.79 (1) | 70 | GGGAGGACGAUGCGG | UUCCUCAAUUCUUCCAUCUUCAUAAUGUUUCCCUUUGCCC | CAGACGACUCGCCCGA | |
| 8.80 (1) | 71 | GGGAGGACGAUGCGG | UUCCU-------UCCAACGUUAUCUACUUUCU----GCCC | CAGACGACUCGCCCGA | |

[a]Names are given in the form Round 8.clone number followed by the number of clones of that sequence that were isolated ion parenthesis.
[b]-, gaps introduced to designate sequences with selected regions that are shorter than 40 bases. An attempt was made to align such sequences with other sequences but the alignment is not necessarily optimal.
Underlined bases are those that differ from ligand 14i-1 (Table 7). A = 2'-OH A; C = 2'-F C; G = 2'-OH G; U = 2'-F U.
[c]FILTER, filter-binding sequence; NONE, no binding to TGFβ2 or filters, TGFβ2, binds to TGFβ2 as well as ligand 14i-1.

TABLE 6

Conditions and results of resonant mirror (rm) optical biosensor SELEX.

Progress of IASYS SELEX with TGFβ2

| | TGFβ2, Arcsec[1] | | [RNA], $\mu M^2$ | Vol, $\mu L^3$ | Binding (min)[4] | Dissociation (min)[5] | Elution[6] |
|---|---|---|---|---|---|---|---|
| Rd | C1 | C2 | | | | | |
| 10 | 1777 | 0 | 1 | 50 | 27 | 29 | water |
| 11 | 1777 | 0 | 10 | 50 | 30 | 60 | water |
| 12 | 1777 | 0 | 10 | 50 | 60 | 150 | water |
| 13 | 1893 | 0 | 0.05 | 50 | 37 | 73 | water & SDS |
| 14 | 1721 | 0 | 3.5 | 50 | 30 | 35 | water & SDS |

[1]Amount of TGFβ2 immobilized expressed in Arcsec where 1 Arcsec is 5 pg/mm² protein. The protein is immobilized in an area of 4 mm² in cell 1 (C1).
[2]Concentration of RNA pools
[3]Volume of RNA solution used
[4]Length of binding phase in min
[5]Length of dissociation phase in min
[6]Elution used

TABLE 7

Sequences isolated from round 13 of resonant mirror SELEX

| NAME [a] | SEQ ID NO. | SEQUENCE [b] |
|---|---|---|
| 14i-1 | 72 | GGGAGGACGAUGCGG AAGUAACGUUGUAGUAAAAUUCGUUCUCUCGG-CAUUUGGC CAGACGACU-CGCCCGA |
| 13.20 (1) | 73 | GGGAGGACGAUGCGG AAGUAACGUUAUAGUAAAAUUCGUUCUCUCGG-UAUU_GGC CAGACGACU-CGCCCGA |
| 13.22 (2) | 74 | GGGAGGACGGUGCGG AAGUAACGUUGUAGUAAAAUUCGUUCUCUCGG-CGUUUGGC CAGACGACU-CGCCCGA |
| 13.24 (2) | 75 | GGGAGGACGAUGCGG AAGUAACGUUGUAGUAAAAUUCGUUCUCUCGG-CGUUUGGU CAGACGACU-CGCCCGA |
| 13.30 (1) | 76 | GGGAG_ACGAUGCGG AAGUAACGUUGUAGUAAAAUUCGUUCUCUCGG-CAUUUGGU CAGACGACU-CGCCCGA |
| 13.32 (1) | 77 | GGGAGGACGAUGCGG AAGUAACGUUGAAGUAAAAUUCGUUCUCUCUG-CGUUUGGU CAGACGACU-CGCCCGA |
| 13.34 (1) | 78 | GGGAGGACGAUGCGG AAGUAACGUUGAAGUAAAAUUCGUUCCUGG-UA_UUGGC CAGACGACU-CGCCCGA |
| 13.36 (2) | 79 | GGGAGGACGAUGCGG AAGUAACGUUGAAGUAAAAUUCGUUCUCUCGG-CAUUUGGC CAGACGACU-CGCCCGA |
| 13.40 (1) | 80 | GGGAGGACGAUGCGG AAGUAACGUUGUAGUAAAAUUCGUUCUCUUGG-CAUUU_GC CAGACGACU-CGCCCGA |
| 13.42 (1) | 81 | GGGAGGACGAUGCGG AAGUAACGUUAAAGUAAAAUUCGUUCUCUCGG-CGUUUGGC CAGACGACU-CGCCCGA |
| 13.44 (1) | 82 | GGGAGGACGAUGCGG AAGUAACGUUGAAGUAAAAUUCGUUCUCUCGG-CGUUUGGC CAGACGACU-CGCCCGA |
| 13.48 (1) | 83 | GGGAGGACGAUGCGG AAGUAACGUUGUAGUAAAAUUCGUUCUCUCGG-UAUUUGGC CAGACGACU-CGCCCGA |
| 13.50 (1) | 84 | GGGAGGACGAUGCGG AAGUAACGUUGUAGUAAAAUUCGUUCUCUUGG-UCUU_GGC CAGACGACU-CGCCCGA |
| 13.54 (1) | 85 | _GGAGGACGAUGCG_ AAGUAACGUUGUAGUAAAAUUCGUUCUCUCGGGCAUUUGG_ CAGACGACUUCGCCCGA |

[a] Names are given in the form Round 13.clone number followed by the number of clones of that sequence that were isolated.
[b] Underlined bases are those that differ from ligan 14i-1 from the filter SELEX. The sequence 14i-1 is shown at the top for comparison. A = 2'-OH A; C = 2'-F C; G = 2'-OH G; U = 2'-F U.

TABLE 8

Sequences and boundaries of TGFβ2 ligands isolated from rounds 14 and 21 of filter 21 of filter SELEX.

| NAME [a] | SEQ ID NO. | SEQUENCE [b] | Kd (nM) | Kd (nM) |
|---|---|---|---|---|
| 14i-1 | 72 | GGGAGGACGAUGCGGAAGUAACGUUGUAGUAAAAUUCG<u>UUCUCUC</u>GGCAUUUGGCCAGACGACUCGCCCGA | 10 | 230 |
| 21a-4 | 86 | GGGAGGACGA<u>U</u>GCGGCGUUGUUUAGUCGUAUGUAUAUACUAAGUCCGCUUG<u>UCCCC</u>CAGACGACUCGCCCGA | 3 | 30 |
| 21a-21 | 87 | GGGAGGACGAUGCGG-UUCA<u>GG</u>AGGUUAUUACAGAGUCUGUAUAGCUGUA<u>CUCCC</u>CAGACGACUCGCCCGA | 1 | 10 |
| region: | | 5' fixed        selected                           3' fixed | | |

[a] Names are in the form: round sequence was isolated-clone number.
[b] Boundaries are underlined. Fixed regions are in bold-faced type. Selected sequences are in plain type.
A = 2'-OH A; C = 2'-F C; G = 2'-OH G; U = 2'-F U

TABLE 9

Number of sequences isolated using the SELEX process.

| | SELEX round | | | | | |
|---|---|---|---|---|---|---|
| Sequence | 8-spr | 13-rm | 14i | 16a | 18b | 21a | TOTAL |
| 14i-1 | 0 | 0 | 75 | 2 | 0 | 0 | 77 |
| 14i-1 variants | 21 | 15 | 22 | 2 | 0 | 0 | 60 |
| 21a-4 | 0 | 0 | 0 | 0 | 0 | 3 | 3 |
| 21a-4 variants | 0 | 0 | 4 | 7 | 0 | 2 | 13 |
| 21a-21 | 0 | 0 | 0 | 1 | 11 | 38 | 50 |
| 21a-21 variants | 0 | 0 | 0 | 2 | 4 | 4 | 10 |
| unidentified | 36 | 0 | 0 | 0 | 0 | 0 | 36 |
| filter-binding | 12 | 0 | 1 | 1 | 0 | 1 | 15 |
| TOTAL | 69 | 15 | 102 | 15 | 15 | 48 | 264 |

TABLE 10

Characteristics of nucleic acid pools isolated using the SELEX method.

| Round[a] | Sequence of pool[b] | % of pool[c] | % of transformants[d] | % of clones[e] |
|---|---|---|---|---|
| 0 | random | 14i-1: < 0.03 | | |
| 6-spr | random | 14i-1: ~1 | | |
| 8-spr | slightly nonrandom | 14i-1: ~5 | | 14i-1: 30 other: 70 |
| 9-spr | nonrandom | | | |
| 9-rm | can read sequence of ligand 14i-1 | | | |
| 10-rm | can read sequence of ligand 14i-1 | | | |
| 11-rm | can read sequence of ligand 14i-1 | | | |
| 12-rm | can read variants of ligand 14i-1 sequence | | | |

TABLE 10-continued

Characteristics of nucleic acid pools isolated using the SELEX method.

| Round[a] | Sequence of pool[b] | % of pool[c] | % of transformants[d] | % of clones[e] |
|---|---|---|---|---|
| 13-rm | can read variants of ligand 14i-1 sequence | 14i-1: 10–100 | | 14i-1: 100 |
| | | 21a-21: <0.1 | | |
| 14i | | | | 14i-1: 93 |
| | | | | 21a-4: 4 |
| | | 21a-21: 0.2–0.5 | | 21a-21: 0 |
| | | | | other: 3 |
| 16a | | | | 14i-1: 27 |
| | | | | 21a-4: 47 |
| | | 21a-21: 3–100 | | 21a-21: 20 |
| | | | | other: 6 |
| 18b | | 21a-21: 3–100 | | 21a-21: 100 |
| 21a | | | 21a-4: 9 | 21a-4: 10 |
| | | 21a-21: 3–100 | 21a-21: 90 | 21a-21: 84 |
| | | | other: 1 | other: 6 |

[a]spr, from surface plasmon resonance biosensor SBLEX; rm, from resonant mirror optical biosensor SELEX.
[b]Determined by primer extension of bulk nucleic acid pools with 3'N7 primer.
[c]Determined by RT-PCR of bulk nucleic acid pools with a ligand-specific primer.
[d]Determined by PCR of individual transformants with a ligand-specific primer.
[e]Determined by sequencing of clones. Includes sequence variants of ligands.

TABLE 11

Truncates of human TGFβ2 nucleic acid ligand 21a-21.

| NAME | SEQUENCE[a] | SEQ ID NO. |
|---|---|---|
| 21a-21 | GGGAGGACGAUGCGGUUCAGGAGGUUAUUACAGAGUCUGUAUAGCUGUA<u>CUCCCC</u>AGACGACUCGCCCGA | 87 |
| 21a-21(U6G) | GGGAGGACGAUGCGGUUCAGGAGG<u>G</u>UAUUACAGAGUCUGUAUAGCUGUACUCCCCAGACGACUCGCCCGA | 88 |
| 21a-21Δ5' | GGUUCAGGAGGUUAUUACAGAGUCUGUAUAGCUGUACUCCCCAGACGACUCGCCCGA | 89 |
| 21a-21Δ3' | GGGAGGACGAUGCGGUUCAGGAGGUUAUUACAGAGUCUGUAUAGCUGUACUCCCCA | 90 |
| 21a-21Δ5',3' | GGUUCAGGAGGUUAUUACAGAGUCUGUAUAGCUGUACUCCCCA | 91 |
| 21a-21(ML-94) | GGAGGUUAUUACAGAGUCUGUAUAGCUGUACUCCCC | 92 |
| 21a-21(ML-95) | GGAGGUUAUUACAGAGUCUGUAUAGCUGUACUCC | 93 |
| 21a-21(ML-96) | GGAGGUUAUUACAGAGUCUGUAUAGCUGUA | 94 |
| 21a-21(ML-97) | GGAGGUUAUUACAGAGUCUGUAUAGC | 95 |
| 21a-21(ML-99) | GGAGGUUAUUACAGAGUCUGUAUAGC    CUCC | 96 |
| 21a-21(ML-101) | GGAGGUUAUU   AGAGUCU   AUAGCUGUACUCC | 97 |
| 21a-21(ML-102) | GGAGGUUAUU   AGAGUCU   AUAGC    CUCC | 98 |
| 21a-21(ML-103) | GGAGGUUAUUACAGAGUCUGUAUAGCUGUACUC | 99 |
| 21a-21(ML-104) | GGAGGUUAUUACAGAGUCUGUAUAGCUGUACU | 100 |
| 21a-21(ML-105) | GGAGGUUAUUACAGAGUCUGUAUAGCUGUAC | 101 |
| 21a-21(ML-114) | GGAGGUUAUUACAGAGUCUGUAUAGC GUACUCC | 102 |
| 21a-21(ML-115) | GGAGGUUAUUACAGAGUCUGUAUAGCUGU CUCC | 103 |
| 21a-21(ML-116) | GGAGGUUAUUACAGAGUCUGUAUAGCU   ACUCC | 104 |
| 21a-21(ML-118) | GGAGGUUAU ACAGAGUCUGUAUAGCUGUACUCC | 105 |
| 21a-21(ML-120) | GGAGGUUAUUACAGA UCUGUAUAGCUGUACUCC | 106 |
| 21a-21(ML-122) | GGAGGUUAUUACA AGU UGUAUAGCUGUACUCC | 107 |
| 21a-21(ML-128) | GGAGGUUAUUACAGAGU UGUAUAGCUGUACUCC | 108 |
| 21a-21(ML-130) | GG GGUUAUUACAGAGUCUGUAUAGCUGUAC CC | 109 |
| 21a-21(ML-132) | GGAGGUUAUUAC GAGUCUGUAUAGC GUACUCC | 110 |
| 21a-21(ML-134) | GGAGA UAUUACAGAGUCUGUAUAGCUGUACUCC | 111 |
| 21a-21(ML-136) | GG GGUUAUU CAGAGUCUGUAUAGCUG AC CC | 112 |
| 21a-21(ML-138) | GG GGUUAUUA AGAGUCUGUAUAGCU UAC CC | 113 |
| NX22283 | GGAGGUUAUUACAGAGUCUGUAUAGCUGUACUCCCC [3'T] | 114 |
| NX22284 | GGAGGUUAUUACAGAGUCUGUAUAGCUGUACUCC    [3'T] | 115 |
| NX22285 | GGAGGUUAUUACAGAGUCUGUAUAGCUGUACUCCCCA | 116 |
| NX22286 | GGAGGUUAUUACAGAGUCUGUAUAGCUGUA | 117 |
| NX22301 | GAGGUUAUUACAGAGUCUGUAUAGCUGUACUCC    [3'T] | 118 |
| NX22302 | AGGUUAUUACAGAGUCUGUAUAGCUGUACUCC    [3'T] | 119 |
| NX22303 | GGUUAUUACAGAGUCUGUAUAGCUGUACUCC    [3'T] | 120 |
| NX22323 | PEG-GGAGGUUAUUACAGAGUCUGUAUAGCUGUACUCC    [3'T] | 121 |

| NAME | BINDING[b] | LENGTH[c] | BIOACTIVITY[d] |
|---|---|---|---|
| 21a-21 | 0.5 | 70 | 1 |
| 21a-21(U6G) | 250 | 34 | |
| 21a-21Δ5' | 0.5 | 56 | |
| 21a-21Δ3' | 100 | 56 | |
| 21a-21Δ5',3' | 0.5 | 42 | 1 |
| 21a-21(ML-94) | 0.5 | 36 | |

TABLE 11-continued

Truncates of human TGFβ2 nucleic acid ligand 21a-21.

| | | | |
|---|---|---|---|
| 21a-21(ML-95) | 1 | 34 | |
| 21a-21(ML-96) | 1000 | 30 | |
| 21a-21(ML-97) | 1000 | 26 | |
| 21a-21(ML-99) | 1000 | 30 | |
| 21a-21(ML-101) | 1000 | 30 | |
| 21a-21(ML-102) | 1000 | 26 | |
| 21a-21(ML-103) | 50 | 33 | |
| 21a-21(ML-104) | 70 | 32 | |
| 21a-21(ML-105) | 1000 | 31 | |
| 21a-21(ML-114) | 1000 | 33 | |
| 21a-21(ML-115) | 1000 | 33 | |
| 21a-21(ML-116) | 1000 | 32 | |
| 21a-21(ML-118) | 1000 | 33 | |
| 21a-21(ML-120) | 1000 | 33 | |
| 21a-21(ML-122) | 1000 | 32 | |
| 21a-21(ML-128) | 1000 | 33 | |
| 21a-21(ML-130) | 2 | 32 | |
| 21a-21(ML-132) | 1000 | 32 | |
| 21a-21(ML-134) | 10 | 33 | |
| 21a-21(ML-136) | 10000 | 30 | |
| 21a-21(ML-138) | 10000 | 30 | |
| NX22283 | 0.6 | 36 | 0 |
| NX22284 | 1 | 34 | 1 |
| NX22285 | 2 | 37 | |
| NX22286 | 130 | 30 | >20 |
| NX22301 | 1 | 33 | 2 |
| NX22302 | 100 | 32 | |
| NX22303 | >100 | 31 | >100 |
| NX22323 | nt | 34 | 3 |

[a]The fixed regions are indicated by bold-faced letters. The point mutant in 21a-21(U6G) is underlined and in bold type. A = 2'-OH A; C = 2'-F C; G = 2'-OH G; U = 2'-F U The italicized G at the 5' end of the 5' RNase H cleavage products indicates that ~50% of the time cleavage leaves 2 G's and 50% of the time one G is left. The boundaries in 21a-21 are underlined
[b]Binding is expressed as the ratio of the $K_d$ of ligand/$K_d$ of NX22284. The $K_d$ of NX22284 is ~2 nM.
[c]Length is given in bases.
[d]Bioactivity is expressed as the ratio of the $K_i$ of ligand/$K_i$ of NX22284. The $K_i$ of NX22284 is ~10 nM.

TABLE 12

Alignment of human transforming growth factor β amino acid sequences.

| | | SEQ ID NO. |
|---|---|---|
| TGFβ1: | ALDTNYCFSS TEKNCCVRQL YIDFRKDLGW KWIHEPKGYH ANFCLGPCPY IWSLDTQYSK 60 | 122 |
| TGFβ2: | ALDAAYCFRN VQDNCCLRPL YIDFKRDLGW KWIHEPKGYN ANFCAGACPY LWSSDTQHSR 60 | 123 |
| TGFβ3: | ALDTNYCFRN LEENCCVRPL YIDFRQDLGW KWVHEPKGYY ANFCSGPCPY LRSADTTHST 60 | 124 |
| TGFβ2 specific: | AA    VQD  L      KR         N   A A      S       R | |
| TGFβ1: | VLALYNQHNP GASAAPCCVP QALEPLPIVY YVGRKPKVEQ LSNMIVRSCK CS 112 | 125 |
| TGFβ2: | VLSLYNTINP EASASPCCVS QDLEPLTILY YIGKTPKIEQ LSNMIVKSCK CS 112 | 126 |
| TGFβ3: | VLGLYNTLNP EASASPCCVP QDLEPLTILY YVGRTPKVEQ LSNMVVKSCK CS 112 | 127 |
| TGFβ2 specific: |  S    I       S           I K   I | |

TABLE 13

Truncates of human TGFβ2 nucleic acid ligand 1 14i-1.

| NAME | SEQUENCE[a] | SEQ ID NO. | BIND-ING[b] | LENGTH |
|---|---|---|---|---|
| 14i-1 | <u>GGGA</u>GGACGAUGCGGAAGUAACGUUGUAGUAAAAUUCG<u>UUCUCUC</u>GGCAUUUGCCAGACGACUCGCCCGA | 72 | 1 | 71 |
| 14i-1Δ5'd | GGAAGUAACGUUGUAGUAAAAUUCGUUCUCUCGGCAUUUGCCCAGACGACUCGCCCGA | 128 | >100 | 56 |
| 14i-1Δ3'd | GGGAGGACGAUGCGGAAGUAACGUUGUAGUAAAAUUCGUUCUCUCGGCAUUUGCCA | 129 | 3 | 57 |
| 14i-1Δ5,3'd | GGAAGUAACGUUGUAGUAAAAUUCGUUCUCUCGGCAUUUGCCA | 130 | >100 | 42 |
| 14i-1t5-41 | gGGAgGAUGCGGAAGUAACGUUGUAGUAAAAUUCcUUC | 131 | 1 | 38 |
| 14i-1t5-38 | gGGAgGAUGCGGAAGUAACGUUGUAGUAAAAUUCc | 132 | >100 | 35 |
| 14i-1t5-35 | gGGAgGAUGCGGAAGUAACGUUGUAGUAAAAU | 133 | >100 | 32 |
| 14i-1 (ML-86) | gGGAgGAUGCGGAAGUAACGUUGUAGU       UCcUUC | 134 | >100 | 33 |
| 14i-1 (ML-87) | gGGAgGAUGCGGAAGUAACGUUGUAGU | 135 | >100 | 27 |

TABLE 13-continued

Truncates of human TGFβ2 nucleic acid ligand 1 14i-1.

| NAME | SEQUENCE[a] | SEQ ID NO. | BIND-ING[b] | LENGTH |
|---|---|---|---|---|
| 14i-1 (ML-89) | gGgaGgAGUAACGUUGUAGU | 136 | >100 | 20 |

[a]Lowercase letters indicate bases not found at that position in the full length ligand that were added or changed to maintain transcriptional efficiency. Boundaries are underlined. The fixed regions are in bold-faced type. The italicized G at the 5'end of the 5'RNase H cleavage products indicates that ~50% of the time cleavage leaves 2 G's and 50% of the time one G is left. A=2'-OH A; C = 2'-F C; G = 2'-OH G; U = 2'-F
[b]Binding is expressed as the ratio of $K_d$ (ligand)/Kd (14i-1). The $K_d$ of 14i-I is ~10 nM.
[c]Length is in bases.
[d]Produced by RNase H digestion.

TABLE 14

Truncates of human TGFβ2 nucleic acid ligand 21a-4.

| Name | Sequence[a] | SEQ ID NO. | Bind-ing[b] | Length[c] |
|---|---|---|---|---|
| 21a-4 | GGGAGGACGAUGCGGCGUUGUUUAGUCGUAUGUAUAUACUAAGUCCGCUUGUCCCCAGACGACUCGCCCGA | 86 | 1 | 71 |
| 21a-4Δ5'[d] | GGCGUUGUUUAGUCGUAU-GUAUAUACUAAGUCCGCUUGUCCCCAGACGACUCGCCCGA | 137 | >100 | 56 |
| 21a-4Δ3'[d] | GGGAGGACGAUGCGGCGUUGUUUAGUCGUAUGUAUAUACUAAGUCCGCUUGUCCCCA | 138 | 1 | 57 |
| 21a-4Δ5', 3'[d] | GGCGUUGUUUAGUCGUAUGUAUAUACUAAGUCCGCUUGUCCCCA | 139 | >100 | 42 |
| 21a-4 (ML-91) | ggGgaGCGGCGUUGUUUAGUCGUAUGUAUAUACUAAGUCCGCUU | 140 | 1 | 44 |
| 21a-4 (ML-92) | ggGgaGCGGCGUUGUUU gaaa AGUCCGCUU | 141 | >100 | 27 |
| 21a-4 (ML-108) | ggGgaGCGGCGUUGUUU CGUAUGUAUAU AAGUCCGCUU | 142 | >100 | 38 |
| 21a-4 (ML-109) | ggGgaGCGGCGUUGUUU AUGUAU AAGUCCGCUU | 143 | >100 | 33 |
| 21a-4 (ML-110) | ggGgaGCGGCGUUGUUUAGUCGUAUGUAUAUACUAAGUCCGC | 144 | 1 | 42 |
| 21a-4 (ML-111) | ggGgaGCGGCGUUGUUUAGUCGUAUGUAUAUACUAAGU | 145 | 30 | 38 |

[a]Lowercase letters indicate bases not found at that position in the full length ligand. Underlining indicates boundary positions. The fixed region sequences are indicated in bold-faced lettering. The italicized G at the 5' end of the 5'RNase H cleavage products indicates that ~50% of the time cleavage leaves 2 Gs and 50% of the time one G is left. A = 2'-OH A; C = 2'-F C; G = 2'-OH G; U = 2-FU
[b]Binding is expressed as the ratio of $K_d$ (ligand)/$K_d$(21a-4). The $K_d$ of 21a-4 is ~3 nM.
[c]Length is expressed in bases.
[d]These ligands were generated by RNAse H digestion of 21a-4.

TABLE 15

Biased SELEX conditions and results.

| Round[a] | [RNA][b], nM | [TGFβ2], nM | RNA[b]/protein | [Competitor] | % Bound | % Background | Bound/background | Kd (nM)[c] |
|---|---|---|---|---|---|---|---|---|
| 34N7.21a-21 round 0 nucleic acid | | | | | | | | 870 |
| 1a | 100 | 150 | 7 | 0 | 1.4 | 1.4 | 1.0 | 395 |
| 2a | 450 | 300 | 1.5 | 0 | 1.7 | 1.0 | 1.7 | 186 |
| 3a | 10 | 50 | 0.2 | 0 | 17.5 | 1.0 | 17.5 | 25 |
| 4a | 50 | 10 | 5 | 0 | 11.0 | 0.9 | 12.3 | 17 |
| 4b | 50 | 10 | 5 | 333 nM NX22284 | 2.2 | 1.3 | 1.7 | 8 |
| 5a | 8 | 1 | 8 | 0 | 1.4 | 0.9 | 1.5 | 1 |
| 5b | 8 | 1 | 8 | 100 nM NX22284 | 0.8 | 0.7 | 1.1 | 17 |
| 6a | 4 | 0.5 | 8 | 0 | 2.9 | 2.9 | 1.0 | 1 |
| 6b | 6 | 0.5 | 12 | 100 nM NX22284 | 1.8 | 1.3 | 1.4 | 1 |
| 7a | 5 | 0.25 | 20 | 0 | 0.5 | 0.14 | 3.4 | 1 |
| 7b | 5 | 0.25 | 20 | 200 nM NX22284 5 nM tRNA | 0.15 | 0.1 | 1.5 | 0.5 |
| 8a | 1 | 0.05 | 20 | 0 | 1.05 | 1.1 | 0.9 | 1 |
| 8b | 1 | 0.05 | 20 | 100 nM NX22284 5 nM tRNA | 0.6 | 0.5 | 1.2 | 3 |
| 9a | 125 | 1 | 125 | 0 | 0.6 | 0.5 | 1.2 | nd |
| 9b | 0.9 | 0.01 | 90 | 0 | 0.15 | 0.14 | 1.0 | nd |

[a]a series, without competitor; b series, with competitors
[b]nucleic acid ligand library
[c]nd, not determined

TABLE 16

Nucleic acid ligands isolated from round 5a of a human TGFβ2 biased SELEX.

| NAME[a] | 5' FIXED | SELECTED[b] | 3' FIXED | SEQ ID NO. | CHANGES[c] | BINDING[d] |
|---|---|---|---|---|---|---|
| putative structural element: | | S1   B   S2   L   S2 S1 | | | | |
| 21a-21: | GGGAGGACGAUGCGG | UUCAGGAGGUUAUUACAGAGUCUGUAUAGCUGUACUCCC | CAGACGACUCGCCCGA | 72 | 0 | 1.0 |
| 1: (2) | GGGAGGACGAUGCGG | GGUGAUUAUUACAGAGUAUGUAUAGCUGUACCCC | CAGACGACUCGCCCGA | 146 | 4 | 0.8 |
| 2: (1) | GGGAGGACGAUGCGG | AGGCUUAUUAGAGAGUCUGUAUAGCUCUAGCCC | CAGACGACUCGCC-GA | 147 | 7 | 0.6 |
| 4: (1) | GGGAGGACGAUGCGG | GGAGGGUAUUACAGAGUAUGUAUAGCUGUACUCC | CAGACGACUCGCCCGA | 148 | 2 | 1.4 |
| 6: (2) | GGGAGGACGAUGCGG | GGAGGUUAUUAUAGAGUCUGUAUAGCUAUACCCC | CAGACGACUCGCCGA | 149 | 3 | 1.6 |
| 7: (1) | GGGAGGACGAUGCGG | GAGGGUUAUUAUAGAGUCUGCAUAGCUAUACCCC | CAGACGACUCGCCCGA | 150 | 5 | 0.3 |
| 9: (1) | GGGAGGACGAUGCGG | UGAGAGUAUUACGGAGUAUGUAUAGCCGUACCCC | CAGACGACUCGCCCGA | 151 | 7 | 0.3 |
| 10:(1) | GGGAGGACGAUGCGG | GGGCAUUAUUUCAGAGUCUGUAUAGCUGUAGCCC | CAGACGACUCGCCCGA | 152 | 6 | 0.3 |
| 11:(2) | GGGAGGACGAUGCGG | GCGGAUUAUCACAGAGUAUGUAUAGCUGUGCCGC | CAGACGACUCGCCCGA | 153 | 8 | 0.4 |
| 13:(1) | GGGAGGACGAUGCGG | UGUGAAUAUUAGAGAGUCUGUAUAGCUCUACCCC | CAGACGACUCGCCCGA | 154 | 7 | 0.2 |
| 14:(1) | GGGAGGACGAUGCGG | CGGGAUUAUUACUGAGUCUGUAUAGCAGUACCCC | CAGACGACUCGCCCGA | 155 | 6 | 0.4 |
| 15:(1) | GGGAGGACGAUGCGG | GUGGAAUAUUACGGAGUAUGUAUAGCCGUACUCC | CAGACGACUCGCCCGA | 156 | 6 | 0.4 |
| 17:(1) | GGGAGGACGAUGCGG | GGGGACUAUUAGUGAGUCUGUAUAGCACUACCCC | CAGACGACUCGCCCGA | 157 | 8 | 0.8 |
| 18:(1) | GGGAGGACGAUGCGG | GUGGAUUAUUACAGCGUCUGUAUAUCUGUACCCC | CAGACGACUCGCCCGA | 158 | 6 | 1.0 |
| 19:(2) | GGGAGGACGAUGCGG | GCAGGUUAUUACAGAGUCUGUAUAGCUGUACUGC | CAGACGACUCGCCCGA | 159 | 6 | 1.0 |
| 20:(1) | GGGAGGACGAUGCGG | GGUAGAUAUCACUGAGUCUGUAUAGCAGUGUCCC | CAGACGACUCGCCCGA | 160 | 9 | 5.7 |
| 21:(2) | GGGAGGACGAUGCGG | AGGGAUUAUUACAGAGUCUGUAUAGCUGUACCCC | CAGACGACUCGCCCGA | 161 | 4 | 0.7 |
| 22:(4) | GGGAGGACGAUGCGG | GUGGAUUAUUACAGAGUCUGUAUAGCUGUACCCC | CAGACGACUCGCCCGA | 162 | 4 | 1.1 |
| 25:(1) | GGGAGGACGAUGCGG | GGGCUUAUUACAGAGUCUGUAUAGCUGUAGCCC | CAGACGACUCGCCCGA | 163 | 4 | 1.0 |
| 26:(1) | GGGAGGACGAUGCGG | GGUGGUUAUUACACAGUAUGUAUAGGUGUACCCC | CAGACGACUCGCCCGA | 164 | 4 | 3.1 |
| 28:(1) | GGGAGGACGAUGCGG | AGGGAAUUACAGAGUAUGUAUAGCUGUACCCC | CAGACGACUCGCCCGA | 165 | 6 | 1.0 |
| 29:(1) | GGGAGGACGAUGCGG | GGAGUUUAUUACAGCGUCUGUAUAUCUGUAGCCC | CAGACGACUCGCCCGA | 166 | 5 | 1.0 |
| 30:(1) | GGGAGGACGAUGCGG | UGAGGUUAUUACAGAGUCUGUAUAGCUGUACUCC | CAGACGACUCGCCCGA | 167 | 1 | 2.4 |
| 34:(1) | GGGAGGACGAUGCGG | GGUGGUUAUUAGAGAGUCUGUAUAGCUCUACGCC | CAGACGACUCGCCCGA | 168 | 4 | 1.7 |
| 35:(1) | GGGAGGACGAUGCGG | GGGGAGUAUUAAAGAGUCUGUAUAGCUUUACCCC | CAGACGACUCGCCCGA | 169 | 6 | 0.8 |
| 36:(1) | GGGAGGACGAUGCGG | GGAGGAUAUUAUAGAGUCUGUAUAGCUAUACCCC | CAGACGACUCGCCCGA | 170 | 4 | 1.9 |
| invariant: | | UAU    GU  UG AUA        C | | | | |

[a] Number of clones isolated for each sequence is indicated in parentheses.
[b] Nucleotides that differ from the starting sequence are shown in bold-faced lettering. A = 2'-OH A; C = 2'-F C; G = 2'-OH G; U = 2'-F U Putative structural elements: S1, stem 1; B, bulge; S2, stem 2; L, loop. The sequence of ligand 21a-21 is shown at the top for comparison.
[c] Number of changes from starting sequence.
[d] Binding is expressed as $K_d$ (ligand)/$K_d$ (21a-21). The $K_d$ of ligand 21a-21 is about 1 nM.

TABLE 17

Highest and lowest affinity TGFβ2 nucleic acid ligands from biased SELEX.

| NAME | 5' FIXED | SELECTED[a] | 3' FIXED | SEQ ID NO. | BIND-ING[b] | CHANGES[c] |
|---|---|---|---|---|---|---|
| HIGHEST AFFINITY LIGANDS: | | | | | | |
| 13: | GGGAGGACGAUGCGG | UGUGAAUAUUAGAGAGUCUGUAUAGCUCUACCCC | CAGACGACUCGCCCGA | 154 | 0.2 | 7 |
| 14: | GGGAGGACGAUGCGG | CGGGAUUAUUACUGAGUCUGUAUAGCAGUACCCC | CAGACGACUCGCCCGA | 155 | 0.4 | 6 |
| 21: | GGGAGGACGAUGCGG | AGGGAUUAUUACAGAGUCUGUAUAGCUGUACCCC | CAGACGACUCGCCCGA | 161 | 0.7 | 4 |
| 35: | GGGAGGACGAUGCGG | GGGGAGUAUUAAAGAGUCUGUAUAGCUUUACCCC | CAGACGACUCGCCCGA | 169 | 0.8 | 6 |
| putative structural elements: | | S1    B    S2    L    S2 S1 | | | | |
| 21a-21: | GGGAGGACGAUGCGGUUCAGGAGGUUAUUACAGAGUCUGUAUAGCUGUACUCCC | | CAGACGACUCGCCCGA | 72 | 1.0 | 0 |
| LOWEST AFFINITY LIGANDS: | | | | | | |
| 36: | GGGAGGACGAUGCGG | GGAGGAUAUUAUAGAGUCUGUAUAGCUAUACCCC | CAGACGACUCGCCCGA | 170 | 2.0 | 4 |
| 30: | GGGAGGACGAUGCGG | UGAGGUUAUUACAGAGUCUGUAUAGCUCUACUCC | CAGACGACUCGCCCGA | 167 | 2.4 | 1 |
| 26: | GGGAGGACGAUGCGG | GGUGGUUAUUACACAGUAUGUAUAGGUGUACCCC | CAGACGACUCGCCCGA | 164 | 3.1 | 4 |
| 6: | GGGAGGACGAUGCGG | GGAGGUUAUUAUAGAGUCUGUAUAGCUAUACCCC | CAGACGACUCGCCCGA | 149 | 3.3 | 3 |
| 20: | GGGAGGACGAUGCGG | GGUAGAUAUCACUGAGUCUGUAUAGCAGUGUCCC | CAGACGACUCGCCCGA | 160 | 5.7 | 9 |
| invariant: | | UAU    GU UG AUA    C | | | | |

[a]Nucleotides that differ from the starting sequence are shown in bold-faced lettering. A = 2'-OH A; C = 2'-F C; G = 2'-OH G; U = 2'-F U Putative structural elements: S1, stem 1; B, bulge; S2, stem 2; L, loop.
[b]Binding is expressed as $K_d$ (ligand)/$K_d$ (21a-21). The $K_d$ of 21a-21 is 1 nM
[c]Number of changes from starting sequence.

TABLE 18

Substitution of 2'-OH purines with 2'-OCH₃ purines in NX22284 ligand.

| NAME | SEQUENCE[a] | SEQ ID NO. | BINDING[b] | LENGTH[c] | BIOACTIVITY[d] |
|---|---|---|---|---|---|
| NX22284 | GGAGGUUAUUACAGAGUCUGUAUAGCUGUACUCC[3'T] | 115 | 1 | 34 | 1 |
| NX22304 | ggaggUUaUUaCagagUCUgUaUagCUguaCuCC[3'T] | 171 | >100 | 34 | >100 |
| NX22355 | GGAGGUUaUUaCagagUCUgUaUagCUgUaCUCC[3'T] | 172 | >100 | 34 | >100 |
| NX22356 | ggagGUUAUUACAGAGUCUGUAUAGCUGUACUCC[3'T] | 173 | 1 | 34 | 1 |
| NX22357 | GGAGgUUaUUaCAGAGUCUGUAUAGCUGUACUCC[3'T] | 174 | 2 | 34 | 10 |
| NX22358 | GGAGGUUAUUaCagagUCUGUAUAGCUGUACUCC[3'T] | 175 | 1 | 34 | 1 |
| NX22359 | GGAGGUUAUUACAGAGUCUgUaUaGCUGUACUCC[3'T] | 176 | >100 | 34 | >30 |
| NX22360 | GGAGGUUAUUACAGAGUCUGUAUAGcUgUaCUCC[3'T] | 177 | 1 | 34 | 1 |
| NX22374 | GGAGGUUAUUACAGAGUCUgUAUAGCUGUACUCC[3'T] | 178 | 25 | 34 | >100 |
| NX22375 | GGAGGUUAUUACAGAGUCUGUaUAGCUGUACUCC[3'T] | 179 | >100 | 34 | >300 |
| NX22376 | GGAGGUUAUUACAGAGUCUGUAUaGCUGUACUCC[3'T] | 180 | 50 | 34 | >100 |
| NX22377 | ggaggUUaUUaCAGAGUCUGUAUAGcUgUaCUCC[3'T] | 181 | 1 | 34 | 1 |
| NX22383 | ggaggUUaUUaCagagUCUGUAUagCUgUaCUCC[3'T] | 182 | 500 | 34 | >100 |
| NX22384 | ggaggUUaUUaCagagUCUgUaUagCUgUaCUCC[3'T] | 183 | 10000 | 34 | >100 |
| NX22417 | ggaggUUaUUaCagagUCUGUAUAGCUgUaCUCC[3'T] | 184 | 1 | 34 | 10 |
| NX22420 | ggaggUUAUUACagagUCUGUAUAGCUgUaCUCC[3'T] | 185 | 1 | 34 | 1 |
| NX22421 | ggagGUUAUUACagagUCUGUAUAGCUgUaCUCC[3'T] | 186 | 2 | 34 | 1 |
| NX22426 | ggaga-UAUUaCagagUCUGUAUAGcUgUaCUCC[3'T] | 187 | 1 | 33 | 25 |
| NX22427 | gg-ggUAUUaCagagUCUGUAUAGCUgUaC-CC[3'T] | 188 | 0.3 | 32 | 0.7 |

[a]A, 2'-OH A; C, 2'-F C; G, 2'-OH G; U, 2'-F U; a, 2'-OCH₃A; g, 2'-OCH₃G. [3'T] signifies a 3', 3'dT cap.
[b]Binding is expressed as the ratio of the $K_d$ of ligand/$K_d$ of NX22284. The $K_d$ of NX22284 is ~1 nM.
[c]Length is given in bases.
[b]Bioactivity is expressed as the ratio of the $K_i$ of ligand/$K_i$ of NX22284. The $K_i$ of NX22284 is ~10 nM.

TABLE 19

Truncates and 2'-OCH₃ purine modifications of nucleic acid ligand #13 from a biased SELEX.

| NAME | SEQUENCE[a] | SEQ ID NO. | BINDING[b] | LENGTH[c] | BIOACTIVITY[d] |
|---|---|---|---|---|---|
| NX22385 | UGUGAAUAUUAGAGAGUCUGUAUAGCUCUACCCC[3'T] | 189 | 0.4 | 34 | 4 |
| NX22386 | UgUgaAUaUUaGagagUCUGUAUAgCUCUaCCCC[3'T] | 190 | 3000 | 34 | >100 |
| NX22387 | UgUgaaUaUUagagagUCUgUAUagCUCUaCCCC[3'T] | 191 | 3000 | 34 | 30 |
| NX22424 | UgUgAAUAUUaGagagUCUGUAUAgCUCUaCCCC[3'T] | 192 | 0.6 | 34 | >100 |
| NX22425 | UgUgaaUAUUagagagUCUGUAUAgCUCUaCCCC[3'T] | 193 | 1.5 | 34 | >100 |

[a]A, 2'-OH A; C, 2'-F C; G, 2'-OH G; U, 2'-F U; a, 2'-OCH₃ A; g, 2'-OCH₃ G. [3'T] signifies a 3', 3' dT cap.
[b]Binding is expressed as the ratio of the $K_d$ of ligand/$K_d$ of NX22284. The $K_d$ of NX22284 is 2 nM.
[c]Length is given in bases.
[b]Bioactivity is expressed as the ratio of the $K_i$ of ligand/$K_i$ of NX22284. The $K_i$ of NX22284 is 10 nM.

TABLE 20

Pharmacokinetic properties of NX22323 in rats using a noncompartmental analysis.

| Parameter | Units | Estimate |
|---|---|---|
| Cmax | (μg/mL) | 27.1 |
| AUClast | ((μg*min)/mL) | 3028.0 |
| AUCINF | ((μg*min)/mL) | 3058.0 |
| Beta t1/2 | (min) | 630.9 |
| Cl | (mL/(min*kg)) | 0.33 |
| MRTINF | (min) | 350.4 |
| Vss | (mL/kg) | 115.0 |
| Vz | (mL/kg) | 298.0 |

TABLE 21

Pharmacokinetic properties of NX22323 in rats using a compartmental analysis.

| Parameter | Units | Estimate | StdError | % Error |
|---|---|---|---|---|
| Cmax | (μg/mL) | 16.3 | 3.3 | 20.2 |
| AUCINF | ((μg*min)/mL) | 2486 | 274 | 11.0 |
| Alpha-t1/2 | (min) | 63.5 | 19.1 | 30.2 |
| Beta-t1/2 | (min) | 467.2 | 83.2 | 17.8 |
| A | (μg/mL) | 14.63 | 3.21 | 21.9 |
| B | (μg/mL) | 1.70 | 0.84 | 49.1 |
| Cl | (mL/(min*kg)) | 0.402 | 0.044 | 11.0 |
| MRTINF | (min) | 360.3 | 35.6 | 9.9 |
| Vss | (mL/kg) | 144.9 | 23.1 | 15.9 |

TABLE 22

Binding and inhibitory activity of 2'-Omethyl- and Pegyl-modifications of lead TGFα1 truncate ligand CD70

| | | SEQ ID NO. | Binding | Bioactivity |
|---|---|---|---|---|
| ChD70 | GGGUGCCUUUUGCCUAGGUUGUGAUUUGUAACCUUCUGCCCA | 216 | +++ | +++ |
| ChD70-m1 | gggUgCCUUUUGCCUAGGUUGUGAUUUGUAACCUUCUGCCCA | 194 | + | |
| ChD70-m2 | GGGUGCCUUUUgCCUaggUUGUGAUUUGUAACCUUCUGCCCA | 195 | ++ | |
| ChD70-m3 | GGGUGCCUUUUGCCUAGGUUgUgaUUUgUAACCUUCUGCCCA | 196 | +++ | |
| ChD70-m4 | GGGUGCCUUUUGCCUAGGUUGUGAUUUGUaaCCUUCUgCCCa | 197 | ++ | |
| ChD70-m5 | gGGUGCCUUUUGCCUAGGUUgUgaUUUgUAACCUUCUGCCCA | 198 | +++ | |
| ChD70-m6 | GgGUGCCUUUUGCCUAGGUUgUgaUUUgUAACCUUCUGCCCA | 199 | +++ | |
| ChD70-m7 | GGgUGCCUUUUGCCUAGGUUgUgaUUUgUAACCUUCUGCCCA | 200 | +++ | |
| ChD70-m8 | GGGUgCCUUUUGCCUAGGUUgUgaUUUgUAACCUUCUGCCCA | 201 | + | |
| ChD70-m9 | GGGUGCCUUUUgCCUAGGUUgUgaUUUgUAACCUUCUGCCCA | 202 | + | |
| ChD70-m10 | GGGUGCCUUUUGCCUaGGUUgUgaUUUgUAACCUUCUGCCCA | 203 | +++ | |
| ChD70-m11 | GGGUGCCUUUUGCCUAgGUUgUgaUUUgUAACCUUCUGCCCA | 204 | +++ | |
| ChD70-m12 | GGGUGCCUUUUGCCUAGgUUgUgaUUUgUAACCUUCUGCCCA | 205 | +++ | |
| ChD70-m13 | GGGUGCCUUUUGCCUAGGUUgUgaUUUgUaACCUUCUGCCCA | 206 | +++ | |
| ChD70-m14 | GGGUGCCUUUUGCCUAGGUUgUgaUUUgUAaCCUUCUGCCCA | 207 | +++ | |
| ChD70-m15 | GGGUGCCUUUUGCCUAGGUUgUgaUUUgUAACCUUCUgCCCA | 208 | +++ | |
| ChD70-m16 | GGGUGCCUUUUGCCUAGGUUgUgaUUUgUAACCUUCUGCCCa | 209 | +++ | |
| ChD70-m17 | gggUGCCUUUUGCCUaggUUgUgaUUUgUaaCCUUCUGCCCa3'-3'U | 210 | +++ | +++ |
| ChD70-m18 | gggUGCCUUUUGCCUaggUUgUgaUUUgUaACUUCUGCCCa3'-3'U | 211 | +++ | |
| ChD70-m19 | gggUGCCUUUUGCCUaggUUgUgaUUUgUaaCCUUCUGCCC3'-3'U | 212 | ++ | − |
| ChD70-m2C | gggUGCCUUUUGCCUaggUUgU------gUaaCCUUCUGCCCa3'-3'U | 213 | ++ | |
| ChD70-m21 | gggUGCCUUUUGCCUaggUUg--------UaaCCUUCUGCCCa3'-3'U | 214 | ++ | |
| ChD70-m22 | gggUGCCUUUUGCCUaggUU----------aaCCUUCUGCCCa3'-3'U | 215 | +++ | |

Lower case-bold residues indicate 2'Omethyl substitutions. The gap shown was occupied by a PEG linker (spacer 18 Glen Research).
Number of (+) indicate extent of binding or inhibition of TGFβ1 bioactivity.

We claim:

1. A purified and isolated non-naturally occurring RNA ligand to transforming growth factor β2 (TGFβ2) wherein said ligand is selected from the group consisting of the sequences set forth in Tables 5, 7, 8, 11, 13, 14, 16–19, and FIG. 9 (SEQ ID NOS: 21–121 and 128–193).

2. The purified and isolated non-naturally occurring RNA ligand of claim 1 comprising SEQ ID NO:115 conjugated to polyethylene glycol (PEG), having the following structure:

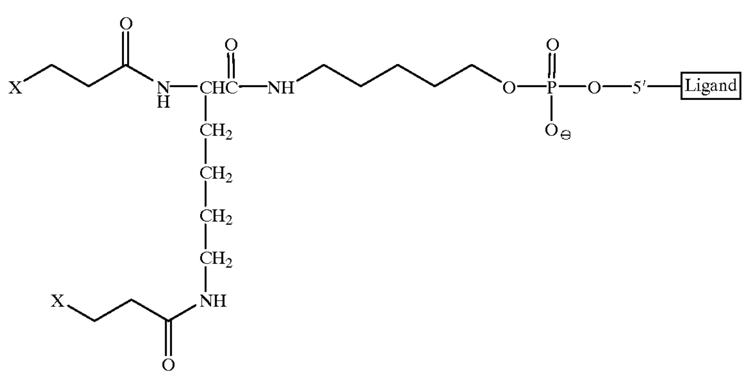

wherein

X=PEG, and

LIGAND=rGrGrArGrGfUfUrAfUfUrAfCrArGrArGf UfCfUrGfU fUrArGfCfUrGfUrAfCfUfCfC-3'-3'-dT.

3. The purified and isolated non-naturally occurring RNA ligand of claim 2 wherein said PEG has a molecular weight of about between 10–80 K.

4. The purified and isolated non-naturally occurring RNA ligand of claim 2 wherein said PEG has a molecular weight of about 20–45 K.

5. The purified and isolated non-naturally occurring RNA ligand of claim 2, wherein said ligand is

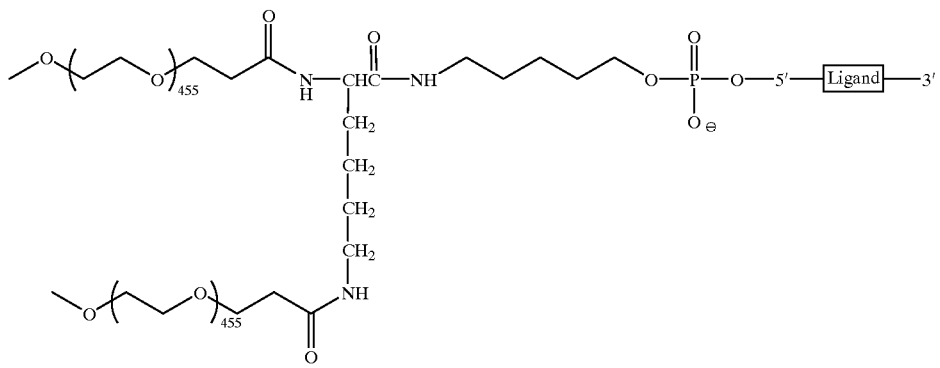
LIGAND = rGrGrArGrGfUfUrAfUfUrAfCrAr GrArGfUfCfUrGfUfUrArGfCfUrGfUrAfCfUfCfC-3'-3'-dT (SEQ ID NO:115), wherein rG is 2'OH G, rA is 2'OH A, fU is 2'F U and fC is 2'F C.
* * * * *

SEQUENCE LISTING

<160> NUMBER OF SEQ ID NOS: 216

<210> SEQ ID NO 1
<211> LENGTH: 71
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: Feature N at positions 17-56 is A, C, G or T.

<400> SEQUENCE: 1
tcgggcgagt cgtctgnnnn nnnnnnnnnn nnnnnnnnnn nnnnnnnnnn nnnnnnccgc    60
atcgtcctcc c                                                         71

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 2
taatacgact cactataggg aggacgatgc gg                                  32

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 3
tcgggcgagt cgtctg                                                    16

<210> SEQ ID NO 4
<211> LENGTH: 88
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(88)
<223> OTHER INFORMATION: Feature N at positions 33-72 is A, C, G or T.

<400> SEQUENCE: 4
taatacgact cactataggg aggacgatgc ggnnnnnnnn nnnnnnnnnn nnnnnnnnnn    60
nnnnnnnnnn nncagacgac tcgcccga                                       88

<210> SEQ ID NO 5
<211> LENGTH: 88
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(88)
<223> OTHER INFORMATION: Feature N at positions 33-72 is A, C, G or T.

<400> SEQUENCE: 5

```
attatgctga gtgatatccc tcctgctacg ccnnnnnnnn nnnnnnnnnn nnnnnnnnnn      60
nnnnnnnnnn nngtctgctg agcgggct                                        88
```

<210> SEQ ID NO 6
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F; feature N at positions
      16-55 is A, 2'-FC, G or 2'-FU.

<400> SEQUENCE: 6

```
gggaggacga ugcggnnnnn nnnnnnnnnn nnnnnnnnnn nnnnnnnnnn nnnnncagac      60
gacucgcccg a                                                          71
```

<210> SEQ ID NO 7
<211> LENGTH: 65
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: Feature N at positions 16-49 is SEQ ID NO: 115
      and A, C, G or T.

<400> SEQUENCE: 7

```
gggaggacga tgcggnnnnn nnnnnnnnnn nnnnnnnnnn nnnnnnnnnc agacgactcg      60
cccga                                                                 65
```

<210> SEQ ID NO 8
<211> LENGTH: 82
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(82)
<223> OTHER INFORMATION: Feature N at positions 33-66 is SEQ ID NO: 115
      and A, C, G or T.

<400> SEQUENCE: 8

```
taatacgact cactataggg aggacgatgc ggnnnnnnnn nnnnnnnnnn nnnnnnnnnn      60
nnnnnncaga cgactcgccc ga                                              82
```

<210> SEQ ID NO 9
<211> LENGTH: 82
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(82)
<223> OTHER INFORMATION: Feature N at positions 33-66 is SEQ ID NO: 115
      and A, C, G or T.

<400> SEQUENCE: 9

```
attatgctga gtgatatccc tcctgctacg ccnnnnnnnn nnnnnnnnnn nnnnnnnnnn      60
```
nnnnnngtct gctgagcggg ct                                               82

<210> SEQ ID NO 10
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F; feature N at positions
      16-49 is SEQ ID NO: 115 and A, 2'-FC, G or 2'-FU.

<400> SEQUENCE: 10
gggaggacga ugcggnnnnn nnnnnnnnnn nnnnnnnnnn nnnnnnnnnc agacgacucg      60
cccga                                                                  65

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 11
cgcaggatcc taatacgact cactata                                          27

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 12
ggcagaattc tcatctactt agtcgggcga gtcgtctg                              38

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 13
agcggataac aatttcacac agg                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 14
gtgctgcaag gcgattaagt tgg                                              23

<210> SEQ ID NO 15
<211> LENGTH: 19
<212> TYPE: DNA
<213> ORGANISM: Artificial Sequence
<220> FEATURE:

```
<223> OTHER INFORMATION: Description of Artificial Sequence:  Synthetic
      Sequence

<400> SEQUENCE: 15
actttatgct tccggctcg                                                  19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 16
gccaaatgcc gagagaacg                                                  19

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 17
ggggacaagc ggacttag                                                   18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 18
gggagtacag ctatacag                                                   18

<210> SEQ ID NO 19
<211> LENGTH: 15
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(15)
<223> OTHER INFORMATION: Bases at positions 5-15 are 2'-OMe.

<400> SEQUENCE: 19
ccgcaugcuc cuccc                                                      15

<210> SEQ ID NO 20
<211> LENGTH: 14
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(12)
<223> OTHER INFORMATION: Bases at positions 1-12 are 2'-OMe.

<400> SEQUENCE: 20
ucgggcgagu cgcg                                                       14
```

```
<210> SEQ ID NO 21
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'F.

<400> SEQUENCE: 21
gggaggacga ugcgguccuc aaugaucuuu ccuguuuaug cuccccagac gacucgcccg     60
a                                                                    61

<210> SEQ ID NO 22
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 22
gggaggacga ugcggaagua acguuuaagu aaaauucguu cucucgguau uuggccagac     60
gacucgcccg a                                                         71

<210> SEQ ID NO 23
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 23
gggaggacga ugcggaagua acguugaagu aaaauucguu cucucggcau uuggccagac     60
gacucgcccg a                                                         71

<210> SEQ ID NO 24
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 24
gggaggacga ugcgguccua accaucacaa ucucaauucu uauauuuucc cgccccagac     60
gacucgcccg a                                                         71

<210> SEQ ID NO 25
<211> LENGTH: 69
<212> TYPE: RNA
<213> ORGANISM: Artificial Sequence
<220> FEATURE:
<223> OTHER INFORMATION: Description of Artificial Sequence: Synthetic
      Sequence
```

```
<221> NAME/KEY: modified_base
<222> LOCATION: (1)..(69)
<223> OTHER INFORMATION: All pyrimidines are 2'F.

<400> SEQUENCE: 25
gggaggacga ugcggaaacc aaaagaccac aucuccauac ucacgcucug ccccagacga    60
cucgcccga                                                           69

<210> SEQ ID NO 26
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 26
gggaggacga ugcggauaga ucgguccgau aagucuuuca ucuuuaccug gccccagac    60 gacucgcccg a                                                        71

<210> SEQ ID NO 27
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 27
gggaggacga ugcggaagua acguugaagu aaaauucguu cucucgguau uuggccagac    60
gacucgcccg a                                                        71

<210> SEQ ID NO 28
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 28
gggaggacga ugcggacgau ccuuccuua acauuucauc auuucuccug ugccccagac    60
gacucgcccg g                                                        71

<210> SEQ ID NO 29
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 29
gggaggacga ugcgguccau caacaaucuu aucauuaugu uuuccuucc cgcccagac     60
```
gacucgcccg a      71

<210> SEQ ID NO 30
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 30
gggaggacga ugcgguccuc ugagccgauc uucuucacua cuucuuuuuc ugccccagac      60
gacucgcccg a      71

<210> SEQ ID NO 31
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 31
gggaggacga ugcgguuccu caauucuucc aucuucauaa uguuucccuu ugccccagac      60
gacucgcccg a      71

<210> SEQ ID NO 32
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 32
gggaggacga ugcggucuac ccuuuagcag uauuuguuuc caucguuguu ugccccagac      60
gacucgcccg g      71

<210> SEQ ID NO 33
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 33
gggaggacga ugcggucuca acgaagaaca ucguuggaua cuguuugucc cgccccagac      60
gacucgcccg a      71

<210> SEQ ID NO 34
<211> LENGTH: 71
<212> TYPE: RNA

<210> SEQ ID NO 34
<211> LENGTH: 71
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(71)
<223> OTHER INFORMATION: All pyrimidines are 2'F.

<400> SEQUENCE: 34
gggaggacga ugcgguucag uuccuucag uuucguuuc uaauucuugu gucccagac    60 gacucgcccg a    71

<210> SEQ ID NO 35
<211> LENGTH: 61
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(61)
<223> OTHER INFORMATION: All pyrimidines are 2'F.

<400> SEQUENCE: 35
gggaggacga ugcggagcgg auuaauuagu cugacuucuu gucccagac gacucgcccg    60 a    61

<210> SEQ ID NO 36
<211> LENGTH: 71
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(71)
<223> OTHER INFORMATION: All pyrimidines are 2'F.

<400> SEQUENCE: 36
gggaggacga ugcggagaca ucuuugucuc gauuagucau guuccuuacc ugcccagac    60 gacucgcccg a    71

<210> SEQ ID NO 37
<211> LENGTH: 69
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(69)
<223> OTHER INFORMATION: All pyrimidines are 2'F.

<400> SEQUENCE: 37
gggaggacga ugcgguccuc uagcaagcag cuucucaucu uauuuuccg ccccagacga    60 cucgcccga    69

<210> SEQ ID NO 38
<211> LENGTH: 71
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(71)
<223> OTHER INFORMATION: All pyrimidines are 2'F.

<400> SEQUENCE: 38
gggaggacga ugcggugcac agugauggau gacauuguau aacgguaugc gucccagac    60 gacucgcccg a    71

<210> SEQ ID NO 39
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 39
gggaggacga ugcggaccua ucuuucuucc aagucauagu uuuacuuccc gccccagacg    60
acucgcccga    70

<210> SEQ ID NO 40
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 40
gggaggacga ugcggaugag accuaaucau cgauccgcua ucuaaaaccu caccccagac    60
gacucgcccg a    71

<210> SEQ ID NO 41
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 41
gggaggacga ugcgguccuc agacaaaucu uucuugaauc uuuccuuaac ugccccagac    60
gacucgcccg a    71

<210> SEQ ID NO 42
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 42
gggaggacga ugcggaccga uucuccaacu ugacauuuau uccucuuucu gccccagacg    60
acucgcccga    70

<210> SEQ ID NO 43
<211> LENGTH: 71
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(71)
<223> OTHER INFORMATION: All pyrimidines are 2'F.

<400> SEQUENCE: 43
gggaggacga ugcgguccuc ugagccaauc uucuucgcua cuucuuuuuc ugccccagac    60
gacucgcccg a                                                        71

<210> SEQ ID NO 44
<211> LENGTH: 71
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(71)
<223> OTHER INFORMATION: All pyrimidines are 2'F.

<400> SEQUENCE: 44
gggaggacga ugcggauucu uucuccaacg cuuuucacua ccuacauuuc ugccccagac    60
gacucgcccg a                                                        71

<210> SEQ ID NO 45
<211> LENGTH: 71
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(71)
<223> OTHER INFORMATION: All pyrimidines are 2'F.

<400> SEQUENCE: 45
gggaggacga ugcggauccu auccucugaa uaucauuaaa ucaucuucuc cgccccagac    60
gacucgcccg a                                                        71

<210> SEQ ID NO 46
<211> LENGTH: 70
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(70)
<223> OTHER INFORMATION: All pyrimidines are 2'F.

<400> SEQUENCE: 46
gggaggacga ugcgguucaa ucaucuucac ucucauuucc uuuuuccuac uccccagacg    60
acucgcccga                                                          70

<210> SEQ ID NO 47
<211> LENGTH: 71
<212> TYPE: RNA
<213> ORGANISM: Artificial Sequence
<220> FEATURE:
<223> OTHER INFORMATION: Description of Artificial Sequence: Synthetic

```
                              Sequence
<221> NAME/KEY: modified_base
<222> LOCATION: (1)..(71)
<223> OTHER INFORMATION: All pyrimidines are 2'F.

<400> SEQUENCE: 47
gggaggacga ugcggcgaua gaaucuaguc guucuagaug aucugguacg ugccccagac    60
gacucgcccg a                                                        71

<210> SEQ ID NO 48
<211> LENGTH: 71
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(71)
<223> OTHER INFORMATION: All pyrimidines are 2'F.

<400> SEQUENCE: 48
gggaggacga ugcgguagua auccuugucu uccauuucuc uuuacccuuu ugccccagac    60
gacucgcccg a                                                        71

<210> SEQ ID NO 49
<211> LENGTH: 61
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(61)
<223> OTHER INFORMATION: All pyrimidines are 2'F.

<400> SEQUENCE: 49
gggaggacga ugcggcccau uaguccucau uagucccug ugccccagac gacucgcccg     60
a                                                                   61

<210> SEQ ID NO 50
<211> LENGTH: 71
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(71)
<223> OTHER INFORMATION: All pyrimidines are 2'F.

<400> SEQUENCE: 50
gggaggacga ugcggcaucu uauccuccau caguuacucu ucguuauucc cgccccagac    60
gacucgcccg a                                                        71

<210> SEQ ID NO 51
<211> LENGTH: 70
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(70)
<223> OTHER INFORMATION: All pyrimidines are 2'F.

<400> SEQUENCE: 51
```

```
gggaggacga ugcgguccaa auccucuucc cauguuagca uucagccuug uccccagacg    60
acucgcccga                                                          70
```

<210> SEQ ID NO 52
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 52

```
gggaggacga ugcgguuccg acaauuuccu ccaccauuag auuucuugcu gccccagacg    60
acucgcccga                                                          70
```

<210> SEQ ID NO 53
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 53

```
gggaggacga ugcggucuug auccuccuuu gugucuuucu uugucuuccc ugccccagac    60
gacucgcccg a                                                        71
```

<210> SEQ ID NO 54
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 54

```
gggaggacga ugcggaagua acguugaagu aaaauucguu cucucgguau uggccagacg    60
acucgcccga                                                          70
```

<210> SEQ ID NO 55
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 55

```
gggaggacga ugcgguccga ucaguuccuu cgauuaaucu ucuuccugc cccccagacg     60 acucgcccga                                                          70
```

<210> SEQ ID NO 56
<211> LENGTH: 71

```
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 56
gggaggacga ugcggaaucc uucucccuga ugaauaugac cuuuucuug cuccccagac    60 gacucgcccg a                                                       71

<210> SEQ ID NO 57
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 57
gggaggacga ugcggaugau cuuuaauguc ugguuugagg ucaaugcggg ugccccagac    60
gacucgcccg a                                                       71

<210> SEQ ID NO 58
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 58
gggaggacga ugcggagaug guacuccauc uccuuuaugu gcccaucgcu guccccagac    60
gacucgcccg a                                                       71

<210> SEQ ID NO 59
<211> LENGTH: 61
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(61)
<223> OTHER INFORMATION: All pyrimidines are 2'F.

<400> SEQUENCE: 59
gggaggacga ugcgguccuc gauucuaauu uacuccuuuu uccccagac gacucgcccg    60 a                                                                  61

<210> SEQ ID NO 60
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
```

<223> OTHER INFORMATION: All pyrimidines are 2'F.

<400> SEQUENCE: 60
gggaggacga ugcggucuac ccuuuagcag uauuuguuuc caucguuguu ugccccagac    60
gacucgcccg a                                                         71

<210> SEQ ID NO 61
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 61
gggaggacga ugcggcacaa uauucccuc uacuuccacg uauuuccug uccccagacg    60 acucgcccga                                                          70

<210> SEQ ID NO 62
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 62
gggaggacga ugcgguccuc aaccuuagac uuucauuucu ucaguucuuc ugccccagac    60
gacucgcccg a                                                         71

<210> SEQ ID NO 63
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 63
gggaggacga ugcgguagug gucugucaaa ggaauagcua guaguguuug guccccagac    60
gacucgcccg a                                                         71

<210> SEQ ID NO 64
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 64
gggaggacga ugcggcaucu uccuuagcau accaguuuau uccuuucccu guccccagac    60
gacucgcccg a                                                         71

<210> SEQ ID NO 65
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 65
gggaggacga ugcggagcga caguauaguu aguacucuag cucuagugcu gucccagac    60 gacucgcccg a                                                       71

<210> SEQ ID NO 66
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 66
gggaggacga ugcggaccuc ucaugaucag caucucgcgu aaucacgguu caccccagac    60
gacucgcccg a                                                         71

<210> SEQ ID NO 67
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 67
gggaggacga ugcgguccgu acuccauuuc cuauuugauu ccuuuccuc ugccccagac    60 gacucgcccg a                                                       71

<210> SEQ ID NO 68
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 68
gggaggacga ugcggaaccc acgaccuuac cuuaaucaug uauuucucuc ugccccagac    60
gacucgcccg a                                                        71

<210> SEQ ID NO 69
<211> LENGTH: 65
<212> TYPE: RNA
<213> ORGANISM: Artificial Sequence
<220> FEATURE:

```
<223> OTHER INFORMATION: Description of Artificial Sequence:  Synthetic
      Sequence
<221> NAME/KEY: modified_base
<222> LOCATION: (1)..(65)
<223> OTHER INFORMATION: All pyrimidines are 2'F.

<400> SEQUENCE: 69
gggaggacga ugcggagaua augagugacg gugauuauag augcugcccc agacgacucg     60
cccga                                                                65

<210> SEQ ID NO 70
<211> LENGTH: 71
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(71)
<223> OTHER INFORMATION: All pyrimidines are 2'F.

<400> SEQUENCE: 70
gggaggacga ugcgguuccu caauucuucc aucuucauaa uguuucccuu ugcccagac      60 gacucgcccg a                                                         71

<210> SEQ ID NO 71
<211> LENGTH: 60
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(60)
<223> OTHER INFORMATION: All pyrimidines are 2'F.

<400> SEQUENCE: 71
gggaggacga ugcgguuccu uccaacguua ucuacuuucu gccccagacg acucgcccga     60

<210> SEQ ID NO 72
<211> LENGTH: 71
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(71)
<223> OTHER INFORMATION: All pyrimidines are 2'F.

<400> SEQUENCE: 72
gggaggacga ugcggaagua acguuguagu aaaauucguu cucucggcau uuggccagac     60
gacucgcccg a                                                         71

<210> SEQ ID NO 73
<211> LENGTH: 70
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(70)
<223> OTHER INFORMATION: All pyrimidines are 2'F.

<400> SEQUENCE: 73
gggaggacga ugcggaagua acguuauagu aaaauucguu cucucgguau uggccagacg     60
```
acucgcccga                                                              70

<210> SEQ ID NO 74
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 74
gggaggacgg ugcggaagua acguuguagu aaaauucguu cucucggcgu uuggccagac        60
gacucgcccg a                                                            71

<210> SEQ ID NO 75
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 75
gggaggacga ugcggaagua acguuguagu aaaauucguu cucucggcgu uuggucagac        60
gacucgcccg a                                                            71

<210> SEQ ID NO 76
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 76
gggagacgau gcggaaguaa cguuguagua aaauucguuc ucucggcauu uggccagacg        60
acucgcccga                                                              70

<210> SEQ ID NO 77
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 77
gggaggacga ugcggaagua acguugaagu aaaauucguu cucucugcgu uuggucagac        60
gacucgcccg a                                                            71

<210> SEQ ID NO 78
<211> LENGTH: 70
<212> TYPE: RNA

```
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 78
gggaggacga ugcggaagua acguugaagu aaaauucguu cuccugguau uggccagacg    60
acucgcccga                                                          70

<210> SEQ ID NO 79
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 79
gggaggacga ugcggaagua acguugaagu aaaauucguu cucuggcau uuggccagac     60 gacucgcccg a                                                        71

<210> SEQ ID NO 80
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 80
gggaggacga ugcggaagua acguuguagu aaaauucguu cucuuggcau uugccagacg    60
acucgcccga                                                          70

<210> SEQ ID NO 81
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 81
gggaggacga ugcggaagua acguuaaagu aaaauucguu cucuggcgu uuggccagac     60 gacucgcccg a                                                        71

<210> SEQ ID NO 82
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.
```

<400> SEQUENCE: 82
gggaggacga ugcggaagua acguugaagu aaaauucguu cucucggcgu uuggccagac    60
gacucgcccg a    71

<210> SEQ ID NO 83
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 83
gggaggacga ugcggaagua acguuguagu aaaauucguu cucucgguau uuggccagac    60
gacucgcccg a    71

<210> SEQ ID NO 84
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 84
gggaggacga ugcggaagua acguuguagu aaaauucguu cucuuggucu uggccagacg    60
acucgcccga    70

<210> SEQ ID NO 85
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 85
ggaggacgau gcgaaguaac guuguaguaa aauucguucu cucgggcauu uggcagacga    60
cuucgcccga    70

<210> SEQ ID NO 86
<211> LENGTH: 71
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(71)
<223> OTHER INFORMATION: All pyrimidines are 2'F.

<400> SEQUENCE: 86
gggaggacga ugcggcguug uuuagucgua uguauauacu aaguccgcuu gucccagac    60 gacucgcccg a    71

<210> SEQ ID NO 87
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 87
gggaggacga ugcgguucag gagguuauua cagagucugu auagcuguac uccccagacg   60
acucgcccga                                                         70

<210> SEQ ID NO 88
<211> LENGTH: 70
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(70)
<223> OTHER INFORMATION: All pyrimidines are 2'F.

<400> SEQUENCE: 88
gggaggacga ugcgguucag gaggguauua cagagucugu auagcuguac uccccagacg   60
acucgcccga                                                         70

<210> SEQ ID NO 89
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'F.

<400> SEQUENCE: 89
gguucaggag guuauuacag agucuguaua gcuguaccuc ccagacgacu cgcccga      57

<210> SEQ ID NO 90
<211> LENGTH: 56
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(56)
<223> OTHER INFORMATION: All pyrimidines are 2'F.

<400> SEQUENCE: 90
gggaggacga ugcgguucag gagguuauua cagagucugu auagcuguac ucccca       56

<210> SEQ ID NO 91
<211> LENGTH: 43
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(43)
<223> OTHER INFORMATION: All pyrimidines are 2'F.

<400> SEQUENCE: 91
gguucaggag guuauuacag agucuguaua gcuguacucc cca        43

<210> SEQ ID NO 92
<211> LENGTH: 36
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(36)
<223> OTHER INFORMATION: All pyrimidines are 2'F.

<400> SEQUENCE: 92
ggagguuauu acagagucug uauagcugua cuccc        36

<210> SEQ ID NO 93
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F.

<400> SEQUENCE: 93
ggagguuauu acagagucug uauagcugua cucc        34

<210> SEQ ID NO 94
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(30)
<223> OTHER INFORMATION: All pyrimidines are 2'F.

<400> SEQUENCE: 94
ggagguuauu acagagucug uauagcugua        30

<210> SEQ ID NO 95
<211> LENGTH: 26
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(26)
<223> OTHER INFORMATION: All pyrimidines are 2'F.

<400> SEQUENCE: 95
ggagguuauu acagagucug uauagc        26

<210> SEQ ID NO 96
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(30)

<223> OTHER INFORMATION: All pyrimidines are 2'F.

<400> SEQUENCE: 96
ggagguuauu acagagucug uauagccucc                              30

<210> SEQ ID NO 97
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(30)
<223> OTHER INFORMATION: All pyrimidines are 2'F.

<400> SEQUENCE: 97
ggagguuauu agagucuaua gcuguacucc                              30

<210> SEQ ID NO 98
<211> LENGTH: 26
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(26)
<223> OTHER INFORMATION: All pyrimidines are 2'F.

<400> SEQUENCE: 98
ggagguuauu agagucuaua gccucc                                  26

<210> SEQ ID NO 99
<211> LENGTH: 33
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(33)
<223> OTHER INFORMATION: All pyrimidines are 2'F.

<400> SEQUENCE: 99
ggagguuauu acagagucug uauagcugua cuc                          33

<210> SEQ ID NO 100
<211> LENGTH: 32
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(32)
<223> OTHER INFORMATION: All pyrimidines are 2'F.

<400> SEQUENCE: 100
ggagguuauu acagagucug uauagcugua cu                           32

<210> SEQ ID NO 101
<211> LENGTH: 31
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(31)
<223> OTHER INFORMATION: All pyrimidines are 2'F.

<400> SEQUENCE: 101
ggagguuauu acagagucug uauagcugua c                               31

<210> SEQ ID NO 102
<211> LENGTH: 33
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(33)
<223> OTHER INFORMATION: All pyrimidines are 2'F.

<400> SEQUENCE: 102
ggagguuauu acagagucug uauagcguac ucc                             33

<210> SEQ ID NO 103
<211> LENGTH: 33
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(33)
<223> OTHER INFORMATION: All pyrimidines are 2'F.

<400> SEQUENCE: 103
ggagguuauu acagagucug uauagcuguc ucc                             33

<210> SEQ ID NO 104
<211> LENGTH: 32
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(32)
<223> OTHER INFORMATION: All pyrimidines are 2'F.

<400> SEQUENCE: 104
ggagguuauu acagagucug uauagcuacu cc                              32

<210> SEQ ID NO 105
<211> LENGTH: 33
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(33)
<223> OTHER INFORMATION: All pyrimidines are 2'F.

<400> SEQUENCE: 105
ggagguuaua cagagucugu auagcuguac ucc                             33

<210> SEQ ID NO 106
<211> LENGTH: 33
<212> TYPE: RNA
<213> ORGANISM: Artificial Sequence
<220> FEATURE:
<223> OTHER INFORMATION: Description of Artificial Sequence: Synthetic
      Sequence

```
<221> NAME/KEY: modified_base
<222> LOCATION: (1)..(33)
<223> OTHER INFORMATION: All pyrimidines are 2'F.

<400> SEQUENCE: 106
ggagguuauu acagaucugu auagcuguac ucc                              33

<210> SEQ ID NO 107
<211> LENGTH: 32
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(32)
<223> OTHER INFORMATION: All pyrimidines are 2'F.

<400> SEQUENCE: 107
ggagguuauu acaaguugua uagcuguacu cc                               32

<210> SEQ ID NO 108
<211> LENGTH: 33
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(33)
<223> OTHER INFORMATION: All pyrimidines are 2'F.

<400> SEQUENCE: 108
ggagguuauu acagaguugu auagcuguac ucc                              33

<210> SEQ ID NO 109
<211> LENGTH: 32
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(32)
<223> OTHER INFORMATION: All pyrimidines are 2'F.

<400> SEQUENCE: 109 ggggguuauua cagagucugu auagcuguac cc                              32

<210> SEQ ID NO 110
<211> LENGTH: 32
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(32)
<223> OTHER INFORMATION: All pyrimidines are 2'F.

<400> SEQUENCE: 110
ggagguuauu acgagucugu auagcguacu cc                               32

<210> SEQ ID NO 111
<211> LENGTH: 33
<212> TYPE: RNA
<213> ORGANISM: Artificial Sequence
<220> FEATURE:
<223> OTHER INFORMATION: Description of Artificial Sequence:  Synthetic
```

```
      Sequence
<221> NAME/KEY: modified_base
<222> LOCATION: (1)..(33)
<223> OTHER INFORMATION: All pyrimidines are 2'F.

<400> SEQUENCE: 111
ggagauauua cagagucugu auagcuguac ucc                              33

<210> SEQ ID NO 112
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(30)
<223> OTHER INFORMATION: All pyrimidines are 2'F.

<400> SEQUENCE: 112
gggguuauuc agagucugua uagcugaccc                                  30

<210> SEQ ID NO 113
<211> LENGTH: 30
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(30)
<223> OTHER INFORMATION: All pyrimidines are 2'F.

<400> SEQUENCE: 113
gggguuauua agagucugua uagcuuaccc                                  30

<210> SEQ ID NO 114
<211> LENGTH: 36
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(36)
<223> OTHER INFORMATION: All pyrimidines are 2'F.

<400> SEQUENCE: 114
ggagguuauu acagagucug uauagcugua cuccccc                          36

<210> SEQ ID NO 115
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F.

<400> SEQUENCE: 115
ggagguuauu acagagucug uauagcugua cucc                             34

<210> SEQ ID NO 116
<211> LENGTH: 37
<212> TYPE: RNA
<213> ORGANISM: Artificial Sequence
<220> FEATURE:
```

```
<223> OTHER INFORMATION: Description of Artificial Sequence:  Synthetic
      Sequence
<221> NAME/KEY: modified_base
<222> LOCATION: (1)..(37)
<223> OTHER INFORMATION: All pyrimidines are 2'F.

<400> SEQUENCE: 116
ggagguuauu acagagucug uauagcugua cucccca                               37

<210> SEQ ID NO 117
<211> LENGTH: 30
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(30)
<223> OTHER INFORMATION: All pyrimidines are 2'F.

<400> SEQUENCE: 117
ggagguuauu acagagucug uauagcugua                                      30

<210> SEQ ID NO 118
<211> LENGTH: 33
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(33)
<223> OTHER INFORMATION: All pyrimidines are 2'F.

<400> SEQUENCE: 118
gagguuauua cagagucugu auagcuguac ucc                                  33

<210> SEQ ID NO 119
<211> LENGTH: 32
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(32)
<223> OTHER INFORMATION: All pyrimidines are 2'F.

<400> SEQUENCE: 119
agguuauuac agagucugua uagcuguacu cc                                   32

<210> SEQ ID NO 120
<211> LENGTH: 31
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(31)
<223> OTHER INFORMATION: All pyrimidines are 2'F.

<400> SEQUENCE: 120
gguuauuaca gagucuguau agcuguacuc c                                    31

<210> SEQ ID NO 121
<211> LENGTH: 34
<212> TYPE: RNA
<213> ORGANISM: Artificial Sequence
```

-continued

```
<220> FEATURE:
<223> OTHER INFORMATION: Description of Artificial Sequence:  Synthetic
      Sequence
<221> NAME/KEY: modified_base
<222> LOCATION: (1)..(34)
<223> OTHER INFORMATION: All pyrimidines are 2'F.

<400> SEQUENCE: 121
ggagguuauu acagagucug uauagcugua cucc                             34

<210> SEQ ID NO 122
<211> LENGTH: 60
<212> TYPE: PRT
<213> ORGANISM: Artificial Sequence
<220> FEATURE:
<223> OTHER INFORMATION: Description of Artificial Sequence:  Synthetic
      Sequence

<400> SEQUENCE: 122

Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys
    50                  55                  60

<210> SEQ ID NO 123
<211> LENGTH: 60
<212> TYPE: PRT
<213> ORGANISM: Artificial Sequence
<220> FEATURE:
<223> OTHER INFORMATION: Description of Artificial Sequence:  Synthetic
      Sequence

<400> SEQUENCE: 123

Ala Leu Asp Ala Ala Tyr Cys Phe Arg Asn Val Gln Asp Asn Cys Cys
 1               5                  10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg
    50                  55                  60

<210> SEQ ID NO 124
<211> LENGTH: 60
<212> TYPE: PRT
<213> ORGANISM: Artificial Sequence
<220> FEATURE:
<223> OTHER INFORMATION: Description of Artificial Sequence:  Synthetic
      Sequence

<400> SEQUENCE: 124

Ala Leu Asp Thr Asn Tyr Cys Phe Arg Asn Leu Glu Glu Asn Cys Cys
 1               5                  10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr
    50                  55                  60
```

<210> SEQ ID NO 125
<211> LENGTH: 52
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 125

Val Leu Ala Leu Tyr Asn Gln His Asn Pro Gly Ala Ser Ala Ala Pro
 1               5                  10                  15

Cys Cys Val Pro Gln Ala Leu Glu Pro Leu Pro Ile Val Tyr Tyr Val
            20                  25                  30

Gly Arg Lys Pro Lys Val Glu Gln Leu Ser Asn Met Ile Val Arg Ser
        35                  40                  45

Cys Lys Cys Ser
    50

<210> SEQ ID NO 126
<211> LENGTH: 52
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 126

Val Leu Ser Leu Tyr Asn Thr Ile Asn Pro Glu Ala Ser Ala Ser Pro
 1               5                  10                  15

Cys Cys Val Ser Gln Asp Leu Glu Pro Leu Thr Ile Leu Tyr Tyr Ile
            20                  25                  30

Gly Lys Thr Pro Lys Ile Glu Gln Leu Ser Asn Met Ile Val Lys Ser
        35                  40                  45

Cys Lys Cys Ser
    50

<210> SEQ ID NO 127
<211> LENGTH: 52
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 127

Val Leu Gly Leu Tyr Asn Thr Leu Asn Pro Glu Ala Ser Ala Ser Pro
 1               5                  10                  15

Cys Cys Val Pro Gln Asp Leu Pro Leu Thr Ile Leu Tyr Tyr Val
            20                  25                  30

Gly Arg Thr Pro Lys Val Glu Gln Leu Ser Asn Met Val Val Lys Ser
        35                  40                  45

Cys Lys Cys Ser
    50

<210> SEQ ID NO 128
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base

```
<222> LOCATION: (1)..(58)
<223> OTHER INFORMATION: All pyrimidines are 2'F.

<400> SEQUENCE: 128
ggaaguaacg uuguaguaaa auucguucuc ucggcauuug gccagacgac ucgcccga        58

<210> SEQ ID NO 129
<211> LENGTH: 57
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(57)
<223> OTHER INFORMATION: All pyrimidines are 2'F.

<400> SEQUENCE: 129
gggaggacga ugcggaagua acguuguagu aaaauucguu cucucggcau uggcca           57

<210> SEQ ID NO 130
<211> LENGTH: 44
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(44)
<223> OTHER INFORMATION: All pyrimidines are 2'F.

<400> SEQUENCE: 130
ggaaguaacg uuguaguaaa auucguucuc ucggcauuug gcca                        44

<210> SEQ ID NO 131
<211> LENGTH: 38
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(38)
<223> OTHER INFORMATION: All pyrimidines are 2'F.

<400> SEQUENCE: 131
gggaggaugc ggaaguaacg uuguaguaaa auccuuc                                38

<210> SEQ ID NO 132
<211> LENGTH: 35
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(35)
<223> OTHER INFORMATION: All pyrimidines are 2'F.

<400> SEQUENCE: 132
gggaggaugc ggaaguaacg uuguaguaaa auucc                                  35

<210> SEQ ID NO 133
<211> LENGTH: 32
<212> TYPE: RNA
<213> ORGANISM: Artificial Sequence
<220> FEATURE:
<223> OTHER INFORMATION: Description of Artificial Sequence: Synthetic
      Sequence
```

```
<221> NAME/KEY: modified_base
<222> LOCATION: (1)..(32)
<223> OTHER INFORMATION: All pyrimidines are 2'F.

<400> SEQUENCE: 133
gggaggaugc ggaaguaacg uuguaguaaa au                              32

<210> SEQ ID NO 134
<211> LENGTH: 33
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(33)
<223> OTHER INFORMATION: All pyrimidines are 2'F.

<400> SEQUENCE: 134
gggaggaugc ggaaguaacg uuguaguucc uuc                             33

<210> SEQ ID NO 135
<211> LENGTH: 27
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(27)
<223> OTHER INFORMATION: All pyrimidines are 2'F.

<400> SEQUENCE: 135
gggaggaugc ggaaguaacg uuguagu                                    27

<210> SEQ ID NO 136
<211> LENGTH: 20
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(20)
<223> OTHER INFORMATION: All pyrimidines are 2'F.

<400> SEQUENCE: 136
gggaggagua acguuguagu                                            20

<210> SEQ ID NO 137
<211> LENGTH: 58
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(58)
<223> OTHER INFORMATION: All pyrimidines are 2'F.

<400> SEQUENCE: 137
ggcguuguuu agucguaugu auauacuaag uccgcuuguc cccagacgac ucgcccga   58

<210> SEQ ID NO 138
<211> LENGTH: 57
<212> TYPE: RNA
<213> ORGANISM: Artificial Sequence
<220> FEATURE:
<223> OTHER INFORMATION: Description of Artificial Sequence: Synthetic
```

```
                Sequence
<221> NAME/KEY: modified_base
<222> LOCATION: (1)..(57)
<223> OTHER INFORMATION: All pyrimidines are 2'F.

<400> SEQUENCE: 138
gggaggacga ugcggcguug uuuagucgua uguauauacu aaguccgcuu gucccca        57

<210> SEQ ID NO 139
<211> LENGTH: 44
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(44)
<223> OTHER INFORMATION: All pyrimidines are 2'F.

<400> SEQUENCE: 139
ggcguuguuu agucguaugu auauacuaag uccgcuuguc ccca                      44

<210> SEQ ID NO 140
<211> LENGTH: 44
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(44)
<223> OTHER INFORMATION: All pyrimidines are 2'F.

<400> SEQUENCE: 140
ggggagcggc guuguuuagu cguauguaua uacuaagucc gcuu                      44

<210> SEQ ID NO 141
<211> LENGTH: 29
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(29)
<223> OTHER INFORMATION: All pyrimidines are 2'F.

<400> SEQUENCE: 141
ggggagcggc guuguugaaa aguccgcuu                                       29

<210> SEQ ID NO 142
<211> LENGTH: 38
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(38)
<223> OTHER INFORMATION: All pyrimidines are 2'F.

<400> SEQUENCE: 142
ggggagcggc guuguuucgu auguauauaa guccgcuu                             38

<210> SEQ ID NO 143
<211> LENGTH: 33
<212> TYPE: RNA
<213> ORGANISM: Artificial Sequence
<220> FEATURE:
```

```
<223> OTHER INFORMATION: Description of Artificial Sequence:  Synthetic
      Sequence
<221> NAME/KEY: modified_base
<222> LOCATION: (1)..(33)
<223> OTHER INFORMATION: All pyrimidines are 2'F.

<400> SEQUENCE: 143
ggggagcggc guuguuuaug uauaaguccg cuu                                    33

<210> SEQ ID NO 144
<211> LENGTH: 42
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(42)
<223> OTHER INFORMATION: All pyrimidines are 2'F.

<400> SEQUENCE: 144
ggggagcggc guuguuuagu cguauguaua uacuaagucc gc                          42

<210> SEQ ID NO 145
<211> LENGTH: 38
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(38)
<223> OTHER INFORMATION: All pyrimidines are 2'F.

<400> SEQUENCE: 145
ggggagcggc guuguuuagu cguauguaua uacuaagu                               38

<210> SEQ ID NO 146
<211> LENGTH: 65
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(65)
<223> OTHER INFORMATION: All pyrimidines are 2'F.

<400> SEQUENCE: 146
gggaggacga ugcgggguga uuauuacaga guauguauag cuguaccccc agacgacucg       60
cccga                                                                   65

<210> SEQ ID NO 147
<211> LENGTH: 64
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(64)
<223> OTHER INFORMATION: All pyrimidines are 2'F.

<400> SEQUENCE: 147
gggaggacga ugcggaggcg uuauuagaga gucuguauag cucuagcccc agacgacucg       60
ccga                                                                    64
```

<210> SEQ ID NO 148
<211> LENGTH: 65
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(65)
<223> OTHER INFORMATION: All pyrimidines are 2'F.

<400> SEQUENCE: 148
gggaggacga ugcggggagg guauuacaga guauguauag cguacuccc agacgacucg    60 cccga    65

<210> SEQ ID NO 149
<211> LENGTH: 65
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(65)
<223> OTHER INFORMATION: All pyrimidines are 2'F.

<400> SEQUENCE: 149
gggaggacga ugcggggagg uuauuauaga gucuguauag cuauaccccc agacgacucg    60
cccga    65

<210> SEQ ID NO 150
<211> LENGTH: 65
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(65)
<223> OTHER INFORMATION: All pyrimidines are 2'F.

<400> SEQUENCE: 150
gggaggacga ugcgggaggg uuauuauaga gucugcauag cuauaccccc agacgacucg    60
cccga    65

<210> SEQ ID NO 151
<211> LENGTH: 65
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(65)
<223> OTHER INFORMATION: All pyrimidines are 2'F.

<400> SEQUENCE: 151
gggaggacga ugcggugaga guauuacgga guauguauag ccguaccccc agacgacucg    60
cccga    65

<210> SEQ ID NO 152
<211> LENGTH: 65
<212> TYPE: RNA
<213> ORGANISM: Artificial Sequence
<220> FEATURE:
<223> OTHER INFORMATION: Description of Artificial Sequence: Synthetic Sequence

```
<221> NAME/KEY: modified_base
<222> LOCATION: (1)..(65)
<223> OTHER INFORMATION: All pyrimidines are 2'F.

<400> SEQUENCE: 152
gggaggacga ugcgggggca uuauuucaga gucuguauag cuguagcccc agacgacucg    60
cccga                                                               65

<210> SEQ ID NO 153
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 153
gggaggacga ugcgggcgga uuaucacaga guauguauag cugugccgcc agacgacucg    60
cccga                                                               65

<210> SEQ ID NO 154
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 154
gggaggacga ugcggguguga auauuagaga gucuguauag cucuacccccc agacgacucg   60 cccga                                                               65

<210> SEQ ID NO 155
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 155
gggaggacga ugcggcggga uuauuacuga gucuguauag caguacccccc agacgacucg   60 cccga                                                               65

<210> SEQ ID NO 156
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 156
gggaggacga ugcggguggaa auauuacgga gucuguauag ccguacuccc agacgacucg   60
```

```
                                                            cccga                     65

<210> SEQ ID NO 157
<211> LENGTH: 65
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(65)
<223> OTHER INFORMATION: All pyrimidines are 2'F.

<400> SEQUENCE: 157
gggaggacga ugcgggggga cuauuaguga gucuguauag cacuaccccc agacgacucg    60
cccga                                                                65

<210> SEQ ID NO 158
<211> LENGTH: 65
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(65)
<223> OTHER INFORMATION: All pyrimidines are 2'F.

<400> SEQUENCE: 158
gggaggacga ugcgggugga uuauuacagc gucuguauau cuguaccccc agacgacucg    60
cccga                                                                65

<210> SEQ ID NO 159
<211> LENGTH: 65
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(65)
<223> OTHER INFORMATION: All pyrimidines are 2'F.

<400> SEQUENCE: 159
gggaggacga ugcgggcagg uuauuacaga gucuguauag cuguacugcc agacgacucg    60
cccga                                                                65

<210> SEQ ID NO 160
<211> LENGTH: 65
<212> TYPE: RNA
<213> ORGANISM: Artificial Sequence
<220> FEATURE:
<223> OTHER INFORMATION: Description of Artificial Sequence:  Synthetic
      Sequence
<221> NAME/KEY: modified_base
<222> LOCATION: (1)..(65)
<223> OTHER INFORMATION: All pyrimidines are 2'F.

<400> SEQUENCE: 160
gggaggacga ugcgggguag auaucacuga gucuguauag cagugccccc agacgacucg    60
cccga                                                                65

<210> SEQ ID NO 161
<211> LENGTH: 65
<212> TYPE: RNA
```

```
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 161
gggaggacga ugcggaggga uuauuacaga gucuguauag cuguaccccc agacgacucg      60
cccga                                                                 65

<210> SEQ ID NO 162
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 162
gggaggacga ugcgggugga uuauuacaga gucuguauag cuguaccccc agacgacucg      60
cccga                                                                 65

<210> SEQ ID NO 163
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 163
gggaggacga ugcgggggcg uuauuacaga gucuguauag cuguagcccc agacgacucg      60
cccga                                                                 65

<210> SEQ ID NO 164
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 164
gggaggacga ugcgggugg uuauuacaca guauguauag guguaccccc agacgacucg       60
cccga                                                                 65

<210> SEQ ID NO 165
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.
```

<400> SEQUENCE: 165
gggaggacga ugcggaggga auauuacaga guauguauag cuguaccccc agacgacucg    60
cccga    65

<210> SEQ ID NO 166
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 166
gggaggacga ugcggggagu uuauuacagc gucuguauau cuguagcccc agacgacucg    60
cccga    65

<210> SEQ ID NO 167
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 167
gggaggacga ugcggugagg uuauuacaga gucuguauag cuguacuccc agacgacucg    60
cccga    65

<210> SEQ ID NO 168
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 168
gggaggacga ugcgggugg uuauuagaga gucuguauag cucuacgccc agacgacucg    60
cccga    65

<210> SEQ ID NO 169
<211> LENGTH: 65
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(65)
<223> OTHER INFORMATION: All pyrimidines are 2'F.

<400> SEQUENCE: 169
gggaggacga ugcgggggga guauuaaaga gucuguauag cuuuaccccc agacgacucg    60
cccga    65

<210> SEQ ID NO 170
<211> LENGTH: 65
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(65)
<223> OTHER INFORMATION: All pyrimidines are 2'F.

<400> SEQUENCE: 170
gggaggacga ugcggggagg auauuauaga gucuguauag cuauaccccc agacgacucg    60
cccga    65

<210> SEQ ID NO 171
<211> LENGTH: 34
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(34)
<223> OTHER INFORMATION: All pyrimidines are 2'F; a's and g's at positions 1-5, 8, 11, 13-16, 20, 22, 24-25, 28 and 30 are 2'-OCH3; linkage at positions 34 and 35 is 3'-3'.

<400> SEQUENCE: 171
ggagguuauu acagagucug uauagcugua cucc    34

<210> SEQ ID NO 172
<211> LENGTH: 34
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(34)
<223> OTHER INFORMATION: All pyrimidines are 2'F; a's and g's at positions 11, 13-16, 20, 22, 24-25, 28 and 30 are 2'OCH3; linkage at positions 34 and 35 is 3'-3'.

<400> SEQUENCE: 172
ggagguuauu acagagucug uauagcugua cucc    34

<210> SEQ ID NO 173
<211> LENGTH: 34
<212> TYPE: RNA
<213> ORGANISM: Artificial Sequence
<220> FEATURE:
<223> OTHER INFORMATION: Description of Artificial Sequence: Synthetic Sequence
<221> NAME/KEY: modified_base
<222> LOCATION: (1)..(34)
<223> OTHER INFORMATION: All pyrimidines are 2'F; a's and g's at positions 1-4 are 2'OCH3; linkage at positions 34 and 35 is 3'-3'.

<400> SEQUENCE: 173
ggagguuauu acagagucug uauagcugua cucc    34

<210> SEQ ID NO 174
<211> LENGTH: 34
<212> TYPE: RNA
<213> ORGANISM: Artificial Sequence
<220> FEATURE:
<223> OTHER INFORMATION: Description of Artificial Sequence: Synthetic

```
      Sequence
<221> NAME/KEY: modified_base
<222> LOCATION: (1)..(34)
<223> OTHER INFORMATION: All pyrimidines are 2'F; a's and g's at
      positions 5, 8, and 11 are 2'OCH3; linkage at positions 34 and 35
      is 3'-3'.

<400> SEQUENCE: 174
ggagguuauu acagagucug uauagcugua cucc                              34

<210> SEQ ID NO 175
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; a' and g's at
      positions 13-16 are 2'-OCH3; linkage at positions 34 and 35 is
      3'-3'.

<400> SEQUENCE: 175
ggagguuauu acagagucug uauagcugua cucc                              34

<210> SEQ ID NO 176
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; a's and g's at
      positions 20, 22 and 24 are 2'-OCH3; linkage at positions 34 and
      35 is 3'-3'.

<400> SEQUENCE: 176
ggagguuauu acagagucug uauagcugua cucc                              34

<210> SEQ ID NO 177
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; a's and g's at
      positions 25, 28 and 30 are 2'-OCH3; linkage at positions 34 and
      35 is 3'-3'.

<400> SEQUENCE: 177
ggagguuauu acagagucug uauagcugua cucc                              34

<210> SEQ ID NO 178
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; g at position 20 is
      2'-OCH3; linkage at positions 34 and 35 is 3'-3'.

<400> SEQUENCE: 178
```
ggagguuauu acagagucug uauagcugua cucc 34

<210> SEQ ID NO 179
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; a at position 22 is
      2'-OCH3; linkage at positions 34 and 35 is 3'-3'.

<400> SEQUENCE: 179
ggagguuauu acagagucug uauagcugua cucc 34

<210> SEQ ID NO 180
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; a at position 24 is
      2'-OCH3; linkage at positions 34 and 35 is 3'-3'.

<400> SEQUENCE: 180
ggagguuauu acagagucug uauagcugua cucc 34

<210> SEQ ID NO 181
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; a's and g's at
      positions 1-5, 8, 11, 25 and 30 are 2'-OCH3; linkage at positions
      34 and 35 is 3'-3'.

<400> SEQUENCE: 181
ggagguuauu acagagucug uauagcugua cucc 34

<210> SEQ ID NO 182
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; a's and g's at
      positions 1-5, 8, 11, 13-16, 24-25, 28 and 30 are 2'-OCH3; linkage
      at positions 34 and 35 is 3'-3'.

<400> SEQUENCE: 182
ggagguuauu acagagucug uauagcugua cucc 34

<210> SEQ ID NO 183
<211> LENGTH: 34
<212> TYPE: RNA
<213> ORGANISM: Artificial Sequence
<220> FEATURE:

<223> OTHER INFORMATION: Description of Artificial Sequence: Synthetic
Sequence
<221> NAME/KEY: modified_base
<222> LOCATION: (1)..(34)
<223> OTHER INFORMATION: All pyrimidines are 2'F; a's and g's at
positions 1-5, 8, 11, 13-16, 20, 24-25, 28 and 30 are 2'-OCH3;
linkage at positions 34 and 35 is 3'-3'.

<400> SEQUENCE: 183
ggagguuauu acagagucug uauagcugua cucc                    34

<210> SEQ ID NO 184
<211> LENGTH: 34
<212> TYPE: RNA
<213> ORGANISM: Artificial Sequence
<220> FEATURE:
<223> OTHER INFORMATION: Description of Artificial Sequence: Synthetic
Sequence
<221> NAME/KEY: modified_base
<222> LOCATION: (1)..(34)
<223> OTHER INFORMATION: All pyrimidines are 2'F; a's and g's at
positions 1-5, 8, 11, 13-16, 25, 28 and 30 are 2'-OCH3; linkage at
positions 34 and 35 is 3'-3'.

<400> SEQUENCE: 184
ggagguuauu acagagucug uauagcugua cucc                    34

<210> SEQ ID NO 185
<211> LENGTH: 34
<212> TYPE: RNA
<213> ORGANISM: Artificial Sequence
<220> FEATURE:
<223> OTHER INFORMATION: Description of Artificial Sequence: Synthetic
Sequence
<221> NAME/KEY: modified_base
<222> LOCATION: (1)..(34)
<223> OTHER INFORMATION: All pyrimidines are 2'F; a's and g's at
positions 1-5, 11, 13-16, 25, 28, and 30 are 2'-OCH3; linkage at
positions 34 and 35 is 3'-3'.

<400> SEQUENCE: 185
ggagguuauu acagagucug uauagcugua cucc                    34

<210> SEQ ID NO 186
<211> LENGTH: 34
<212> TYPE: RNA
<213> ORGANISM: Artificial Sequence
<220> FEATURE:
<223> OTHER INFORMATION: Description of Artificial Sequence: Synthetic
Sequence
<221> NAME/KEY: modified_base
<222> LOCATION: (1)..(34)
<223> OTHER INFORMATION: All pyrimidines are 2'F; a's and g's at
positions 1-4, 13-16, 25, 28 and 30 are 2'-OCH3; linkage at
positions 34 and 35 is 3'-3'.

<400> SEQUENCE: 186
ggagguuauu acagagucug uauagcugua cucc                    34

<210> SEQ ID NO 187
<211> LENGTH: 33
<212> TYPE: RNA
<213> ORGANISM: Artificial Sequence
<220> FEATURE:
<223> OTHER INFORMATION: Description of Artificial Sequence: Synthetic
Sequence
<221> NAME/KEY: modified_base
<222> LOCATION: (1)..(33)
<223> OTHER INFORMATION: All pyrimidines are 2'F; a's and g's at
positions 1-5, 10, 12-15 24, 27 and 29 are 2'-OCH3; linkage at
positions 33 and 34 is 3'-3'.

<400> SEQUENCE: 187
ggagauauua cagagucugu auagcuguac ucc    33

<210> SEQ ID NO 188
<211> LENGTH: 32
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(32)
<223> OTHER INFORMATION: All pyrimidines are 2'F; a's and g's at
      positions 1-4, 10, 12-15, 24, 27 and 29 are 2'-OCH3; linkage at
      positions 32 and 33 is 3'-3'.

<400> SEQUENCE: 188
gggguuauua cagagucugu auagcuguac cc    32

<210> SEQ ID NO 189
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; linkage at positions
      34 and 35 is 3'-3'.

<400> SEQUENCE: 189
ugugaauauu agagagucug uauagcucua cccc    34

<210> SEQ ID NO 190
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; a's and g's at
      positions 2, 4-5, 8, 11, 13-16, 24-25 and 30 are 2'-OCH3; linkage
      at positons 34 and 35 is 3'-3'.

<400> SEQUENCE: 190
ugugaauauu agagagucug uauagcucua cccc    34

<210> SEQ ID NO 191
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; a's and g's at
      positions 2, 4-6, 8, 11-16, 20, 24-25, and 30 are 2'-OCH3; linkage
      at positions 34 and 35 is 3'-3'.

<400> SEQUENCE: 191
ugugaauauu agagagucug uauagcucua cccc    34

<210> SEQ ID NO 192
<211> LENGTH: 34

```
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; a's and g's at
      positions 2, 4, 11, 13-16, 25 and 30 are 2'-OCH3; linkage at
      positions 34 and 35 is 3'-3'.

<400> SEQUENCE: 192
ugugaauauu agagagucug uauagcucua cccc                             34

<210> SEQ ID NO 193
<211> LENGTH: 34
<212> TYPE: RNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(34)
<223> OTHER INFORMATION: All pyrimidines are 2'F; a's and g's at
      positions 2, 4-6, 11-16, 25 and 30 are 2'-OCH3; linkage at
      positions 34 and 35 is 3'-3'.

<400> SEQUENCE: 193
ugugaauauu agagagucug uauagcucua cccc                             34

<210> SEQ ID NO 194
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 1-3 and 5 are 2'-OMe.
<223> OTHER INFORMATION: Description of Artificial Sequence: Synthetic
      Sequence

<400> SEQUENCE: 194
gggugccuuu ugccuagguu gugauuugua accuucugcc ca                    42

<210> SEQ ID NO 195
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 12 and 16-18 are 2'OMe.
<223> OTHER INFORMATION: Description of Artificial Sequence: Synthetic
      Sequence

<400> SEQUENCE: 195
gggugccuuu ugccuagguu gugauuugua accuucugcc ca                    42

<210> SEQ ID NO 196
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 21, 23-24 and 28 are
      2'-OMe.
<223> OTHER INFORMATION: Description of Artificial Sequence: Synthetic
      Sequence

<400> SEQUENCE: 196
```
gggugccuuu ugccuagguu gugauuugua accuucugcc ca         42

<210> SEQ ID NO 197
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 30-31, 38 and 42 are
      2'-OMe.
<223> OTHER INFORMATION: Description of Artificial Sequence: Synthetic
      Sequence

<400> SEQUENCE: 197
gggugccuuu ugccuagguu gugauuugua accuucugcc ca         42

<210> SEQ ID NO 198
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 1, 21, 23-24 and 28
      are 2'-OMe.
<223> OTHER INFORMATION: Description of Artificial Sequence: Synthetic
      Sequence

<400> SEQUENCE: 198
gggugccuuu ugccuagguu gugauuugua accuucugcc ca         42

<210> SEQ ID NO 199
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 2, 21, 23-24 and 28
      are 2'-OMe.
<223> OTHER INFORMATION: Description of Artificial Sequence: Synthetic
      Sequence

<400> SEQUENCE: 199
gggugccuuu ugccuagguu gugauuugua accuucugcc ca         42

<210> SEQ ID NO 200
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 3, 21, 23-24 and 28
      are 2'-OMe.
<223> OTHER INFORMATION: Description of Artificial Sequence: Synthetic
      Sequence

<400> SEQUENCE: 200
gggugccuuu ugccuagguu gugauuugua accuucugcc ca         42

<210> SEQ ID NO 201
<211> LENGTH: 42
<212> TYPE: RNA
<213> ORGANISM: Artificial Sequence
<220> FEATURE:
<221> NAME/KEY: modified_base
<222> LOCATION: (1)..(42)

<223> OTHER INFORMATION: A's and g's at positions 5, 21, 23-24 and 28 are 2'-OMe.
<223> OTHER INFORMATION: Description of Artificial Sequence: Synthetic Sequence

<400> SEQUENCE: 201
gggugccuuu ugccuagguu gugauuugua accuucugcc ca        42

<210> SEQ ID NO 202
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 12, 21, 23-24 and 28 are 2'-OMe.
<223> OTHER INFORMATION: Description of Artificial Sequence: Synthetic Sequence

<400> SEQUENCE: 202
gggugccuuu ugccuagguu gugauuugua accuucugcc ca        42

<210> SEQ ID NO 203
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 16, 21, 23-24 and 28 are 2'-OMe.
<223> OTHER INFORMATION: Description of Artificial Sequence: Synthetic Sequence

<400> SEQUENCE: 203
gggugccuuu ugccuagguu gugauuugua accuucugcc ca        42

<210> SEQ ID NO 204
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 17, 21, 23-24 and 28 are 2'-OMe.
<223> OTHER INFORMATION: Description of Artificial Sequence: Synthetic Sequence

<400> SEQUENCE: 204
gggugccuuu ugccuagguu gugauuugua accuucugcc ca        42

<210> SEQ ID NO 205
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 18, 21, 23-24, and 28 are 2'-OMe.
<223> OTHER INFORMATION: Description of Artificial Sequence: Synthetic Sequence

<400> SEQUENCE: 205
gggugccuuu ugccuagguu gugauuugua accuucugcc ca        42

<210> SEQ ID NO 206

<210> SEQ ID NO 206 (implied continuation)
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 21, 23-24, 28 and 30 are 2'-OMe.
<223> OTHER INFORMATION: Description of Artificial Sequence: Synthetic Sequence

<400> SEQUENCE: 206
gggugccuuu ugccuagguu gugauuugua accuucugcc ca          42

<210> SEQ ID NO 207
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 21, 23-24, 28 and 31 are 2'-OMe.
<223> OTHER INFORMATION: Description of Artificial Sequence: Synthetic Sequence

<400> SEQUENCE: 207
gggugccuuu ugccuagguu gugauuugua accuucugcc ca          42

<210> SEQ ID NO 208
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 21, 23-24, 28 and 38 are 2'-OMe.
<223> OTHER INFORMATION: Description of Artificial Sequence: Synthetic Sequence

<400> SEQUENCE: 208
gggugccuuu ugccuagguu gugauuugua accuucugcc ca          42

<210> SEQ ID NO 209
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 21, 23-24, 28 and 42 are 2'-OMe.
<223> OTHER INFORMATION: Description of Artificial Sequence: Synthetic Sequence

<400> SEQUENCE: 209
gggugccuuu ugccuagguu gugauuugua accuucugcc ca          42

<210> SEQ ID NO 210
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 1-3, 16-18, 21, 23-24, 28, 30-31 and 42 are 2'-OMe; linkage at positions 42 and 43 is 3'-3'.
<223> OTHER INFORMATION: Description of Artificial Sequence: Synthetic Sequence -continued

<400> SEQUENCE: 210
gggugccuuu ugccuagguu ugauuugua accuucugcc ca    42

<210> SEQ ID NO 211
<211> LENGTH: 42
<212> TYPE: RNA
<213> ORGANISM: Artificial Sequence
<220> FEATURE:
<221> NAME/KEY: modified_base
<222> LOCATION: (1)..(42)
<223> OTHER INFORMATION: A's and g's at positions 1-3, 16-18, 21, 23-24,
      28, 30 and 42 are 2'-OMe; linkage at positions 42 and 43 is 3'-3'.
<223> OTHER INFORMATION: Description of Artificial Sequence: Synthetic
      Sequence

<400> SEQUENCE: 211
gggugccuuu ugccuagguu ugauuugua accuucugcc ca    42

<210> SEQ ID NO 212
<211> LENGTH: 41
<212> TYPE: RNA
<213> ORGANISM: Artificial Sequence
<220> FEATURE:
<221> NAME/KEY: modified_base
<222> LOCATION: (1)..(41)
<223> OTHER INFORMATION: A's and g's at positions 1-3, 16-18, 21, 23-24,
      28 and 30-31 are 2'-OMe; linkage at positions 41 and 42 are 3'-3'.
<223> OTHER INFORMATION: Description of Artificial Sequence: Synthetic
      Sequence

<400> SEQUENCE: 212
gggugccuuu ugccuagguu ugauuugua accuucugcc c    41

<210> SEQ ID NO 213
<211> LENGTH: 37
<212> TYPE: RNA
<213> ORGANISM: Artificial Sequence
<220> FEATURE:
<221> NAME/KEY: modified_base
<222> LOCATION: (1)..(37)
<223> OTHER INFORMATION: A's and g's at positions 1-3, 16-18, 21, 23,
      25-26 and 37 are 2'-OMe; linkage at positions 37 and 38 is 3'-3'.
<223> OTHER INFORMATION: Description of Artificial Sequence: Synthetic
      Sequence

<400> SEQUENCE: 213
gggugccuuu ugccuagguu uguaaccuu cugccca    37

<210> SEQ ID NO 214
<211> LENGTH: 35
<212> TYPE: RNA
<213> ORGANISM: Artificial Sequence
<220> FEATURE:
<221> NAME/KEY: modified_base
<222> LOCATION: (1)..(35)
<223> OTHER INFORMATION: A's and g's at positions 1-3, 16-18, 21, 23-24
      and 35 are 2'-OMe; linkage at positions 35 and 36 is 3'-3'.
<223> OTHER INFORMATION: Description of Artificial Sequence: Synthetic
      Sequence

<400> SEQUENCE: 214
gggugccuuu ugccuagguu guaaccuucu gccca    35

<210> SEQ ID NO 215
<211> LENGTH: 33
<212> TYPE: RNA
<213> ORGANISM: Artificial Sequence
<220> FEATURE:

-continued

```
<221> NAME/KEY: modified_base
<222> LOCATION: (1)..(33)
<223> OTHER INFORMATION: A's and g's at positions 1-3, 16-18, 21-22, and
      33 are 2'-OMe; linkage at positions 33 and 34 is 3'-3'.
<223> OTHER INFORMATION: Description of Artificial Sequence:  Synthetic
      Sequence

<400> SEQUENCE: 215
gggugccuuu ugccuagguu aaccuucugc cca                               33

<210> SEQ ID NO 216
<211> LENGTH: 42
<212> TYPE: RNA
<213> ORGANISM: Artificial Sequence
<220> FEATURE:
<223> OTHER INFORMATION: Description of Artificial Sequence:  Synthetic
      Sequence

<400> SEQUENCE: 216
gggugccuuu ugccuagguu gugauuugua accuucugcc ca                     42
```